United States Patent [19]

Maywald et al.

[11] Patent Number: 5,201,932
[45] Date of Patent: Apr. 13, 1993

[54] CARBOXAMIDES

[75] Inventors: Volker Maywald, Ludwigshafen; Wolfgang Freund, Neustadt; Gerhard Hamprecht, Weinheim; Thomas Kuekenhoehner; Peter Plath, both of Frankenthal; Bruno Wuerzer, Otterstadt; Karl-Otto Westphalen, Speyer, all of Fed. Rep. of Germany

[73] Assignee: BASF Aktiengesellschaft, Ludwigshafen, Fed. Rep. of Germany

[21] Appl. No.: 877,365

[22] Filed: May 4, 1992

Related U.S. Application Data

[63] Continuation of Ser. No. 585,174, Sep. 20, 1990, abandoned.

[30] Foreign Application Priority Data

Sep. 22, 1989 [DE] Fed. Rep. of Germany ....... 3931627
Oct. 11, 1989 [DE] Fed. Rep. of Germany ....... 3933898

[51] Int. Cl.$^5$ .................. A01N 43/40; C07D 413/02; C07D 261/06
[52] U.S. Cl. .................... 504/271; 546/209; 548/248; 504/269; 504/193; 504/196; 504/266; 504/252; 504/270; 504/262; 504/263; 504/242; 504/239; 504/248; 504/249; 504/191; 504/265
[58] Field of Search ....................... 548/248; 546/209; 71/88, 77, 94

[56] References Cited

U.S. PATENT DOCUMENTS

| | | | |
|---|---|---|---|
| 3,409,616 | 11/1968 | Conover | 260/247.2 |
| 3,502,660 | 3/1970 | Butler et al. | 260/240 |
| 3,524,862 | 8/1970 | Conover | 260/307.5 |
| 3,699,117 | 10/1972 | Butler et al. | 260/307.5 |
| 5,001,124 | 3/1991 | Patterson et al. | 514/236.8 |

OTHER PUBLICATIONS

Journal of Heterocyclic Chemistry, Nov.-Dec. 1985.
Journal of the Chemical Society, 1965, pp. 7277-7282, London GB.
Chemical Abstracts, vol. 97, No. 3, Jul. 19, 1982.
Journal of the Chemical Society Perkin Transactions I, 1987.
Journal of the Chemical Society, 1959, pp. 3061-3072.
Journal of the Chemical Soc., (1959) 3061 (CA 54:12113).
Journal of the Chem. Soc., (1965) 7277 (CA 64:5065b).
J. Heterocycl. Chem. 22, 1561 (1985).
Gass. Chim. Ital., 97(1), 25-33 (1967).
Perkins Trans. I, 2391-2394 (1982).

Primary Examiner—Mary C. Lee
Assistant Examiner—Joseph K. McKane
Attorney, Agent, or Firm—Herbert B. Keil

[57] ABSTRACT

Carboxamides Ia, Ib, Ic and Id (X=O, S; $R^1$=H, halogen, substituted or unsubstituted alkyl, substituted or unsubstituted benzyl, alkoxy, alkylthio, haloalkoxy, haloalkylthio, substituted or unsubsti- (Abstract continued on next page.)

tuted phenyl, substituted or unsubstituted phenoxy or phenylthio, a substituted or unsubstituted 5- or 6-membered heterocyclic radical containing one or two heteroatoms, cycloalkyl-substituted alkyl, substituted or unsubstituted alkenyl which may be epoxidized, substituted or unsubstituted alkynyl, substituted or unsubstituted cycloalkyl or cycloalkenyl; $R^{1'}$=cycloalkyl-substituted alkyl, substituted or unsubstituted alkenyl which may be epoxidized, substituted or unsubstituted cycloalkenyl; $R^2$=CHO, 4,5-dihydrooxazol-2-yl, $COYR^5$, $CONR^6R^7$; Y=O, S; $R^5$=H, substituted or unsubstituted alkyl, cycloalkyl, substituted or unsubstituted alkenyl, substituted or unsubstituted cycloalkenyl, substituted or unsubstituted alkynyl, substituted or unsubstituted phenyl, a 5- or 6-membered heterocyclic radical containing up to 3 heteroatoms, benzotriazole, N-phthalimido, tetrahydrophthalimido, succinimido, maleiimido, 2,2-dimethyl-1,3-dioxolan-4-ylmethyl, 1,3-dioxolan-2-on-4-ylmethyl, and when Y=O: one equivalent of a cation from the group of the alkali or alkaline earth metals, Mn, Cu, Fe ammonium and substituted ammonium, a radical —N=$CR^8R^9$ or —W—Z; $R^8$, $R^9$=H, substituted or unsubstituted alkyl, substituted or unsubstituted haloalkyl, cycloalkyl, alkoxy, furanyl, substituted or unsubstituted phenyl; $R^8+R^9$=4–7-membered methylene chain; W=alkylene chain, ethoxyethylene chain, butylene, butynylene chain; Z=a molecular moiety bonded to W in the ω-position and is the same as that linked to W in the α-position of W; $R^6$=H, alkyl, cycloalkyl; $R^7$=H; alkyl; —C(O-alkyl)=N—H or —(O—alkyl)=N—alkyl; $R^6+R^7$=4–5-membered methylene chain; $R^3$=H, substituted or unsubstituted alkyl, substituted or unsubstituted cycloalkyl; $R^4$=H, OH, alkoxy, subsituted or unsubstituted alkyl, substituted or unsubstituted cycloalkyl, substituted or unsubstituted alkenyl, substituted or unsubstituted alkynyl, di-($C_1$–$C_4$)-alkylamino, a substituted or unsubstituted 5- or 6-membered heterocyclic radical containing one or two heteroatoms, substituted or unsubstituted phenyl, substituted or unsubstituted naphthyl; $R_3+R_4$=4–7-membered methylene chain which may be interrupted by O, S or N—$CH_3$, or —$(CH_2)_3$—CO—)

and their environmentally tolerated salts.

The compounds Ia to Id are suitable as herbicides.

27 Claims, No Drawings

CARBOXAMIDES

This application is a continuation of application Ser. No. 07/585,174, filed on Sep. 20, 1990, now abandoned.

The present invention relates to carboxamides of the formulae Ia, Ib, Ic and Id

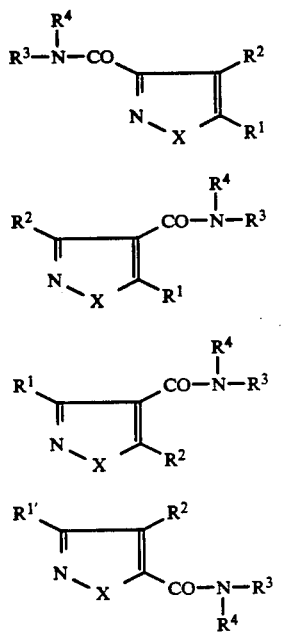

where
X is oxygen or sulfur;
$R^1$ is
hydrogen, halogen, $C_1$–$C_6$-alkyl which may carry from one to five halogen atoms and/or a cyano radical and/or up to two of the following radicals: $C_1$–$C_4$-alkoxy, partially or fully halogenated $C_1$–$C_4$-alkoxy, $C_1$–$C_4$-alkylthio or partially or fully halogenated $C_1$–$C_4$-alkylthio;

$C_1$–$C_4$-alkoxy or $C_1$–$C_4$-alkylthio, partially or fully halogenated $C_1$–$C_4$-alkoxy, partially or fully halogenated $C_1$–$C_4$-alkylthio;

benzyl which may be monosubstituted, disubstituted or trisubstituted by $C_4$–$C_4$-alkyl, partially or fully halogenated $C_1$–$C_4$-alkyl, $C_1$–$C_4$-alkoxy, partially or fully halogenated $C_1$–$C_4$-alkoxy, $C_1$–$C_4$-alkylthio, partially or fully halogenated $C_1$–$C_4$-alkylthio, halogen, cyano or nitro;

phenyl which may also carry from one to three of the following radicals cyano, nitro, halogen, $C_1$–$C_6$-alkyl, partially or fully halogenated $C_1$–$C_6$-alkyl, $C_1$–$C_6$-alkoxy, partially or fully halogenated $C_1$–$C_6$-alkoxy, $C_1$–$C_6$-alkylthio and/or partially or fully halogenated $C_1$–$C_6$-alkylthio;

phenoxy or phenylthio, each of which may be monosubstituted, disubstituted or trisubstituted by $C_1$–$C_4$-alkyl, partially or fully halogenated $C_1$–$C_4$-alkyl, $C_1$–$C_4$-alkoxy, partially or fully halogenated $C_1$–$C_4$-alkoxy, $C_1$–$C_4$-alkylthio, partially or fully halogenated $C_1$–$C_4$-alkylthio, halogen, cyano or nitro;

a 5- to 6-membered saturated or aromatic heterocyclic radical containing one or two heteroatoms selected from the group comprising oxygen, sulfur and nitrogen which may carry one or two of the following substituents: halogen, $C_1$–$C_3$-alkyl, $C_1C_3$-alkoxy and $C_1$–$C_3$-alkoxycarbonyl;

$C_2$–$C_6$-cycloalkyl-substituted $C_1$–$C_6$-alkyl;

$C_2$–$C_6$-alkenyl whose double bond may be epoxidized, or $C_2$–$C_6$-alkynyl, it being possible for both groups to be monosubstituted, disubstituted or trisubstituted by halogen, $C_1$–$C_3$-alkoxy and/or monosubstituted by cyclopropyl or phenyl, it also being possible for the phenyl radical to carry up to three of the following substituents: halogen, cyano, nitro, $C_1$–$C_4$-alkyl, which may be unsubstituted or partially or fully halogenated, $C_1$–$C_4$-alkoxy or $C_1$–$C_4$-alkylthio, both of which may be unsubstituted or partially or fully halogenated;

$C_3$–$C_8$-cycloalkyl or $C_3$–$C_6$-cycloalkenyl, it being possible for both groups to be monosubstituted, disubstituted or trisubstituted by $C_1$–$C_4$-alkyl or halogen;

$R^{1'}$ is
$C_3$–$C_8$-cycloalkyl-substituted $C_1$–$C_6$-alkyl;

$C_2$–$C_6$-alkenyl whose double bond may be epoxidized, or $C_2$–$C_6$-alkynyl, it being possible for both groups to be monosubstituted, disubstituted or trisubstituted by halogen, $C_1$–$C_3$-alkoxy and/or monosubstituted by cyclopropyl or phenyl, it also being possible for the phenyl radical to carry up to three of the following substituents: halogen, cyano, nitro, $C_1$–$C_4$-alkyl, which may be unsubstituted or partially or fully halogenated, $C_1$–$C_4$-alkoxy or $C_1$–$C_4$-alkylthio, both of which may be unsubstituted or partially or fully halogenated;

$C_3$–$C_6$-cycloalkenyl, which may be monosubstituted, disubstituted or trisubstituted by halogen or $C_1$–$C_4$-alkyl;

$R^2$ is
formyl, 4,5-dihydrooxazol-2-yl,
$COYR^5$ or $CONR^6R^7$, where
Y is oxygen or sulfur;
$R^5$ is
hydrogen;
$C_1$–$C_6$-alkyl which may carry from one to five halogen atoms and/or up to three hydroxyl and/or $C_1$–$C_4$-alkoxy groups and/or one of the following radicals:
cyano,
$C_1$–$C_4$-alkoxy-$C_2$–$C_4$-alkoxy,
$C_1$–$C_3$-alkylthio,
$C_1$–$C_3$-alkylamino, di($C_1$–$C_3$)-alkylamino, $C_1$–$C_6$-cycloalkylamino or di($C_3$–$C_6$)-cycloalkylamino,
trimethylsilyl,
$C_1$–$C_3$-alkylsulfinyl or $C_1$–$C_3$-alkylsulfonyl,
carboxyl, $C_1$–$C_3$-alkoxycarbonyl, $C_1$–$C_3$-alkoxycarbonyl-$C_1$–$C_3$-alkoxy or $C_1$–$C_3$-alkoxycarbonyl-$C_1$–$C_3$-alkoxy-$C_1$–$C_3$-alkoxycarbonyl,
di($C_1$–$C_3$)-alkylaminocarbonyl,
di($C_1$–$C_3$)-alkoxyphosphonyl,
$C_1$–$C_6$-alkaneiminoxy or $C_5$–$C_6$-cycloalkaneiminoxy,
N-phthalimido, N-succinimido, benzyloxy, benzoyl, it being possible for these cyclic radicals to additionally carry from one to three of the following groups: halogen, $C_1$–$C_3$-alkyl or $C_1$–$C_3$-alkoxy, a 5- or 6-membered saturated heterocyclic radical or a 5- or 6-membered heteroaromatic radical, each of which has up to three heteroatoms selected from the group comprising oxygen, sulfur and nitrogen, where two oxygen and/or sulfur atoms must not be directly adjacent and where the heterocyclic rings may also carry one or two of the following substituents: halogen, $C_1$–$C_3$-alkyl, $C_1$–$C_3$-alkoxy or $C_1$–$C_3$-alkoxycarbonyl;

phenyl, which may also carry up to three of the following substituents: halogen, nitro, cyano, $C_1$–$C_3$-alkyl, partially or fully halogenated $C_1$–$C_3$-alkyl, $C_1$–$C_3$-alkoxy or partially or fully halogenated $C_1$–$C_3$-alkoxy;

—$CR^{10}$=N—$R^{11}$, where $R^{10}$ is hydrogen or $C_1$–$C_6$-alkyl and $R^{11}$ is $C_1$–$C_6$-alkoxy, $C_3$–$C_6$-alkenyloxy or $C_3$–$C_6$-alkynyloxy, each of which may carry up to 3 halogen atoms and/or a phenyl radical with, if desired, up to three of the following radicals halogen, nitro, cyano, $C_1$–$C_3$-alkyl or $C_1$–$C_3$-alkoxy; phenoxy, which may also carry up to three of the following substituents: halogen, nitro, cyano, $C_1$–$C_3$-alkyl or $C_1$–$C_3$-alkoxy; $C_1$–$C_6$-alkylamino, di($C_1$–$C_6$)alkylamino or phenylamino, it being possible for the aromatic ring to additionally carry up to three of the following radicals: halogen, nitro, cyano, $C_1$–$C_3$-alkyl or $C_1$–$C_3$-alkoxy;

$C_3$–$C_8$-cycloalkyl;

$C_3$–$C_6$-alkenyl, $C_5$–$C_6$-cycloalkenyl, $C_3$–$C_6$-alkynyl, it being possible for these radicals to carry one of the following groups: hydroxyl, halogen, $C_1$–$C_4$-alkoxy or phenyl, it being possible for the aromatic radical to itself carry from one to three of the following groups: halogen, nitro, cyano, $C_1$–$C_4$-alkyl, partially or fully halogenated $C_1$–$C_4$-alkyl or $C_1$–$C_4$-alkoxy; phenyl, which may carry from one to three of the following groups: halogen, nitro, cyano, $C_1$–$C_4$-alkyl, partially or fully halogenated $C_1$–$C_4$-alkyl, $C_1$–$C_4$-alkoxy, partially or fully halogenated $C_1$–$C_4$-alkoxy or $C_1$–$C_4$-alkoxycarbonyl;

a five- or six-membered heterocyclic radical having up to three heteroatoms selected from the group comprising oxygen, sulfur and nitrogen, where two oxygen and/or sulfur atoms must not be directly adjacent and where the heterocyclic rings may also carry one or two of the following substituents: halogen, $C_1$–$C_3$-alkyl, $C_1$–$C_3$-alkoxy or $C_1$–$C_3$-alkoxycarbonyl;

benzotriazolyl;

N-phthalimido, tetrahydrophthalimido, succinimido, maleiimido;

2,2-dimethyl-1,3-dioxolan-4-ylmethyl or 1,3-dioxolan-2-on-4-ylmethyl;

in the case where Y=O: one equivalent of a cation from the group comprising the alkali and alkaline earth metals, manganese, copper, iron, ammonium and ammonium which is substituted by up to 4 $C_1$–$C_3$-alkyl groups; or —N=$CR^8R^9$, where $R^8$ and $R^9$ are hydrogen; $C_1$–$C_4$-alkyl, which may be unsubstituted or partially or fully halogenated and may carry a $C_1$–$C_3$-alkoxy or phenyl radical, it being possible for the aromatic radical to itself also be monosubstituted, disubstituted or trisubstituted by halogen, nitro, cyano, $C_1$–$C_3$-alkyl, partially or fully halogenated $C_1$–$C_3$-alkyl, $C_1$–$C_3$-alkoxy or partially or fully halogenated $C_1$–$C_3$-alkoxy; $C_3$–$C_6$-cycloalkyl; $C_1$–$C_4$-alkoxy; furanyl or phenyl, which may additionally carry up to three of the following substituents: halogen, nitro, cyano, $C_1$–$C_3$-alkyl, partially or fully halogenated $C_1$–$C_3$-alkyl, $C_1$–$C_3$-alkoxy or partially or fully halogenated $C_1$–$C_3$-alkoxy; or $R^8$ and $R^9$ together are a methylene chain having from 4 to 7 members;

—W—Z, where W is $C_2$–$C_4$-alkylene, ethoxyethylene, but-2-enylene or but-2-ynylene, and Z is a molecular moiety which is bonded to W in the $\omega$-position and is the same as that linked to W in the $\alpha$-position of W;

$R^6$ is hydrogen, $C_1$–$C_6$-alkyl or $C_3$–$C_6$-cycloalkyl, and $R^7$ is hydrogen, $C_1$–$C_6$-alkyl, —$C(OR^{12})$=N—H or —$C(OR^{12})$=N—($C_1$–$C_4$)-alkyl, where $R^{12}$ is $C_1$–$C_4$-alkyl, or $R^6$ and $R^7$ together are methylene having 4 or 5 members;

$R^3$ is hydrogen;

$C_1$–$C_6$-alkyl, which may carry from one to three of the following substituents: hydroxyl, halogen, $C_1$–$C_4$-alkoxy, $C_1$–$C_4$-alkylthio or di($C_1$–$C_4$)-alkylamino;

$C_3$–$C_8$-cycloalkyl, which may be monosubstituted, disubstituted or trisubstituted by halogen, $C_1$–$C_4$-alkyl or partially or fully halogenated $C_1$–$C_4$-alkyl;

$R^4$ is hydrogen, hydroxyl, $C_1$–$C_4$-alkoxy;

$C_1$–$C_6$-alkyl, which may carry from one to three of the following radicals: halogen, cyano, $C_1$–$C_4$-alkoxy, partially or fully halogenated $C_1$–$C_4$-alkoxy, $C_1$–$C_4$-alkylthio, partially or fully halogenated $C_1$–$C_4$-alkylthio, di-$C_1$–$C_4$-alkylamino, $C_3$–$C_8$-cycloalkyl or phenyl, it being possible for the phenyl ring to itself carry from one to three of the following radicals: halogen, cyano, nitro, $C_1$–$C_4$-alkyl, partially or fully halogenated $C_1$–$C_4$-alkyl, $C_1$–$C_4$-alkoxy, partially or fully halogenated $C_1$–$C_4$-alkoxy, $C_1$–$C_4$-alkylthio or partially or fully halogenated $C_1$–$C_4$-alkylthio;

$C_3$–$C_8$-cycloalkyl, which may carry from one to three of the following radicals: halogen, nitro, cyano, $C_1$–$C_6$-alkyl, partially or fully halogenated $C_1$–$C_6$-alkyl, $C_1$–$C_4$-alkoxy or partially or fully halogenated $C_1$–$C_4$-alkoxy;

$C_3$–$C_6$-alkenyl or $C_3$–$C_6$-alkynyl, each of which may be monosubstituted, disubstituted or trisubstituted by halogen and/or monosubstituted by phenyl, it being possible for the phenyl radical to itself carry from one to three of the following groups: $C_1$–$C_4$-alkyl, $C_1$–$C_4$-haloalkyl, $C_1$–$C_4$- alkoxy, $C_1$-$C_4$-haloalkoxy, $C_1$-$C_4$-alkylthio, $C_1$-$C_4$-haloalkylthio, halogen, cyano or nitro; di($C_1$-$C_4$)-alkylamino;

a 5- or 6-membered heterocyclic saturated or aromatic radical having one or two heteroatoms selected from the group comprising oxygen, sulfur and nitrogen, which may be monosubstituted, disubstituted or trisubstituted by $C_1$-$C_4$-alkyl or halogen;

phenyl, which may carry from one to four of the following groups: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, halogen, nitro, cyano, formyl, $C_1$-$C_4$-alkanoyl, $C_1$-$C_4$-haloalkanoyl or $C_1$-$C_4$-alkoxycarbonyl; naphthyl, which may be monosubstituted, disubstituted or trisubstituted by $C_1$-$C_4$-alkyl or halogen;

or $R^3$ and $R^4$ together are methylene having from 4 to 7 members which may be interrupted by oxygen, sulfur or N-methyl, or are —$(CH_2)_3$—CO—, $R^3$ and $R^4$ in the compounds Ia to Ic not simultaneously being hydrogen if $R^1$ is hydrogen, methyl or phenyl and $R^2$ is $CONH_2$, COOH or $COOCH_3$, or if X is oxygen, $R^1$ is $CH(OCH_2CH_3)_2$ and $R^2$ is $CONH_2$, and the agriculturally acceptable salts of the compounds Ia to Id.

The present invention also relates to herbicides which contain compounds Ia to Id as active ingredients and to herbicides which contain at least one compound Ia', Ib' or Ic' in which the substituents are as defined above and $R^3$ and $R^4$ may simultaneously be hydrogen if $R^1$ is hydrogen, methyl or phenyl and $R^2$ is $CONH_2$, $CO_2H$ or $CO_2CH_3$, or if X is oxygen, $R^1$ is $CH(OCH_2CH_3)_2$ and $R^2$ is $CONH_2$.

Isoxazole- and isothiazole-carboxylic acids and derivatives thereof are known. These are the following carboxamides of the type Ia', Ib' and Ic'

| | X | $R^1$ | $R^2$ | $R^3$ | $R^4$ | Ref. |
|---|---|---|---|---|---|---|
| Ia' | | | | | | |
| 1. | O | $CH(OCH_2CH_3)_2$ | $CONH_2$ | H | H | 1 |
| 2. | S | H | $CONH_2$ | H | H | 2 |
| 3. | S | H | COOH | H | H | 2 |
| Ib' | | | | | | |
| 1. | S | H | COOH | H | H | 2 |
| Ic' | | | | | | |
| 1. | S | H | COOH | H | H | 3 |
| 2. | O | Ph | COOH | H | H | 4 |
| 3. | O | Ph | $COOCH_3$ | H | H | 4 |
| 4. | O | $CH_3$ | COOH | H | H | 5 |

1 K. Butler; L. H. Conover, R. B. Woodward, U.S., U.S. Pat. No. 3,699,117, 17 Oct. 1972, 40 pp; CA 78(1): 4027x, CA 73(23): 120 602b, CA 73(3): 14574j, CA 70(15): 68002c
2 J. Chem. Soc., (1965) 7277
3 J. Chem. Soc., (1959) 3061
4 G. Desimoni, P. Gruenager, Gazz. Chim. Ital., 97(1), (1967) 25-33
5 A. Camparini; F. Ponticelli, P. Tedeschi, J. Chem. Soc., Perkin Trans 1, (10), (1982) 2391-4

Of the type Id, these are 5-aminocarbonyl-3-methyl-4-isoxazolecarboxylic acid, ethyl 5-aminocarbonyl-3-methyl-4-isoxazolecarboxylate, isothiazole-4,5-dicarboxamide and 5-carbamoyl-4-isothiazolecarboxylic acid (J. Chem. Soc. Perkin Trans I, 1982, 2391; J. Heterocyclic Chem. 22, (1985), 1561 and J. Chem. Soc. 1959, 3061).

However, the use of these compounds as herbicides is not known.

It is an object of the present invention to provide novel herbicidally active compounds.

We have found that this object is achieved by the carboxamides Ia, Ib, Ic and Id defined at the outset.

In addition, the present invention relates to processes for the preparation of these compounds, and to herbicides which contain compounds Ia, Ib, Ic and/or Id.

The novel carboxamides Ia, Ib, Ic and Id can be prepared by various processes, preferably by the following:

1. A process for the preparation of a compound of the formula Ia or Ib in which $R^2$ is $CO_2CH_3$ and X is oxygen

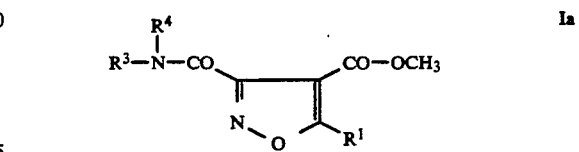

Ia

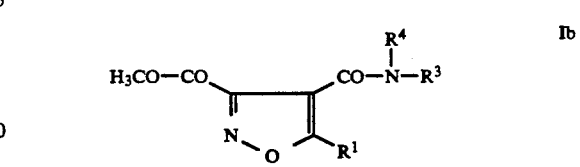

Ib

The carboxamide Ia or Ib is obtained by reacting the hydroxamyl chloride II in a conventional manner with a β-keto ester III in the presence of a base, subsequently first hydrolyzing the resultant dimethyl diester IV using one equivalent of an aqueous base to give the monoester Va or Vb, and then converting Va or Vb, separately or as a mixture, first into the halide or another activated form of the carboxylic acid in a conventional manner and subsequently amidating this derivative using an amine VIa.

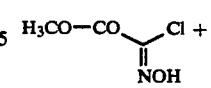

II

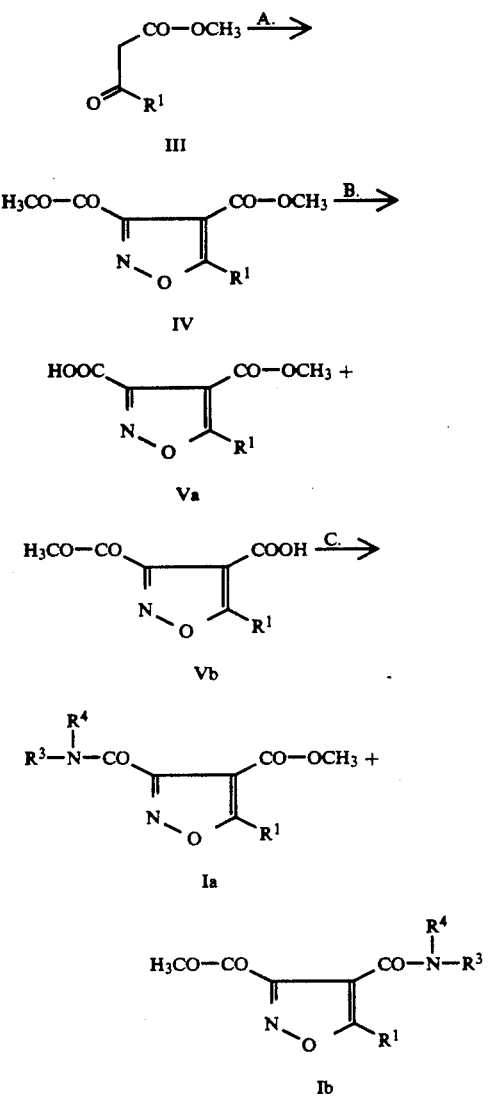

The individual reaction steps A, B and C of this synthesis can be carried out as follows:

Reaction step A:

The reaction is generally carried out at from 0° to 50° C., preferably from 10° to 30° C., in an inert, aprotic, polar organic solvent in the presence of a base.

The solvent used is expediently a hydrocarbon, such as, in particular, benzene, toluene, o-, m- or p-xylene, or an ether, such as diethyl ether, tert-butyl methyl ether, tetrahydrofuran, dimethoxyethane, ethylene glycol dimethyl ether or dioxane.

A particularly suitable base is sodium hydride.

The reaction is usually carried out by first converting the β-keto ester III into the anion in the solvent containing from 1 to 2 mol equivalents of the base. This solution of the anion of III is subsequently treated with a solution of II, and the mixture is kept at the reaction temperature. The reaction is generally complete after from 4 to 12 hours.

Before work-up of the products, it is advisable to remove the water of reaction by azeotropic distillation.

Reaction step B:

The partial hydrolysis of the dimethyl diester IV to give the monoester Va or Vb is usually carried out at from −40° to 20° C., preferably from −20° to 0° C., in an inert, water-miscible organic solvent in the presence of from 1 to 1.1 mol equivalents of a base.

Particularly suitable bases are hydroxides of alkali metal cations. The base is generally added as a 5 to 10 percent strength aqueous solution.

Examples of preferred solvents for this reaction are tetrahydrofuran and dioxane.

For work-up, the reaction mixture is usually acidified, the desired product separating out as a solid or oil, and being isolated in a conventional manner by filtration or extraction.

The mixture of the two isomeric monoesters Va and Vb can be resolved by fractional crystallization or by chromatography or the reaction sequence can be continued without resolving the isomers.

Reaction step C:

The compound Ia or Ib is obtained form the monoester Va or Vb respectively by converting Va or Vb first into the halide or another activated form of the carboxylic acid function in a conventional manner and subsequently aminating this derivative using an amine VIa.

In addition to the halides, such as, in particular, the chlorides and the bromides, examples of activated forms of the carboxylic acid are also imidazolides. In general, the halides are preferred.

They are obtained by reacting the carboxylic acid Va or Vb with a halogenating agent, such as phosgene, thionyl chloride, thionyl bromide, phosphorus oxychloride, phosphorus oxybromide, phosphorus trichloride, phosphorus pentachloride, phosphorus tribromide, phosphorus pentabromide, elemental chlorine or elemental bromine.

The halogenating agent is employed in an amount of from 1 to 5 mol equivalents, preferably from 1 to 2 mol equivalents.

The reaction proceeds at from 20° C. to the boiling point of the halogenating agent or, if using an inert organic solvent, to its boiling point.

Examples of suitable solvents are hydrocarbons, such as benzene, toluene, o-, m- and p-xylene, halogenated hydrocarbons, such as dichloromethane, chloroform, 1,2-dichloroethane, 1,1,2,2-tetrachloroethane, chlorobenzene and 1,2-dichlorobenzene, and mixtures of these.

The activated carboxylic acid derivative is usually isolated, for example by removing the halogenating agent and, if present, the solvent by distillation and only then reacted with the amine VIa.

In this case, the amidation is carried out at from −20° to 50° C., preferably from 0° to 30° C., in an inert, aprotic, polar organic solvent Particularly suitable solvents for this reaction are hydrocarbons, such as benzene, toluene, o-, m- and p-xylene, halogenated hydrocarbons, such as dichloromethane, and ethers, such as dimethyl ether and tertbutyl methyl ether.

Since hydrogen halide is formed during the amidation of acyl halides, it is advisable to add the amine VIa in an excess of from 2 to 5 mole equivalents, preferably from 2 to 3 mole equivalents. If the amine is employed in an equimolar amount (from 1 to 1.2 mol equivalents), a base, in particular a tertiary amine, such as triethylamine or pyridine, should be added to bind the hydrogen halide.

If starting from a mixture of the monoesters Va and Vb, a mixture of the isomeric carboxamides Ia and Ib is obtained in the reaction. This mixture can be separated into the individual components in a conventional manner, for example by fractional crystallization or chromatography.

2. A process for the preparation of a compound Ia in which X is oxygen, $R^2$ is $CO-OR^5$ and $R^5$ is not hydrogen or methyl:

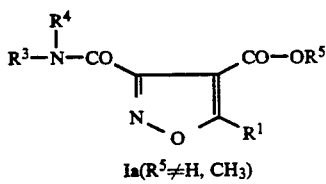

Ia($R^5 \neq H, CH_3$)

In a similar manner to that outlined under 1., this compound Ia is obtained by reacting the hydroxamyl chloride II with a β-keto ester of the formula IIIa in the above-outlined manner, subsequently cleaving the resultant diester IVa using a hydrolyzing agent to give the monoester Va', activating the latter and amidating product to give Ia.

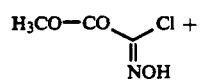

II

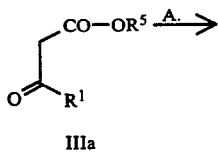

IIIa

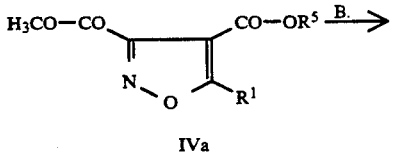

IVa

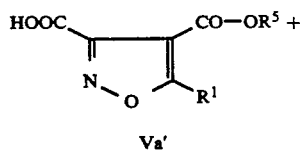

Va'

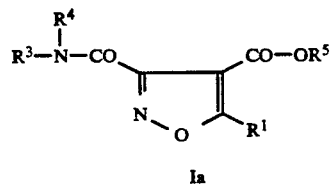

Ia

Reaction steps A and C are carried out in general and specific terms under the conditions outlined for processes IA and IC.

Reaction step B:

The partial hydrolysis of the mixed diester IVa to give the monoester Va' is usually carried out at from $-40°$ to $20°$ C., preferably from $-20°$ to $0°$ C., in an inert organic solvent.

These processes are known in general terms and can be carried out under the conditions described in the literature.

If, in a synthesis of this type, a hydroxamyl chloride IIa is reacted with a β-keto ester III, it is also possible specifically to prepare the compound Ib where X is oxygen, $R^2$ is $CO_2R^5$ and $R^5$ is not hydrogen or methyl by the same route.

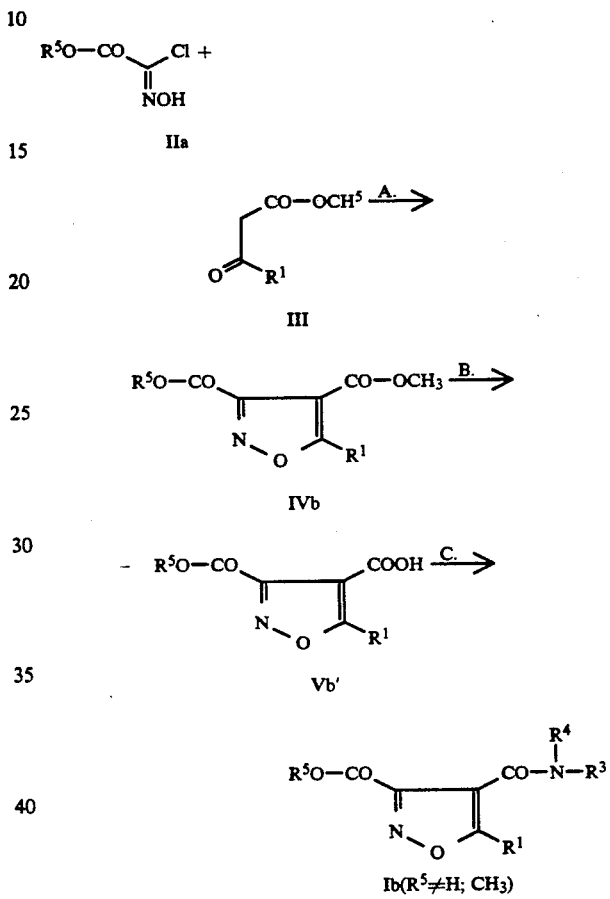

Ib($R^5 \neq H; CH_3$)

The last-mentioned process for the specific preparation of an isomer of the two carboxamides Ia and Ib is based on the possibility of selectively cleaving one ester group of the two different ester groups in a compound by using only one mole equivalent of hydrolyzing agent under mild reaction conditions.

Examples of suitable hydrolyzing agents are hydroxides of alkali metal cations in the case of unbranched alkyl esters, mineral acids in the case of α-branched alkyl esters, and hydrogen in the case of hydrogenolysis of benzyl and allyl esters.

3. A process for the preparation of a compound Ia or Ic in which $R^1$ is not hydrogen, and $R^2$ is carboxyl or formyl and $R^3$ is hydrogen:

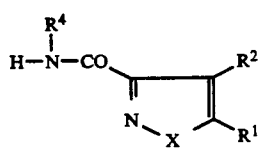

Ia($R^1 \neq H; R^2 = CO_2H, CHO$)

-continued

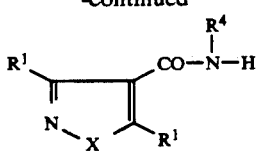

Ic(R$^1$≠H; R$^2$ = CO$_2$H, CHO)

These isomeric carboxamides Ia and Ic are obtained activating and amidating a carboxylic acid Vc or Vd under the conditions outlined under 1C, and subsequently reacting the resultant amide VIIa or VIIb in a conventional manner in the presence of a carboxylating or formylating agent.

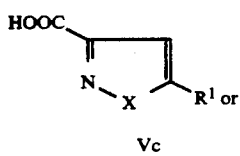

Vc

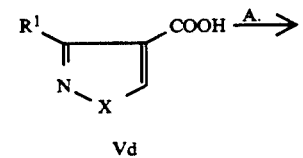

Vd

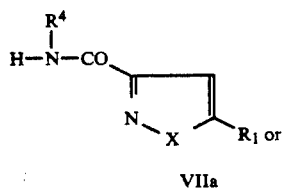

VIIa

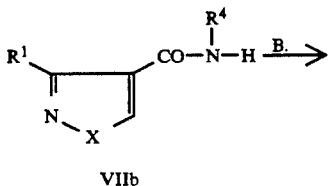

VIIb

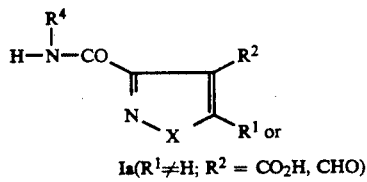

Ia(R$^1$≠H; R$^2$ = CO$_2$H, CHO)

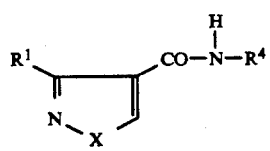

Ic(R$^1$≠H; R$^2$ = CO$_2$H, CHO)

Reaction step A is carried out in general and specific terms under the conditions described under point C in process 1.

Reaction step B:

The formylation or carboxylation of the carboxamide VIIa (X=O or S) or VIIb (X=S) is generally carried out at from −100° to 0° C., preferably from −80° to −20° C., and the formylation or carboxylation of the carboxamide VIIb (X=O) is advantageously carried out at < −80° C. The reaction is preferably carried out in an aprotic, polar, inert organic solvent with exclusion of moisture and in the presence of a base.

Particularly suitable formylating agents are dimethylformamide and N-formylmorpholine, and the preferred carboxylating agent is carbon dioxide.

Particularly suitable solvents are diethyl ether, tertbutyl methyl ether tetrahydrofuran and dioxane.

Preferred bases are alkali metal hydrocarbons, such as methyllithium, n-butyllithium, tert-butyllithium and phenyllithium.

The reaction is usually carried out by first adding from 2 to 2.5 mole equivalents of the dissolved base to a solution of the carboxamide VIIa or VIIb to produce a ring-metallated carboxamide derivative, which, on subsequent addition of the electrophilic formylating or carboxylating agent, reacts to form the desired product Ia or Ic.

The carboxylic acids Vc and Vd required for this process are known from the literature (Beilstein, main work and supplements 1-5, volume 27; R. W. Wiley, The Chemistry of Heterocyclic Compounds, Five- and Six-Membered Compounds with Nitrogen and Oxygen, Interscience Publishers, New York, London (1962), or can be prepared by methods known in general terms from the literature, for example by oxidizing the corresponding alcohol or aldehyde or by hydrolyzing the corresponding nitrile.

4. A process for the preparation of a compound of the formula Id in which R$^2$ is COOR$^5$ and R$^5$ is hydrogen or C$_1$-C$_6$-alkyl, by hydrolyzing a dialkyl isoxazole- or isothiazole-4,5-dicarboxylate X (R$^{5'}$=C$_1$-C$_6$-alkyl), converting the product into an acyl halide XII, and amidating the acyl chloride:

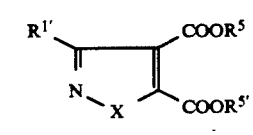

X (R$^5$ = R$^{5'}$ = C$_1$—C$_6$—Alkyl)

1) 1 equiv. of aqueous base
2) acid

XI

SOCl$_2$ or PHal$_3$, PHal$_5$

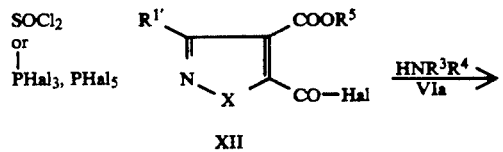

$\xrightarrow{\text{HNR}^3\text{R}^4}$ VIa

XII

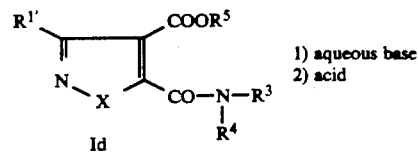

1) aqueous base
2) acid

Id

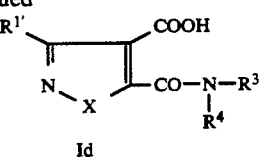

Id

Particularly suitable isoxazole- or isothiazole- 4,5-dicarboxylates X are lower alkyl esters ($R^5=R^{5'}=C_1-C_4$-alkyl), dimethyl and diethyl esters being particularly preferred.

The reaction is carried out by treating a dialkyl isoxazole- or isothiazole-4,5-dicarboxylate X in an organic solvent, eg. methanol or ethanol, at from about 0° to 80° C., preferably from 0° to 50° C., with in general about one equivalent of a strong base, eg. NaOH, KOH or Ca(OH)$_2$, in aqueous solution. When the reaction is complete, the mixture is cooled and acidified with a strong mineral acid, eg. hydrochloric acid or sulfuric acid. The resultant carboxylic acid XI can be isolated in a conventional manner, for example by suction filtration or by extraction with an organic solvent.

For conversion into the acyl halide XII, the carboxylic acid XI is reacted in a conventional manner with an inorganic acid halide, such as thionyl chloride, phosphorus trihalide or phosphorus pentahalide, the chlorides being preferred. The inorganic acid halide is expediently employed in an amount of from 1 to 5 mole equivalents, preferably from 1 to 2 mole equivalents. The reaction can be carried out without a solvent or in the presence of an inert organic solvent, eg. benzene or toluene, at from room temperature to the boiling point of the inorganic acid halide or the inert organic solvent. In some cases, the addition of a catalyst, such as dimethylformamide or 4-dimethylaminopyridine, may be advantageous. When the reaction is complete, the acyl halide XII can be isolated in a conventional manner, for example by removing the excess inorganic acid halide and organic solvent by distillation and subsequently distilling the acyl chloride XII at atmospheric pressure or reduced pressure.

The carboxamide of the formula Id in which $R^2$ is COOR$^5$ and $R^5$ is $C_1-C_6$-alkyl is obtained from the acyl halide XII by reaction with an amine VIa, the acyl halide generally being reacted in an inert organic solvent, such as dichloromethane, or an ether, such as diethyl ether or methyl tert-butyl ether, with an amine VIa, likewise dissolved in an organic solvent. The amine VIa is expediently employed in from 2- to 5-times the molar amount, preferably from 2- to 3-times the molar amount, in order to bind the hydrogen halide produced. The reaction can also be carried out in the presence of an auxiliary base, such as a tertiary amine, eg. triethylamine. In this case, from 1 to 1.5 mole equivalents of the amine VIa are sufficient. The reaction temperature can be, for example, from 0° to 50° C., preferably from 0° to 20° C. The reaction is generally complete after from 1 to 12 hours. The mixture can be worked up in a customary manner, for example by hydrolyzing with water and subsequently extracting of the product of the formula Id ($R^2$=COOR$^5$, $R^5=C_1-C_6$-alkyl) with an organic solvent and then evaporating the latter. The product of the formula Id ($R^2$=COOR$^5$, $R^5=C_1-C_6$-alkyl) can be purified, for example, by recrystallization or chromatography.

The acid amide Id ($R^2$=COOR$^5$, $R^5=C_1-C_6$-alkyl) can advantageously also be prepared from the carboxylic acid XI in one step, the carboxylic acid XI being reacted with an amine VIa at from 0° to 50° C., preferably from 5° to 25° C., in an inert solvent, such as dichloromethane, tetrahydrofuran, toluene or ethyl acetate, in the presence of a dehydrating agent, for example propanephosphonic anhydride (PPA) or dicyclohexylcarbodiimide (DCC).

The 4-alkoxycarbonylisoxazole-5-carboxamide or 4-alkoxycarbonylisothiazole-5-carboxamide Id ($R^2$=COOR$^5$ where $R^5=C_1-C_6$-alkyl) can be converted into the free carboxylic acid Id ($R^2$=COOH), for example, by hydrolysis using an aqueous base and subsequently neutralizing the product using a mineral acid. The reaction is carried out by treating the ester Id ($R^2$=COOR$^5$, $R^5=C_1-C_6$-alkyl) in an organic solvent, eg. methanol or ethanol, at from 0° to 80° C., preferably from 0° to 50° C., with a base, eg. NaOH, KOH or Ca(OH)$_2$. In general, from about 1 to 3 equivalents, preferably from 1 to 1.5 equivalents, of the strong base are employed in aqueous solution. When the reaction is complete, the mixture is acidified using a strong mineral acid, eg. hydrochloric acid or sulfuric acid, with cooling. The resultant carboxylic acid Id ($R^2$=COOH) can be isolated by suction filtration or by extraction with an organic solvent and evaporation of the latter. The product is further purified, for example, by recrystallization or chromatography.

5. A process for the synthesis of a dicarboxamide of the formula Ic in which $R^2$=CO—NR$^3$R$^4$ ($R^3$ and $R^4 \neq H$), by reacting the acid Id' with a primary amine VIa in the presence of a dehydrating agent:

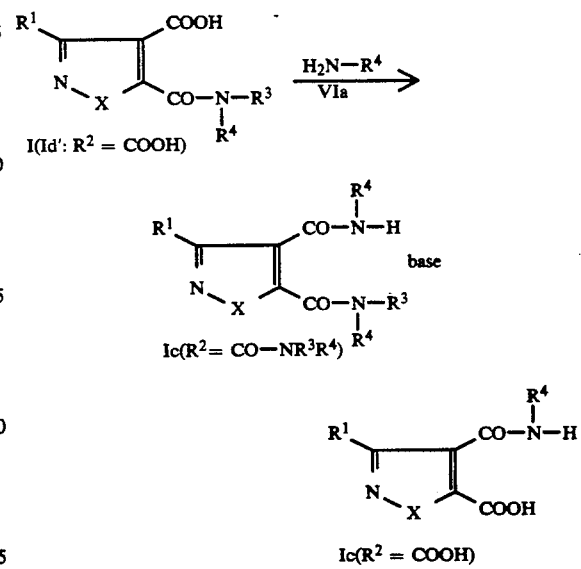

Examples of suitable dehydrating agents are propanephosphonic anhydride and dicyclohexylcarbodiimide. In general, the process is carried out at from −20° to 50° C., preferably from 20° to 40° C., in an inert organic solvent, such as dichloromethane or an ether, such as diethyl ether or methyl tert-butyl ether. The starting materials are reacted in approximately stoichiometric amounts. The mixture can be worked up in the cutomary manner, for example by hydrolysis using water, extraction of the product of the formula Ic ($R^2$=CO—NR$^3$R$^4$) with an organic solvent, and evaporation of the latter. The product of the formula Ic ($R^2$=CO—$NR^3R^4$) can be further purified, for example, by recrystallization or chromatography.

The resultant isoxazole-4,5-dicarboxamide of the formula Ic in which X is oxygen and $R^2$ is CO—$NR^3R^4$ ($R^3$ and $R^4 \neq H$) can be used to prepare the carboxylic acid Ic ($R^2$=COOH) by reaction with excess potassium tert-butoxide. This reaction is expediently carried out by treating the diamide Ic ($R^2$=CO—$NR^3R^4$) in an inert organic solvent, such as diethyl ether or tetrahydrofuran, at from 0° to 30° C., preferably at room temperature, with potassium tert-butoxide in water (ratio 3 to 6:1). The reaction is generally complete after from 1 to 12 hours. The free carboxylic acid Ic ($R^2$=COOH) can be isolated, after acidification using a mineral acid, either by suction filtration or by extraction with an organic solvent and evaporation of the latter. The acid Ic ($R^2$=COOH) can be further purified by either recrystallization or chromatography.

The isothiazole-4,5-dicarboxylates X (X=sulfur) required as starting material for this process are known (R. M. Paton, J. Stobie, R. M. Mortier, Phosphorus Sulfur, 15 (2), (1983), 137, or can be prepared by conventional methods.

The dialkyl isoxazole-4,5-dicarboxylates X (X=oxygen) required as starting material for this process are known from the literature [J. Org. Chem. 43, (1978), 3736; Chem. Pharm. Bull. 28, (1980), 3296; Tetrahedron 30, (1974), 1365] or can be prepared by methods which are known in general terms from the literature [cf., for example, DE-A 27 54 832, and Synthesis, (1982), 508], for example from the aldoxime XIII and the acetylenedicarboxylate XIV:

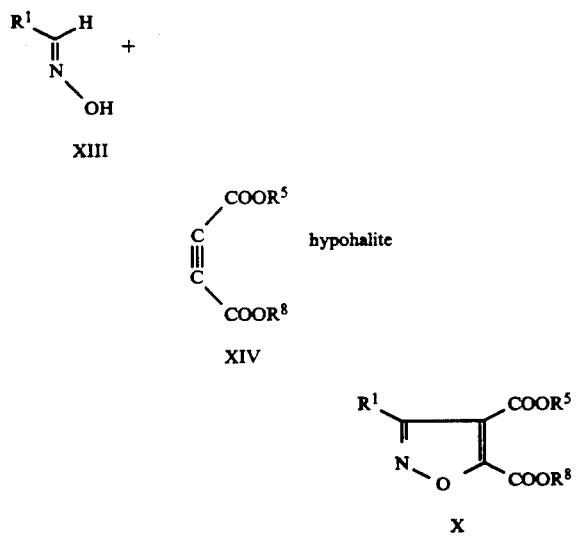

In this process, the aldoxime XIII is oxidized in the reaction medium by the hypohalite to give the corresponding nitrile oxide, which is a very reactive 1,3-dipole. This nitrile oxide is continuously scavenged, as it is produced, by the acetylene dicarboxylate XIV, likewise present in the reaction medium, in a 1,3-dipolar cycloaddition reaction with formation of the isoxazole compound X.

Expediently, equimolar amounts of the aldoxime XIII and of the acetylenedicarboxylate XIV are reacted with the hypohalite, which can be added to the reaction mixture in a stoichiometric amount. However, it is usually metered into the reaction batch in a slight excess, up to a two-fold excess. For technical reasons, it may be advantageous to limit the conversion by using sub-stoichiometric amounts of hypohalite, from about 50 to 90 mol-% per mole of XIII. It is also possible to use sub- or super-stoichiometric amounts of the reactants XIII and XIV.

The hypohalites used are generally hypobromites or hypochlorites, of which the latter are preferred. For this purpose, aqueous solutions of hypochlorous or hypobromous acid may be employed, but alkali metal or alkaline earth metal hypochlorites or hypobromites, for example sodium hypochlorite, potassium hypochlorite, calcium hypochlorite, magnesium hypochlorite, strontium hypochlorite, barium hypochlorite or the corresponding hypobromides, are preferred. Particular preference is given to sodium hypochlorite, potassium hypochlorite and calcium hypochlorite, in the form of their commercially available, aqueous solutions.

Examples of suitable solvents for the process are alcohols, such as methanol, ethanol, propanol and isopropanol, ketones, such as acetone and methyl ethyl ketone, ethers, such as diethyl ether, methyl tert-butyl ether, tetrahydrofuran and dioxane, hydrocarbons, such as pentane, hexane, cyclohexane, petroleum ether, white oils and ligroin, halogenated aliphatic hydrocarbons, such as methylene chloride, chloroform, carbon tetrachloride, dichlorethane, trichloroethane, tetrachloroethane and perchloroethane, aromatic compounds, such as benzene, toluene, xylenes and chlorobenzenes, esters, such as ethyl acetate, and dimethylformamide, N-methylpyrrolidone, dimethyl sulfoxide, sulfolane, etc.

The temperature at which the reaction is carried out can be varied within broad limits. In general, it takes place even at −15° C. and lower, and the upper limit is in principle set only by the boiling point of the solvent used, since the reaction is expediently carried out at atmospheric pressure. The preferred temperature range is from 0° to 40° C. The reaction can also be carried out under superatmospheric pressure, in particular under autogenous pressure, but atmospheric pressure is preferred.

The aldoximes XIII required for this process are either known or can be prepared in a conventional manner (eg. Houben-Weyl, Methoden der organischen Chemie, Vol. 10/4, pages 55 to 56, Thieme Verlag, Stuttgart, 1968) by reacting the corresponding aldehydes with hydroxylamine. The aldoximes XIII can of course be used either in the form of their E- or Z-isomers or as mixtures of these. The acetylenedicarboxylates are commercially available or can be prepared by conventional methods (eg. Organic Syntheses Coll. Vol. 4, page 329).

6. A process for the preparation of compounds Ia and Ib, in which $R^2$ is carboxyl and X is sulfur:

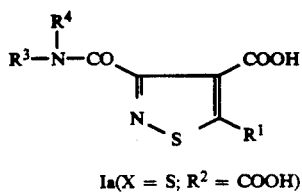

Ia(X = S; $R^2$ = COOH)

-continued

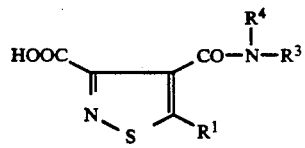

Ib(X = S; R² = COOH)

These carboxamides Ia and Ib are particularly advantageously obtained by reacting an isothiazoledicarboxylic anhydride VIII in a conventional manner with an amine VIa, and separating the resultant mixture of isomers Ia and Ib into the individual components.

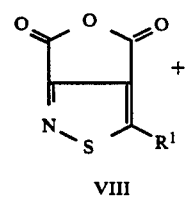

VIII

HNR³R⁴ ⟶
VIa

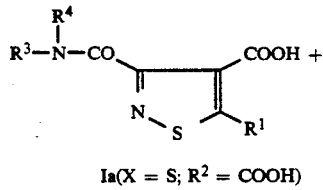

Ia(X = S; R² = COOH)

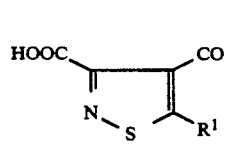

Ib(X = S; R² = COOH)

The reaction is usually carried out at from −10° to 50° C., preferably from 0° to 30° C., in an inert, aprotic, polar organic solvent.

Particularly preferred solvents are halogenated hydrocarbons, such as methylene chloride, and ethers, such as diethyl ether, tert-butyl methyl ether and tetrahydrofuran.

The amine VIa is generally employed in an equimolar amount or in an excess, preferably in an amount of from 1 to 1.2 mol equivalents, based on VIII.

In this process, the isomeric carboxamides of the formulae Ia and Ib ($R_2$=COOH) are produced in different amounts. The isomer mixture is resolved either by fractional crystallization or by chromatography.

The isothiazoledicarboxylic anhydrides VIII required for this process are known or can be prepared by conventional methods (Beilstein, Main Work and Supplements 1-5, Volume 27).

7. A process for the preparation of a compound Ia, Ib, Ic or Id, in which R² is CO₂H:

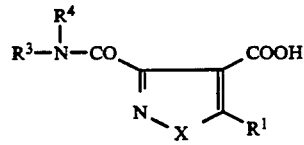
Ia

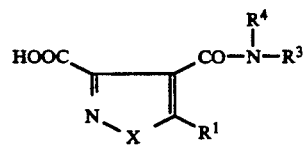
Ib

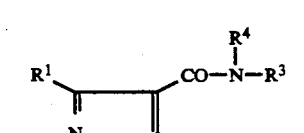
Ic

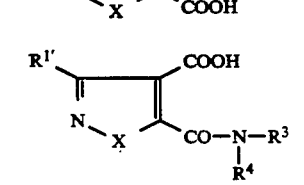
Id

These compounds Ia, Ib, Ic and Id are obtained by hydrolyzing the corresponding ester Ia, Ib, Ic or Id in which R² is CO₂R⁵ and R⁵ is C₁-C₄-alkyl in a conventional manner in the presence of an aqueous base.

This ester hydrolysis is carried out under the general and specific conditions outlined for process 2 under point B.

8. A process for the preparation of compounds Ia, Ib, Ic and Id in which R² is COYR⁵ or CONR⁶R⁷ (shown as an example for the carboxamide Ia):

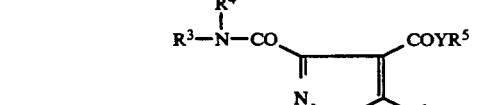

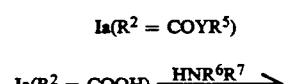

Ia(R² = COYR⁵)

Ia(R² = COOH) $\xrightarrow[\text{VIb}]{\text{HNR}^6\text{R}^7}$

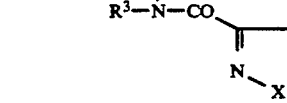

(R² = CONR⁶R⁷)

Expediently, a carboxylic acid Ia, Ib, Ic or Id (R²=COOH) is reacted with an alcohol or thiol IX or with an amine VIb in the presence of a dehydrating agent, for example propane phosphonic anhydride (PPA) or dicyclohexylcarbodiimide (DCC), at from −20° to 50° C., preferably from 0° to 40° C., in particular from 20° to 30° C.

All the starting compounds are advantageously employed in an approximately stoichiometric ratio, but an excess of one or other component, approximately up to 10 mol-%, may also be advisable in some cases.

Expedient solvents are hydrocarbons, such as toluene and o-, m- and p-xylene, halogenated hydrocarbons, such as dichloromethane, and ethers, such as diethyl ether, tert-butyl methyl ether and tetrahydrofuran.

A variant of the process comprises activating the carboxylic acid Ia, Ib, Ic or Id ($R^2$=COOH) as described for process 1C, and subsequently esterifying or amidating the product without using a dehydrating agent.

The process is normally carried out at atmospheric pressure.

The amines VIb are known or can be prepared by conventional processes Some of the alcohols and thiols HY—$R^5$ are known. If $R^5$ is —$CR^{10}$=N—$R^{11}$-substituted $C_1$-$C_6$-alkyl (iminoalcohols XVI), these alcohols and thiols are novel; however, they can be prepared by one of the following known processes (shown as an example for Y=O and $R^5$=—$CH_2$-$CR^{10}$=N—$R^{11}$ where $R^{10}$=H and $R^{11}$=$C_2H_5$):

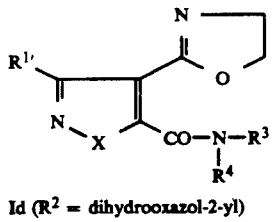

Id ($R^2$ = dihydrooxazol-2-yl)

The reaction is carried out by reacting the compound at from 0° to 180° C., preferably under reflux temperature of the mixture used, with an aminoalcohol XV, if desired in the presence of an inert solvent. The ester or carboxylic acid and the aminoalcohol XV are employed in a ratio of from 1:1 to 1:2.5, preferably from 1:1 to 1:1.5.

The solvents expediently used are halogenated hydrocarbons, such as chlorobenzene and 1,2-dichlorobenzene, ethers, eg. methyl tert-butyl ether, 1,2-dimethoxyethane, diethylene glycol dimethyl ether, tetrahydrofuran and dioxane, alcohols, such as methanol, ethanol, propanol and ethylene glycol, dipolar aprotic solvents, eg. acetonitrile, dimethylformamide, dimethylac-

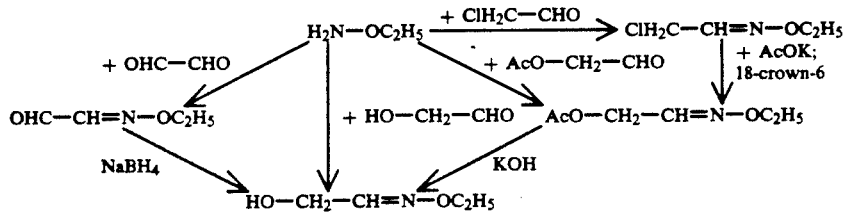

(E/Z isomer mixture)

b.p. (30 mbar) = 72–76° C.
Ac = $CH_3CO$
$n_D^{20}$ = 1.4340

The following alcohols, for example, were prepared by the process mentioned:
HO—$CH_2$—CH=N—$OCH_3$
HO—$CH_2$—C($CH_3$)=N—$OCH_3$
HO—$CH_2$CH=N—$OCH_2$—CH=CHCl
HO—$CH_2$—CH=N—$OCH_2$—$C_6H_5$
HO—$CH_2$—C($CH_3$)=N—$OC_2H_5$
HO—$CH_2$—CH=N—$OCH_2$—CH=$CH_2$
HO—$CH_2$—C($CH_3$)=N—$OCH_2$—$C_6H_5$
HO—$CH_2$—C($CH_3$)=N—$OCH_2$—CH=$CH_2$ 9. A process for the preparation of a compound Ia, Ib, Ic or Id in which $R^2$ is 4,5-dihydrooxazol-2-yl, by the conventional reaction of a carboxamide Ia, Ib, Ic or Id where $R^2$ is COOH or $COOR^5$ ($R^5$=unsubstituted or substituted $C_1$-$C_4$-alkyl, as indicated under the radicals $R^5$), with an aminoalcohol of the formula XV [cf. Wehrmeister, J. Org. Chem. 26, (1961), 3821]:

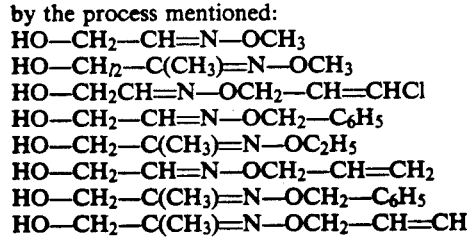

Id ($R^2$ = CO—$OR^5$)

etamide, dimethyl sulfoxide, N-methylpyrrolidone, 1,3-dimethyltetrahydro-2(1H)-pyrimidinone and 1,3-dimethylimidazolin-2-one, or aromatic compounds, eg. benzene, toluene and xylene. The concentration of the starting materials in the solvent is generally from 0.1 to 5.0 mol/l, preferably from 0.2 to 2.0 mol/l.

The reaction is generally complete after 14 hours; the carboxamide Ia, Ib, Ic or Id (where $R^2$=4,5-dihydrooxazol-2-yl) is then precipitated, if necessary, by adding water, and filtered off with suction or extracted with an organic solvent, and purified by customary standard methods, such as recrystallization or chromatography.

The process is generally carried out at atmospheric pressure or under the autogenous pressure of the particular solvent.

10. A process for the preparation of a compound Ia; Ib, Ic or Id in which $R^2$ is formyl:

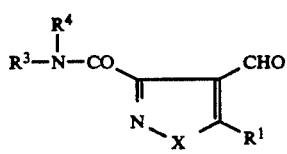

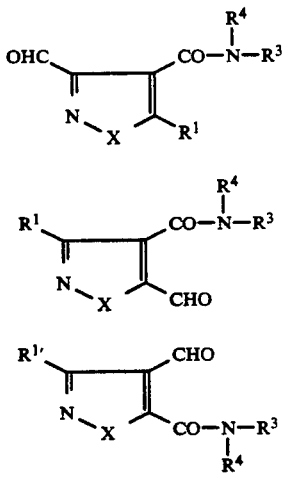

The compound Ia, Ib, Ic or Id is obtained, for example, by activating a corresponding carboxamide of the formula Ia, Ib, Ic or Id where $R^2$ is $CO_2H$, under the conditions outlined in the case of process 1, and reducing the resultant activated form of the carboxylic acid in a conventional manner.

The carboxylic acid is preferably converted into the corresponding chloride, which is reduced at from $-100°$ to $0°$ C., in particular from $-80°$ to $-50°$ C., using a complex hydride, such as, in particular, lithium tri-t-butoxyaluminum hydride. Particularly preferred solvents in this case are ethers, such as dimethyl ether, diethyl ether, tetrahydrofuran, 1,2-dimethoxyethane, diethylene glycol dimethyl ether and dioxane (J. Am. Chem. Soc. 80, (1958), J. Am. Chem. Soc. 80, (1958), 5377).

11. A compound of the formula Ia, Ib, Ic or Id in which $R^1$ or $R^{1'}$ is epoxidized $C_2-C_6$-alkenyl, which may be monosubstituted, disubstituted or trisubstituted by halogen, $C_1-C_3$-alkoxy and/or monosubstituted by cyclopropyl or unsubstituted or substituted phenyl as mentioned under $R^1$, is obtained, for example, by epoxidizing a carboxamide of the formula Ia, Ib, Ic or Id where $R^1$ or $R^{1'}$ is $C_2-C_6$-alkenyl, which may carry the abovementioned substituents, in a conventional manner using a suitable oxidant (eg. J. March, Advanced Organic Chemistry, Third Edition, John Wiley and Sons, 1985, pp. 735ff.).

In addition to processes 1-11 outlined above for the preparation of compounds Ia, Ib, Ic and Id, there are further possible syntheses, which are given in the following literature:

Beilstein, Main Work and supplements 1-5, Volume 27; R. W. Wiley, The Chemistry of Heterocyclic Compounds, Five- and Six-Membered Compounds with Nitrogen and Oxygen, Interscience Publishers, New York, London (1962); A. R. Katritzky, C. W. Rees, Comprehensive Heterocyclic Chemistry, Vol. 6, Five-membered Rings with Two or More Oxygen, Sulfur or Nitrogen Atoms, Pergamon Press, 1984; J. March, Advanced Organic Chemistry, Third Edition, John Wiley and Sons, 1985; Houben-Weyl, Methoden der organischen Chemie, 4th Edition, Thieme Verlag, Volumes IV, VI, VII, VIII, X.

In detail, these substituents in compounds Ia, Ib, Ic and Id have the following meanings:

$R^1$ is hydrogen;

halogen, such as fluorine, chlorine, bromine or iodine, in particular fluorine or chlorine;

linear or branched $C_1-C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl-, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, in particular methyl, ethyl, propyl, 1-methylethyl or 1,1-dimethylethyl, which may carry from one to five halogen atoms, such as fluorine, chlorine, bromine or iodine, in particular fluorine or chlorine, and/or a cyano radical and/or up to two of the following radicals:

$C_1-C_4$-alkoxy, such as methoxy, ethoxy, propoxy, 1-methylethoxy, butoxy, 1-methylpropoxy, 2-methylpropoxy and 1,1-dimethylethoxy, in particular methoxy, ethoxy, 1-methylethoxy and 1,1-dimethylethoxy;

partially or fully halognated $C_1-C_4$-alkoxy, such as difluoromethoxy, trifluormethoxy, chlorodifluoromethoxy,dichlorofluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy and pentafluoroethoxy, in particular trifluoromethoxy and pentafluoroethoxy;

$C_1-C_4$-alkylthio, such as methylthio, ethylthio, propylthio, 1-methylethylthio, n-butylthio, 1-methylprophylthio, 2-methylpropylthio and 1,1-dimethylethylthio, in particular methylthio and ethylthio;

partially or fully halogenated $C_1-C_4$-alkylthio, such as difluoromethylthio, trifluoromethylthio, chlorodifluoromethylthio, 1-fluoroethylthio, 2-fluoroethylthio, 2,2-difluoroethylthio, 2,2,2-trifluoroethylthio, 2-chloro-2,2-difluoroethylthio,2,2-dichloro-2-fluoroethylthio, 2,2,2-trichloroethylthio and pentafluoroethylthio, in particular trifluoromethylthio and pentafluoroethylthio;

$C_1-C_4$-alkoxy as mentioned above, in particular methoxy or ethoxy;

partially or fully halogenated $C_1-C_4$-alkoxy as mentioned above, in particular trifluoromethoxy, trichloromethoxy or pentafluoroethoxy;

$C_1-C_4$-alkylthio as mentioned above, in particular methylthio or ethylthio;

partially or fully halogenated $C_1-C_4$-alkylthio as mentioned above, in particular difluoromethylthio, trifluoromethylthio or pentafluoroethylthio;

benzyl which may be monosubstituted, disubstituted or trisubstituted by alkyl having from 1 to 4 carbon atoms as mentioned above, in particular methyl, ethyl or 1-methylethyl; haloalkyl zs mentioned above, in particular trifluoromethyl or chlorodifluoromethyl; alkoxy as mentioned above, in particular methoxy or ethoxy; haloalkoxy as mentioned above, in particular trifluoromethoxy, trichloromethoxy or pentafluoroethoxy; alkylthio as mentioned above, in particular methylthio or ethylthio; haloalkylthio as mentioned above, in particular difluoromethylthio, trifluoromethylthio or pentafluoromethylthio; halogen as mentioned above, in particular fluorine or chlorine; cyano or nitro;

phenyl which may also carry from one to three of the following radicals: cyano; nitro; halogen, such as fluorine, chlorine, bromine or iodine, in particular fluorine or chlorine; $C_1$–$C_6$-alkyl as mentioned above, in particular methyl, ethyl or 1-methylethyl; partially or fully halogenated $C_1$–$C_6$-alkyl as mentioned above, in particular trifluoromethyl or chlorodifluoromethyl; $C_1$–$C_6$-alkoxy as mentioned above, in particular methoxy or ethoxy; partially or fully halogenated $C_1$–$C_6$-alkoxy as mentioned above, in particular trifluoromethoxy, trichloromethoxy or pentafluoroethoxy; $C_1$–$C_4$-alkylthio as mentioned above, in particular methylthio or ethylthio and/or partially or fully halogenated $C_1$–$C_6$-alkylthio as mentioned above, in particular difluoromethylthio, trifluoromethylthio or pentafluoromethylthio;

$C_3$–$C_8$-cycloalkyl-$C_1$–$C_6$-alkyl, preferably $C_3$–$C_6$-cycloalkyl-$C_1$–$C_4$-alkyl, such as cyclopropylmethyl, cyclopentylmethyl, cyclohexylmethyl, 1-cyclopropylethyl, 2-cyclopropylethyl, 1-cyclopropyl-1-methylethyl, 2-cyclopropyl-1-methylethyl or 4-cyclohexyl-n-butyl;

$C_2$–$C_6$-alkenyl, whose double bond may be epoxidized, preferably $C_2$–$C_4$-alkenyl, such as ethenyl, prop-2-en-1-yl, 1-methylethenyl, but-2-en-1-yl or 1-methylprop-2-en-1-yl, which may be monosubstituted, disubstituted or trisubstituted by halogen, such as fluorine, chlorine, bromine or iodine, $C_1$–$C_3$-alkoxy, such as methoxy, ethoxy or isopropoxy, and/or monosubstituted by cyclopropyl or phenyl, it being possible for the phenyl radical to itself carry from one to three of the following groups: cyano, nitro, alkyl as mentioned above, in particular methyl, ethyl or 1-methylethyl; haloalkyl as mentioned above, in particular trifluoromethyl or chlorodifluoromethyl; alkoxy as mentioned above, in particular methoxy or ethoxy; haloalkoxy as mentioned above, in particular trifluoromethoxy, trichloromethoxy or pentafluoroethoxy; alkylthio as mentioned above, in particular methylthio or ethylthio; partially or fully halogenated alkylthio as mentioned above, in particular difluoromethylthio, trifluoromethylthio or pentafluoromethylthio or halogen as mentioned above, in particular fluorine or chlorine;

$C_2$–$C_6$-alkynyl, preferably $C_2$–$C_4$-alkynyl, such as ethynyl, propyn-1-yl, 1-methyl-2-propyn-yl or n-butynyl, which may be monosubstituted, disubstituted or trisubstituted by halogen, such as fluorine, chlorine, bromine or iodine, $C_1$–$C_3$-alkoxy, such as methoxy or isopropoxy, and/or monosubstituted by cyclopropyl or phenyl, it being possible for the phenyl radical to itself carry from one to three of the following groups: cyano, nitro, alkyl as mentioned above, in particular methyl, ethyl or 1-methylethyl; haloalkyl as mentioned above, in particular trifluoromethyl or chlorodifluoromethyl; alkoxy as mentioned above, in particular methoxy or ethoxy; haloalkoxy as mentioned above, in particular trifluoromethoxy, trichloromethoxy or pentafluoroethoxy; alkylthio as mentioned above, in particular methylthio or ethylthio; partially or fully halogenated alkylthio as mentioned above, in particular difluoromethylthio, trifluoromethylthio or pentafluoromethylthio or halogen as mentioned above, in particular fluorine or chlorine;

$C_3$–$C_8$-cycloalkyl, such as cyclopropyl, cyclobutyl, cyclopentyl, cyclohexyl, cycloheptyl or cyclooctyl, in particular cyclopropyl, cyclopentyl or cyclohexyl, or $C_3$–$C_6$-cycloalkenyl, in particular $C_5$–$C_6$-cycloalkenyl, such as cyclohexen-1-yl, it being possible for the ring to also be monosubstituted, disubstituted or trisubstituted by $C_1$–$C_4$-alkyl as mentioned above, in particular methyl or ethyl; or by halogen, such as fluorine, chlorine, bromine or iodine, in particular fluorine or chlorine;

phenoxy or phenylthio, it being possible for both groups to be monosubstituted, disubstituted or trisubstituted by $C_1$–$C_4$-alkyl as mentioned above, in particular methyl, ethyl or 1-methylethyl; partially or fully halogenated $C_1$–$C_4$-alkyl as mentioned above, in particular trifluoromethyl or chlorodifluoromethyl; $C_1$–$C_4$-alkoxy as mentioned above, in particular methoxy or ethoxy; partially or fully halogenated $C_1$–$C_4$-alkoxy as mentioned above, in particular trifluoromethoxy, trichloromethoxy or pentafluoroethoxy; $C_1$–$C_4$-alkylthio as mentioned above, in particular methylthio or ethylthio; partially or fully halogenated $C_1$–$C_4$-alkylthio as mentioned above, in particular difluoromethylthio, trifluoromethylthio or pentafluoromethylthio; halogen as mentioned above, in particular fluorine or chlorine; cyano or nitro;

a 5- or 6-membered saturated or aromatic heterocyclic radical containing one or two heteroatoms selected from the group comprising oxygen, sulfur and nitrogen, such as 2-tetrahydrofuranyl, 3-tetrahydrofuranyl, 2-tetrahydrothienyl, 3-tetrahydrothienyl, 2-tetrahydropyranyl, 3-tetrahydropyranyl, 4-tetrahydropyranyl, 2-furanyl, 3-furanyl, 2-thienyl, 3-thienyl, 3-isoxazolyl, 4-isoxazolyl, 5-isoxazolyl, 3-isothiazolyl, 4-isothiazolyl, 5-isothiazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 2-pyrrolyl, 3-pyrrolyl, 3-pyrazolyl, 4-pyrazolyl, 5-pyrazolyl, 2-pyridyl, 3-pyridyl and 4-pyridyl, which may carry one or two of the following substituents: alkyl as mentioned above, in particular methyl; halogen as mentioned above, in particular fluorine or chlorine; alkoxy as mentioned above, in particular methoxy or ethoxy; or alkoxycarbonyl, such as methoxycarbonyl or ethoxycarbonyl, in particular methoxycarbonyl;

$R^{1'}$ is $C_3$–$C_8$-cycloalkyl-$C_1$–$C_6$-alkyl, preferably $C_3$–$C_6$-cycloalkyl-$C_1$–$C_4$-alkyl, such as cyclopropylmethyl, cyclopentylmethyl, cyclohexylmethyl, 1-cyclopropylethyl, 2-cyclopropylethyl, 1-cyclopropyl-1-methylethyl, 2-cyclopropyl-1-methylethyl or 4-cyclohexyl-n-butyl;

$C_2$–$C_8$-alkenyl, whose double bond may be epoxidized, preferably $C_2$–$C_4$-alkenyl, such as ethenyl, prop-2-en-1-yl and isopropenyl, which may be monosubstituted, disubstituted or trisubstituted by halogen, such as fluorine, chlorine, bromine or iodine, $C_1$–$C_3$-alkoxy, such as methoxy, ethoxy or isopropoxy, and/or monosubstituted by cyclopropyl or phenyl, it being possible for the phenyl radical to itself carry from one to three of the following groups: cyano, nitro, alkyl as mentioned above, in particular methyl, ethyl or 1-methylethyl; haloalkyl as mentioned above, in particular trifluoromethyl or chlorodifluoromethyl; alkoxy as mentioned above, in particular methoxy or ethoxy; haloalkoxy as mentioned above, in particular trifluoromethoxy, trichloromethoxy or pentafluoroethoxy; alkylthio as mentioned above, in particular methylthio or ethylthio; partially or fully halogenated alkylthio as mentioned above, in particular difluoromethylthio, trifluoromethylthio or pentafluoromethylthio or halogen as mentioned above, in particular fluorine or chlorine;

$C_2$–$C_6$-alkynyl, preferably $C_2$–$C_4$-alkynyl, such as ethynyl, propyn-1-yl or n-butynyl, which may be monosubstituted, disubstituted or trisubstituted by halogen, such as fluorine, chlorine, bromine or iodine, in particular fluorine or chlorine, $C_1$–$C_3$-alkoxy, such as methoxy or isopropoxy, and/or monosubstituted by cyclopropyl or phenyl, it being possible for the phenyl radical to itself carry from one to three of the following groups: cyano, nitro, alkyl as mentioned above, in particular methyl, ethyl or 1-methylethyl; haloalkyl as mentioned above, in particular trifluoromethyl or chlorodifluoromethyl; alkoxy as mentioned above, in particular methoxy or ethoxy; haloalkoxy as mentioned above, in particular trifluoromethoxy, trichloromethoxy or pentafluoroethoxy; alkylthio as mentioned above, in particular methylthio or ethylthio; partially or fully halogenated alkylthio as mentioned above, in particular difluoromethylthio, trifluoromethylthio or pentafluoromethylthio or halogen as mentioned above, in particular fluorine or chlorine;

$C_3$–$C_6$-cycloalkenyl, preferably $C_5$–$C_6$-cycloalkenyl, which may be monosubstited, disubstituted or trisubstituted by halogen, such as fluorine, chlorine, bromine or iodine, in particular fluorine or chlorine, or $C_1$–$C_4$-alkyl, such as methyl, ethyl or tert-butyl;

$R^2$ is
formyl;
4,5-dihydrooxazol-2-yl-;
$COYR^5$ or $CONR^6R^7$, where
$R^5$ is
hydrogen;
$C_1$–$C_6$-alkyl, preferably $C_1$–$C_4$-alkyl, such as methyl, ethyl or tert-butyl, which may carry from one to five halogen atoms, such as fluorine, chlorine, bromine or iodine, in particular fluorine or chlorine, and/or up to three hydroxyl and/or $C_1$–$C_4$-alkoxy groups, such as methoxy, ethoxy, n-propoxy, isopropoxy, n-butoxy or tert-butoxy, and/or one of the following radicals: cyano,
$C_1$–$C_4$-alkoxy, in particular methoxyethoxy, ethoxyethoxy or propoxyethoxy, $C_1$–$C_3$-alkylthio, in particular methylthio or ethylthio,
$C_1$–$C_3$-alkylamino such as methylamino, ethylamino or isopropylamino,
di($C_1$–$C_3$)-alkylamino such as dimethylamino, diethylamino, dipropylamino, di(1-methylethyl)amino or methylethylamino,
$C_3$–$C_6$-cycloalkylamino or di($C_3$–$C_6$)-cycloalkylamino such as cyclopropylamino or dicyclopropylamino, ylsulfinyl such as methylsulfinyl,
trimethylsilyl,
$C_1$–$C_3$-alkylsulfinyl such as methylsulfinyl, 1-methylethylsulfinyl or n-propylsulfinyl,
$C_1$–$C_3$-alkylsulfonyl such as methylsulfonyl, ethylsulfonyl or isopropylsulfonyl,
carboxyl,
$C_1$–$C_3$-alkoxycarbonyl such as methoxycarbonyl or isopropoxycarbonyl,
$C_1$–$C_3$-alkoxycarbonyl-$C_1$–$C_3$-alkoxy such as methoxycarbonylmethoxy,
$C_1$–$C_3$-alkoxycarbonyl-$C_1$–$C_3$-alkoxy-$C_1$–$C_3$-alkoxycarbonyl such as methoxycarbonylethoxymethoxycarbonyl,
di($C_1$–$C_3$)-alkylaminocarbonyl such as dimethylaminocarbonyl, methylethylaminocarbonyl or diisopropylaminocarbonyl,
di($C_1$–$C_3$)-alkoxyphosphonyl such as dimethoxyphosphonyl or diisopropoxyphosphonyl,
$C_1$–$C_6$-alkaneiminoxy such as 2-propaneiminoxy or $C_5$–$C_6$-cycloalkaneiminoxy, such as cyclopentaneiminoxy or cyclohexaneiminoxy
N-phthalimido, N-succinimido, benzyloxy or benzoyl, it being possible for these cyclic radicals to carry from one to three of the following groups: halogen as mentioned above, in particular fluorine or chlorine, $C_1$–$C_3$-alkyl, such as methyl, ethyl or isopropyl, in particular methyl, or $C_1$–$C_3$-alkoxy, such as methoxy, ethoxy or isopropoxy, in particular methoxy;
a 5- or 6-membered, saturated, heterocyclic radical or a 5- or 6-membered heteroaromatic radical, in each case having from one to three heteroatoms selected from the group comprising oxygen, sulfur and nitrogen, where two oxygen or sulfur atoms or one oxygen and one sulfur atom must not be directly adjacent, in particular tetrahydrofuran-2-yl, tetrahydrofuran-3-yl, tetrahydrothien-2-yl, tetrahydrothien-3-yl,tetrahydropyran-2-yl, tetrahydropyran-3-yl,tetrahydropyran-4-yl, pyrrolidin-2-yl, pyrrolidin-3-yl, furan-2-yl, furan-3-yl, thien-2-yl, thien-3-yl, pyrrol-2-yl, pyrrol-3-yl, isoxazol-3-yl, isoxazol-4-yl, isoxazol-5-yl, isothiazol-3-yl, isothiazol-4-yl, isothiazol-5-yl, oxazol-2-yl, oxazol-4-yl, oxazol-5-yl, thiazol-2-yl, thiazol-4-yl, thiazol-5-yl, imidazol-2-yl, imidazol-4-yl, imidaxol-5-yl, pyrazol-1-yl, pyrazol-3-yl, pyrazol-4-yl, pyrazol-5-yl, 1,2,3-triazol-1-yl, 1,2,3-triazol-4-yl, 1,2,3-triazol-5-yl, 1,2,4-triazol-1-yl, 1,2,4-triazol-3-yl, 1,2,4-triazol-5-yl, 1,2,3-thiadiazol-4-yl, 1,2,3-thiadiazol-5-yl, 1,2,4-thiadiazol-3-yl, 1,2,4-thiadazol-5-yl, 1,2,5-thiadiazol-3-yl, 1,2,5-thiadiazol-4-yl, 1,3,4-thiadiazol-2-yl, 1,3,4-thiadiazol-5-yl, 1,2,3-oxadiazol-3-yl, 1,2,3-oxadiazol-5-yl, 1,2,4-oxadiazol-3-yl, 1,2,4-oxadiazol-5-yl, 1,2,5-oxadiazol-3-yl, 1,2,5- oxadiazol-4-yl, 1,3,4-oxadiazol-2-yl, 1,3,4-oxadiazol-5-yl, pyrid-2-yl, pyrid-3-yl, pyrid-4-yl, pyrimid-2-yl,pyrimid-4-yl or pyrimid-5-yl, it being possible for the heterocyclic rings to also carry one or two of the following substituents: halogen, such as fluorine, chlorine, bromine or iodine, in particular chlorine or bromine, $C_1$–$C_3$-alkyl, such as methyl, ethyl, n-propyl or isopropyl, $C_1$–$C_3$-alkoxy, such as methoxy, ethoxy, n-propoxy or isopropoxy, and/or $C_1$–$C_3$-alkoxycarbonyl, such as methoxycarbonyl, ethoxycarbonyl or isopropoxycarbonyl;

phenyl, which may also carry from one to three of the following substituents: halogen, such as fluorine, chlorine, bromine or iodine, in particular fluorine or chlorine, nitro, cyano, $C_1$–$C_3$-alkyl, such as methyl or isopropyl, partially or fully halogenated $C_1$–$C_3$-alkyl, such as trifluoromethyl, 1,1,2,2-tetrafluoroethyl or trichloromethyl, $C_1$–$C_3$-alkoxy, such as methoxy or isopropoxy, and/or partially or fully halogenated $C_1$–$C_3$-alkoxy, in particular trifluoromethoxy;

—$CR^{10}$=N—$R^{11}$ where $R^{10}$ is hydrogen or linear or branched $C_1$–$C_6$-alkyl, in particular $C_1$–$C_4$-alkyl, such as methyl, ethyl, n-propyl, isopropyl, n-butyl or tert-butyl;

$R^{11}$ is $C_1$–$C_6$-alkoxy, $C_3$–$C_6$-alkenyloxy or $C_3$–$C_6$-alkynyloxy, in particular $C_1$–$C_4$-alkoxy, such as methoxy, ethoxy, n-propoxy, isopropoxy, n-butoxy or tert butoxy, and prop-2-enyloxy, but-2-enyloxy, prop-2-ynyloxy or but-2-ynyloxy, it being possible for these substiutents to also carry from one to three halogen atoms, such as fluorine, chlorine, bromine or iodine, in particular fluorine or chlorine, and/or phenyl which may be unsubstituted or monosubstituted, disubstituted or trisubstituted by halogen, as mentioned above, nitro, cyano, $C_1$–$C_3$-alkyl, such as methyl, ethyl, n-propyl or isopropyl, and/or $C_1$–$C_3$-alkoxy, such as methoxy, ethoxy, n-propoxy or isopropoxy; phenoxy, which may also carry from one to three of the following substituents: nitro, cyano, halogen as mentioned above, $C_1$–$C_3$-alkyl as mentioned above, and/or $C_1$–$C_3$-alkoxy as mentioned above;

linear or branched $C_1$–$C_5$-alkylamino, di($C_1$–$C_6$)-alkylamino or phenylamino, it being possible for the aromatic ring to additionally be monosubstituted, disubstituted or trisubstitued by nitro, cyano, halogen as mentioned above, $C_1$–$C_3$-alkyl as mentioned above, and/or $C_1$–$C_3$-alkoxy as mentioned above;

$C_3$–$C_8$-cycloalkyl, preferably $C_3$–$C_6$-cycloalkyl, such as cyclopropyl, cyclopentyl or cyclohexyl;

$C_3$–$C_6$-alkenyl, preferably $C_3$–$C_4$-alkenyl, such as 2-propenyl or 2-butenyl, $C_5$–$C_6$-cycloalkenyl, such as 2-cyclopentenyl or 2-cyclohexenyl, $C_3$–$C_6$-alkynyl, preferably $C_3$–$C_4$-alkynyl, such as 2-propynyl, 2-butynyl or 3-butynyl, it being possible for the 3 last-mentioned groups to carry one of the following radicals: hydroxyl, halogen, such as fluorine, chlorine, bromine or iodine, $C_1$–$C_4$-alkoxy, such as methoxy or tert-butoxy, or phenyl, which may itself carry from one to three of the following groups: halogen, such as fluorine, chlorine or bromine, nitro, cyano, $C_1$–$C_4$-alkyl, such as methyl, ethyl or tert-butyl, $C_1$–$C_4$-haloalkyl, such as fluoromethyl, trifluoromethyl, chlorodifluoromethyl, pentafluoroethyl or 2-chloro-1,1,2-trifluoroethyl, or $C_1$–$C_4$-alkoxy, such as methoxy, isopropoxy or tert-butoxy;

phenyl, which may carry from one to three of the following groups:

halogen, such as fluorine, chlorine, bromine or iodine, in particular fluorine or chlorine, nitro, cyano, $C_1$–$C_4$-alkyl, such as methyl, ethyl or tert-butyl, partially or fully halogenated $C_1$–$C_4$-alkyl, such as trifluoromethyl, 1,1,2,2-tetrafluoroethyl or trichloromethyl, $C_1$–$C_4$-alkoxy, such as methoxy, ethoxy or isopropoxy, partially or fully halogenated $C_1$–$C_4$-alkoxy, such as trifluoromethoxy, chlorodifluoromethoxy, 1-fluorothoxy, pentafluoroethoxy or 2-chloro-1,1,2-trifluoroethoxy, or $C_1$–C-alkoxycarbonyl, such as methoxycarbonyl, n-propoxycarbonyl or tert-butoxycarbonyl;

a 5- or 6-membered saturated heterocyclic radical or a 5- or 6-membered heteroaromatic radical, in each case having from 1 to 3 heteroatoms selected from the group comprising oxygen, sulfur and nitrogen, where two oxygen or sulfur atoms or one oxygen and one sulfur atom must not be directly adjacent, as mentioned above, in particular 2-tetrahydrofuranyl, 3-tetrahydrothienyl, 4-tetrahydropyranyl, 2-furanyl, 2-thienyl, 4-isoxazolyl, 5-isothiazolyl, 2-oxazolyl, 4-thiazolyl, 2-imidazolyl, 2-pyrrolyl, 3-pyrazolyl and 4-pyridyl, it being possible for the heterocyclic rings to also carry one or two of the following substituents: halogen as mentioned above, $C_1$–$C_3$-alkyl as mentioned above, $C_1$–$C_3$-alkoxy as mentioned above and/or $C_1$–$C_3$-alkoxycarbonyl as mentioned above;

benzotriazolyl;

N-phthalimido, tetrahydrophthalimido, N-succinimido or maleiimido;

2,2-dimethyl-1,3-dioxolan-4-ylmethyl or 1,3-dioxolan-2-on-4-ylmethyl;

in the case where Y=O: one equivalent of a cation from the group comprising the alkali metals and alkaline earth metals, such as sodium, potassium and calcium, manganese, copper, iron, ammonium and ammonium which is substituted by up to 4 $C_1$–$C_3$-alkyl groups, such as tetramethylammonium;

—N=$CR^8R^9$ where $R^8$ and $R^9$ are hydrogen;

$C_1$–$C_4$-alkyl or partially or fully halogenated $C_1$–$C_4$-alkyl, such as methyl, ethyl, isopropyl, tert-butyl, chloromethyl, fluoromethyl, trifluoromethyl, trichloromethyl or 1,1,2,2-tetrafluoroethyl, it being possible for the alkyl or haloalkyl group to also carry one of the following radicals:

$C_1$–$C_3$-alkoxy as mentioned above, in particular methoxy, phenyl, which may additionally be monosubstituted, disubstituted or trisubstituted by nitro, cyano, halogen as mentioned above, in particular fluorine or chlorine, $C_1$–$C_3$-alkyl as mentioned above, in particular methyl or tert-butyl, partially or fully halogenated $C_1$–$C_3$-alkyl as mentioned above, in particular trifluoromethyl, $C_1$–$C_3$-alkoxy as mentioned above, in particular methoxy, and/or partially or fully halogenated $C_1$–$C_3$-alkoxy as mentioned above, in particular trifluoromethoxy;

$C_3$–$C_5$-cycloalkyl, such as cyclopropyl, cyclopentyl or cyclohexyl;

$C_1$–$C_4$-alkoxy as mentioned above, in particular methoxy; furanyl or phenyl, which may additionally be monosubstituted, disubstituted or trisubstituted by nitro, cyano, halogen as mentioned above, in particular fluorine or chlorine, $C_1$–$C_3$-alkyl as mentioned above, in particular methyl or tert-butyl, partially or fully halogenated $C_1$–$C_3$-alkyl as mentioned above, in particular trifluoromethyl, $C_1$–$C_3$-alkoxy as mentioned above, in particular methoxy, and/or partially or fully halogenated $C_1$–$C_3$-alkoxy as mentioned above, in particular trifluoromethoxy;

$R^8$ and $R^9$
are together are a methylene chain having from 4 to 7 members, preferably 4 or 5 members;

—W—Z where
W is an ethylene, n-propylene, n-butylene, ethoxyethylene, but-2-enylen or but-2-ynylene chain;

Z is a molecular moiety which is bonded to W in the ω-position and is the same as that linked to W in the α-position of W, for example

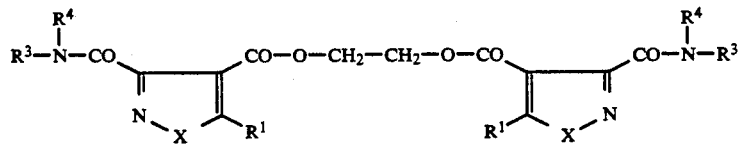

$R^6$ is
hydrogen;
$C_1$–$C_6$-alkyl, preferably $C_1$–$C_4$-alkyl, such as methyl, ethyl, isopropyl or tert-butyl;
$C_3$–$C_8$-cycloalkyl, preferably $C_3$–$C_6$-cycloalkyl, such as cyclopropyl, cyclopentyl or $R^7$ is
hydrogen;
$C_1$–$C_6$-alkyl, preferably $C_1$–$C_4$-alkyl, such as methyl or tert-butyl;
—C($OR^{12}$)=N—H or —C($OR^{12}$)=N—($C_1$–$C_4$-)-alkyl, where $C_1$–$C_4$-alkyl is alkyl as mentioned above, in particular methyl, ethyl or tertbutyl, and $R^{12}$ is likewise $C_1$–$C_4$-alkyl as mentioned above, in particular methyl;

$R^6$ and $R^7$ together are a methylene chain having from 4 to 7 members, preferably 4 or 5 members;

$R^3$ is
hydrogen;
$C_1$–$C_6$alkyl, preferably $C_1$–$C_4$-alkyl, such as methyl, ethyl or tert-butyl, which may carry from one to three of the following substituents: hydroxyl, halogen, $C_1$–$C_4$-alkoxy, such as methoxy or tert-butoxy, $C_1$–$C_4$-alkylthio, such as methylthio or tert-butylthio, or di($C_1$–$C_4$-)-alkylamino, preferably di($C_1$–$C_2$)-alkylamino, such as dimethylamino or diethylamino;

$C_3$–$C_8$-cycloalkyl, preferably $C_3$–$C_6$-cycloalkyl, such as cyclopropyl, cyclopentyl or cyclohexyl, which may be monosubstituted, disubstituted or trisubstituted by halogen, such as fluorine, chlorine or bromine, $C_1$–$C_4$-alkyl, such as methyl or tertbutyl, or by partially or fully halogenated $C_1$–$C_4$-alkyl, alkyl, such as fluoromethyl, trifluoromethyl, chlorodifluoromethyl, pentafluoroethyl or 2-chloro-1,1,2-trifluoroethyl;

$R^4$ is
hydrogen, hydroxyl;
$C_1$–$C_4$-alkoxy, such as methoxy, ethoxy or tert-butoxy;

linear or branched $C_1$–$C_6$-alkyl, preferably $C_1$–$C_4$-alkyl, such as methyl, ethyl, isopropyl or tertbutyl, which may carry from one to three of the following radicals: halogen, such as fluorine, chlorine or bromine, cyano, $C_1$–$C_4$-alkoxy, such as methoxy or tert-butoxy, partially or fully halogenated $C_1$–$C_4$-alkoxy, such as fluoromethoxy, trichloromethoxy, 2-chloro-1,1,2-trifluoroethoxy or pentafluoroethoxy, $C_1$–$C_4$-alkylthio, such as methylthio or tert-butylthio, $C_1$–$C_4$-haloalkylthio, such as fluoromethylthio, trichloromethylthio, 2-chloro-1,1,2-trifluoroethylthio or pentafluoroethylthio, di($C_1$–$C_4$)-alkylamino, in particular di($C_1$–$C_2$)-alkylamino, such as dimethylamino or diethylamino, $C_3$–$C_8$-cycloalkyl, in particular $C_3$–$C_6$-cycloalkyl, such as cyclopropyl, cyclopentyl or cyclohexyl, or phenyl, it being possible for the phenyl radical to itself carry up to three of the following groups:

halogen, such as fluorine, chlorine or bromine, cyano, nitro, $C_1$–$C_4$-alkyl, such as methyl or tert-butyl, $C_1$–$C_4$-haloalkyl, such as fluoromethyl, trichloromethyl, 2-chloro-1,1,2-trifluoroethyl or pentafluoroethyl, $C_1$–$C_4$-alkoxy, such as methoxy or tert-butoxy, partially or fully halogenated $C_1$–$C_4$-alkoxy, such as fluoromethoxy, trichloromethoxy, 2-chloro-1,1,2-trifluoroethoxy or pentafluoroethoxy, $C_1$–$C_4$-alkylthio, such as methylthio or tert-butylthio, or $C_1$–$C_4$-haloalkylthio, such as fluoromethylthio, trichlormethylthio, 2-chloro-1,1,2-trifluoroethylthio or pentafluoroethylthio;

$C_3$–$C_8$-cycloalkyl, preferably $C_3$–$C_6$-cycloalkyl, in particular cyclopropyl, cyclopentyl or cyclohexyl, each of which may carry from one to three of the following radicals: halogen, such as fluorine, chlorine or bromine, nitro, cyano, $C_1$–$C_6$-alkyl, preferably $C_1$–$C_4$-alkyl, such as methyl or tert-butyl, partially or fully halogenated $C_1$–$C_6$-alkyl, preferably $C_1$–$C_4$-haloalkyl, such as fluoromethyl, trichloromethyl, 2-chloro-1,1,2-trifluoroethyl or pentafluoroethyl, $C_1$–$C_4$-alkoxy, such as methoxy or tert-butoxy, or partially or fully halogenated $C_1$–$C_4$-alkoxy, such as fluoromethoxy, trichloromethoxy, 2-chloro-1,1,2-trifluoroethoxy or pentafluoroethoxy;

$C_3$–$C_6$-alkenyl or $C_3$–$C_6$-alkynyl, preferably $C_3$–$C_4$-alkenyl or $C_3$–$C_4$-alkynyl, such as 2-propenyl, 2-butenyl, 2-propynyl, 1,1-dimethyl-2-propynyl or 3-butynyl, each of which may be up to trisubstituted by halogen, such as fluorine, chlorine or bromine, and/or monosubstituted by phenyl, it being possible for the phenyl radical to itself carry from one to three of the following substituents: halogen, in particular fluorine or chlorine, cyano, nitro, $C_1$–$C_4$-alkyl, such as methyl or tert-butyl, partially or fully halogenated $C_1$–$C_4$-alkyl, such as fluoromethyl, trifluoromethyl, trichloromethyl, 2-chloro-1,1,2-trifluoroethyl or pentafluoroethyl, $C_1$–$C_4$-alkoxy, such as methoxy or tert-butoxy, $C_1$–$C_4$-haloalkoxy, such as fluoromethoxy, trifluoromethoxy, trichloromethoxy 2-chloro-1,1,2-trifluoroethoxy or pentafluoroethoxy, $C_1$–$C_4$-alkylthio, such as methylthio or tert-butylthio, partially or fully halogenated $C_1$–$C_4$-alkylthio, such as fluoromethylthio, trifluoromethylthio, trichloromethylthio, 2-chloro-1,1,2-trifluoroethylthio or pentafluoroethylthio;

di($C_1$–$C_4$)-alkylamino, preferably di($C_1$–$C_2$)-alkylamino, such as dimethylamino or diethylamino;

a 5- or 6-membered, saturated or aromatic heterocyclic radical, containing one or two heteroatoms selected from the group comprising oxygen, sulfur and nitrogen, such as 2-tetrahydrofuranyl, 3-tetrahydrofuranyl, 2-tetrahydrothienyl, 3-tetrahydrothienyl, 2-tetrahydropyranyl, 3-tetrahydropyranyl, 4-tetrahydropyranyl, 2-furanyl, 3-furanyl, 2-thienyl, 3-thienyl, 3-isoxazolyl, 4-isoxazolyl, 5-isoxazolyl, 3-isothiazolyl, 4-isothiazolyl, 5-isothiazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 2-pyrrolyl, 3-pyrrolyl, 3-pyrazolyl, 4-pyrazolyl, 5-pyrazolyl, 2-pyridyl, 3-pyridyl or 4-pyridyl, which may carry from one to three of the following substituents: $C_1$–$C_4$-alkyl as mentioned above, in particular methyl, or halogen as mentioned above, in particular fluorine or chlorine;

phenyl, which may carry from one to four of the following groups: $C_1$–$C_4$-alkyl as mentioned above, in particular methyl, ethyl or 1-methylethyl; partially or fully halogenated $C_1$–$C_4$-alkyl as mentioned above, in particular trifluoromethyl or chlorodifluoromethyl; $C_1$–$C_4$-alkoxy as mentioned above, in particular methoxy or ethoxy; partially or fully halogenated $C_1$–$C_4$-alkoxy as mentioned above, in particular trifluoromethoxy, trichloromethoxy or pentafluoroethoxy; $C_1$–$C_4$-alkylthio as mentioned above, in particular methylthio or ethylthio; partially or fully halogenated $C_1$–$C_4$-alkylthio as mentioned above, in particular difluoromethylthio, trifluoromethylthio or pentafluoromethylthio, halogen as mentioned above, in particular fluorine or chlorine, cyano, nitro, formyl, $C_1$–$C_4$-alkanoyl, such as acetyl, propionyl, butyryl, in particular acetyl, partially or fully halogenated $C_1$–$C_4$-alkanoyl, such as trifluoroacetyl, trichloroacetyl, pentafluoropropionyl, in particular trifluoroacetyl, $C_1$–$C_4$-alkoxycarbonyl, such as methoxycarbonyl or tertbutoxycarbonyl;

naphthyl, which may be monosubstituted, disubstituted or trisubstituted by $C_1$–$C_4$-alkyl, such as methyl or tert-butyl, in particular methyl or ethyl, or halogen such as fluorine or chlorine;

$R^3$ and $R^4$ together are a $C_1$–$C_7$-methylene chain, which may be interrupted by oxygen, sulfur or N-methyl, such as —(CH$_2$)$_3$—, —(CH$_2$)$_4$—, —(CH$_2$)$_5$—, —(CH$_2$)$_6$—, —CH$_2$—O—CH$_2$—, —CH$_2$—CH$_2$—O—CH$_2$—CH$_2$—, —CH$_2$—S—CH$_2$—, —CH$_2$—CH$_2$—S—CH$_2$—CH$_2$—, —CH$_2$—CH$_2$—N(CH$_3$)—CH$_2$—CH$_2$—, in particular —(CH$_2$)$_5$— and —CH$_2$—CH$_2$—O—CH$_2$—CH$_2$—;

or —(CH$_2$)$_3$—CO—.

Preferred compounds of the formulae Ia to Id are those in which $R^2$ is CO—Y—$R^5$, and Y is oxygen or sulfur:

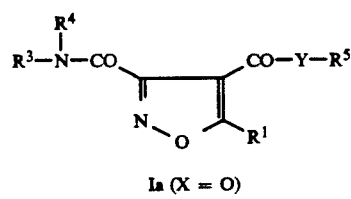

Ia (X = O)

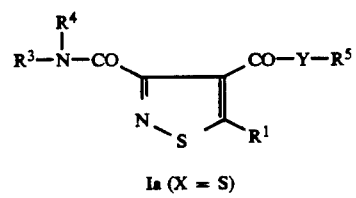

Ia (X = S)

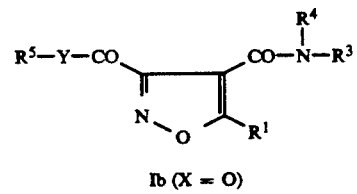

Ib (X = O)

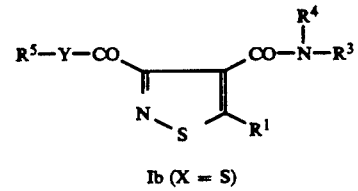

Ib (X = S)

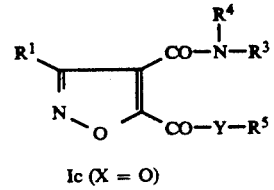

Ic (X = O)

-continued
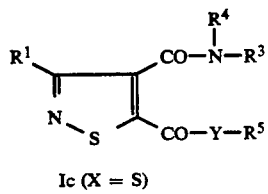
Ic (X = S)
-continued
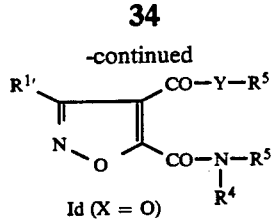
Id (X = O)
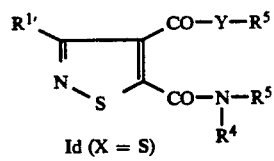
Id (X = S)
Table 1 shows examples of possible substituents $R^1$, $R^3$, $R^4$ and $R^5$ of the preferred compounds Ia-Ic ($R^2$=CO—Y—$R^5$), and Table 2 shows possible substituents of the compounds Id ($R^2$=CO—Y—$R^5$), the carboxamides Ia ($R^2$=CO—Y—$R^5$) being particularly preferred.

TABLE 1

| R¹ | R³ | R⁴ | R⁵ | Y |
|---|---|---|---|---|
| H | H | tert.-butyl | H | O |
| F | H | tert.-butyl | H | O |
| Cl | H | tert.-butyl | H | O |
| methyl | H | tert.-butyl | H | O |
| ethyl | H | tert.-butyl | H | O |
| n-propyl | H | tert.-butyl | H | O |
| iso-propyl | H | tert.-butyl | H | O |
| n-butyl | H | tert.-butyl | H | O |
| iso-butyl | H | tert.-butyl | H | O |
| sec.-butyl | H | tert.-butyl | H | O |
| tert.-butyl | H | tert.-butyl | H | O |
| cyclo-propyl | H | tert.-butyl | H | O |
| cyclo-butyl | H | tert.-butyl | H | O |
| cyclo-pentyl | H | tert.-butyl | H | O |
| cyclo-hexyl | H | tert.-butyl | H | O |
| cyclo-heptyl | H | tert.-butyl | H | O |
| cyclo-octyl | H | tert.-butyl | H | O |
| 1-methylcyclopropyl | H | tert.-butyl | H | O |
| chloromethyl | H | tert.-butyl | H | O |
| 1-chloroethyl | H | tert.-butyl | H | O |
| trifluoromethyl | H | tert.-butyl | H | O |
| chlorodifluoromethyl | H | tert.-butyl | H | O |
| pentafluoroethyl | H | tert.-butyl | H | O |
| methoxymethyl | H | tert.-butyl | H | O |
| 1-methylmethoxymethyl | H | tert.-butyl | H | O |
| 1-methylmethoxyethyl | H | tert.-butyl | H | O |
| ethoxymethyl | H | tert.-butyl | H | O |
| vinyl | H | tert.-butyl | H | O |
| allyl | H | tert.-butyl | H | O |
| methallyl | H | tert.-butyl | H | O |
| crotyl | H | tert.-butyl | H | O |
| ethynyl | H | tert.-butyl | H | O |
| propargyl | H | tert.-butyl | H | O |
| phenylethynyl | H | tert.-butyl | H | O |
| methoxy | H | tert.-butyl | H | O |
| ethoxy | H | tert.-butyl | H | O |
| trifluoromethoxy | H | tert.-butyl | H | O |
| methylthio | H | tert.-butyl | H | O |
| trifluoromethylthio | H | tert.-butyl | H | O |
| phenoxy | H | tert.-butyl | H | O |
| 4-Cl-phenoxy | H | tert.-butyl | H | O |
| 2,4-(Cl,Cl)-phenoxy | H | tert.-butyl | H | O |
| 4-CF₃-phenoxy | H | tert.-butyl | H | O |
| phenyl | H | tert.-butyl | H | O |
| 2-F-phenyl | H | tert.-butyl | H | O |
| 3-F-phenyl | H | tert.-butyl | H | O |
| 2,4-(F,F)-phenyl | H | tert.-butyl | H | O |
| 2-Cl-phenyl | H | tert.-butyl | H | O |
| 3-Cl-phenyl | H | tert.-butyl | H | O |
| 2,4-(Cl,Cl)-phenyl | H | tert.-butyl | H | O |
| 2-CH₃-phenyl | H | tert.-butyl | H | O |
| 3-CH₃-phenyl | H | tert.-butyl | H | O |

TABLE 1-continued

| R¹ | R³ | R⁴ | R⁵ | Y |
|---|---|---|---|---|
| 4-CH₃-phenyl | H | tert.-butyl | H | O |
| 2,4-(CH₃,CH₃)-phenyl | H | tert.-butyl | H | O |
| 2,4,6-(CH₃,CH₃,CH₃)-phenyl | H | tert.-butyl | H | O |
| 2-CF₃-phenyl | H | tert.-butyl | H | O |
| 2-OCH₃-phenyl | H | tert.-butyl | H | O |
| 2,4-(OCH₃,OCH₃)-phenyl | H | tert.-butyl | H | O |
| 4-OCF₃-phenyl | H | tert.-butyl | H | O |
| 4-SCH₃-phenyl | H | tert.-butyl | H | O |
| 3-SCF₃-phenyl | H | tert.-butyl | H | O |
| 2,4-(NO₂,NO₂)-phenyl | H | tert.-butyl | H | O |
| 4-NO₂-phenyl | H | tert.-butyl | H | O |
| 2-thienyl | H | tert.-butyl | H | O |
| 3-thienyl | H | tert.-butyl | H | O |
| 2-furanyl | H | tert.-butyl | H | O |
| 3-furanyl | H | tert.-butyl | H | O |
| 2-tetrahydrofuranyl | H | tert.-butyl | H | O |
| 3-tetrahydrofuranyl | H | tert.-butyl | H | O |
| 2-pyridyl | H | tert.-butyl | H | O |
| 3-pyridyl | H | tert.-butyl | H | O |
| 4-pyridyl | H | tert.-butyl | H | O |
| 2-tetrahydropyranyl | H | tert.-butyl | H | O |
| 3-tetrahydropyranyl | H | tert.-butyl | H | O |
| 4-tetrahydropyranyl | H | tert.-butyl | H | O |
| iso-propoxy | H | tert.-butyl | H | O |
| H | H | cyclo-propyl | H | O |
| F | H | cyclo-propyl | H | O |
| Cl | H | cyclo-propyl | H | O |
| methyl | H | cyclo-propyl | H | O |
| ethyl | H | cyclo-propyl | H | O |
| n-propyl | H | cyclo-propyl | H | O |
| iso-propyl | H | cyclo-propyl | H | O |
| n-butyl | H | cyclo-propyl | H | O |
| iso-butyl | H | cyclo-propyl | H | O |
| sec.-butyl | H | cyclo-propyl | H | O |
| tert.-butyl | H | cyclo-propyl | H | O |
| cyclo-propyl | H | cyclo-propyl | H | O |
| cyclo-butyl | H | cyclo-propyl | H | O |
| cyclo-pentyl | H | cyclo-propyl | H | O |
| cyclo-hexyl | H | cyclo-propyl | H | O |
| cyclo-heptyl | H | cyclo-propyl | H | O |
| cyclo-octyl | H | cyclo-propyl | H | O |
| 1-methylcyclopropyl | H | cyclo-propyl | H | O |
| chloromethyl | H | cyclo-propyl | H | O |
| 1-chloroethyl | H | cyclo-propyl | H | O |
| trifluoromethyl | H | cyclo-propyl | H | O |
| chlorodifluoromethyl | H | cyclo-propyl | H | O |
| pentafluoroethyl | H | cyclo-propyl | H | O |
| methoxymethyl | H | cyclo-propyl | H | O |
| 1-methylmethoxymethyl | H | cyclo-propyl | H | O |
| 1-methylmethoxyethyl | H | cyclo-propyl | H | O |
| ethoxymethyl | H | cyclo-propyl | H | O |
| vinyl | H | cyclo-propyl | H | O |

TABLE 1-continued

| R¹ | R³ | R⁴ | R⁵ | Y |
|---|---|---|---|---|
| allyl | H | cyclo-propyl | H | O |
| methallyl | H | cyclo-propyl | H | O |
| crotyl | H | cyclo-propyl | H | O |
| ethynyl | H | cyclo-propyl | H | O |
| propargyl | H | cyclo-propyl | H | O |
| phenylethynyl | H | cyclo-propyl | H | O |
| methoxy | H | cyclo-propyl | H | O |
| ethoxy | H | cyclo-propyl | H | O |
| trifluoromethoxy | H | cyclo-propyl | H | O |
| methylthio | H | cyclo-propyl | H | O |
| trifluoromethylthio | H | cyclo-propyl | H | O |
| phenoxy | H | cyclo-propyl | H | O |
| 4-Cl-phenoxy | H | cyclo-propyl | H | O |
| 2,4-(Cl,Cl)-phenoxy | H | cyclo-propyl | H | O |
| 4-CF₃-phenoxy | H | cyclo-propyl | H | O |
| phenyl | H | cyclo-propyl | H | O |
| 2-F-phenyl | H | cyclo-propyl | H | O |
| 3-F-phenyl | H | cyclo-propyl | H | O |
| 2,4-(F,F)-phenyl | H | cyclo-propyl | H | O |
| 2-Cl-phenyl | H | cyclo-propyl | H | O |
| 3-Cl-phenyl | H | cyclo-propyl | H | O |
| 2,4-(Cl,Cl)-phenyl | H | cyclo-propyl | H | O |
| 2-CH₃-phenyl | H | cyclo-propyl | H | O |
| 3-CH₃-phenyl | H | cyclo-propyl | H | O |
| 4-CH₃-phenyl | H | cyclo-propyl | H | O |
| 2,4-(CH₃,CH₃)-phenyl | H | cyclo-propyl | H | O |
| 2,4,6-(CH₃,CH₃,CH₃)-phenyl | H | cyclo-propyl | H | O |
| 2-CF₃-phenyl | H | cyclo-propyl | H | O |
| 2-OCH₃-phenyl | H | cyclo-propyl | H | O |
| 2,4-(OCH₃,OCH₃)-phenyl | H | cyclo-propyl | H | O |
| 4-OCF₃-phenyl | H | cyclo-propyl | H | O |
| 4-SCH₃-phenyl | H | cyclo-propyl | H | O |
| 3-SCF₃-phenyl | H | cyclo-propyl | H | O |
| 2,4-(NO₂,NO₂)-phenyl | H | cyclo-propyl | H | O |
| 4-NO₂-phenyl | H | cyclo-propyl | H | O |
| 2-thienyl | H | cyclo-propyl | H | O |
| 3-thienyl | H | cyclo-propyl | H | O |
| 2-furanyl | H | cyclo-propyl | H | O |
| 3-furanyl | H | cyclo-propyl | H | O |
| 2-tetrahydrofuranyl | H | cyclo-propyl | H | O |
| 3-tetrahydrofuranyl | H | cyclo-propyl | H | O |
| 2-pyridyl | H | cyclo-propyl | H | O |
| 3-pyridyl | H | cyclo-propyl | H | O |
| 4-pyridyl | H | cyclo-propyl | H | O |
| 2-tetrahydropyranyl | H | cyclo-propyl | H | O |
| 3-tetrahydropyranyl | H | cyclo-propyl | H | O |
| 4-tetrahydropyranyl | H | cyclo-propyl | H | O |
| iso-propoxy | H | cyclo-propyl | H | O |
| H | methyl | tert.-butyl | H | O |
| F | methyl | tert.-butyl | H | O |
| Cl | methyl | tert.-butyl | H | O |
| methyl | methyl | tert.-butyl | H | O |

TABLE 1-continued

| R¹ | R³ | R⁴ | R⁵ | Y |
|---|---|---|---|---|
| ethyl | methyl | tert.-butyl | H | O |
| n-propyl | methyl | tert.-butyl | H | O |
| iso-propyl | methyl | tert.-butyl | H | O |
| n-butyl | methyl | tert.-butyl | H | O |
| iso-butyl | methyl | tert.-butyl | H | O |
| sec.-butyl | methyl | tert.-butyl | H | O |
| tert.-butyl | methyl | tert.-butyl | H | O |
| cyclo-propyl | methyl | tert.-butyl | H | O |
| cyclo-butyl | methyl | tert.-butyl | H | O |
| cyclo-pentyl | methyl | tert.-butyl | H | O |
| cyclo-hexyl | iso-propyl | tert.-butyl | H | O |
| cyclo-heptyl | iso-propyl | tert.-butyl | H | O |
| cyclo-octyl | iso-propyl | tert.-butyl | H | O |
| 1-methylcyclopropyl | iso-propyl | tert.-butyl | H | O |
| trifluoromethyl | iso-propyl | tert.-butyl | H | O |
| chlorodifluoromethyl | iso-propyl | tert.-butyl | H | O |
| pentafluoroethyl | iso-propyl | tert.-butyl | H | O |
| methoxymethyl | iso-propyl | tert.-butyl | H | O |
| 1-methylmethoxymethyl | iso-propyl | tert.-butyl | H | O |
| 1-methylmethoxyethyl | iso-propyl | tert.-butyl | H | O |
| ethoxymethyl | iso-propyl | tert.-butyl | H | O |
| vinyl | iso-propyl | tert.-butyl | H | O |
| allyl | iso-propyl | tert.-butyl | H | O |
| methallyl | iso-propyl | tert.-butyl | H | O |
| crotyl | iso-propyl | tert.-butyl | H | O |
| ethynyl | iso-propyl | tert.-butyl | H | O |
| propargyl | iso-propyl | tert.-butyl | H | O |
| phenylethynyl | iso-propyl | tert.-butyl | H | O |
| methoxy | iso-propyl | tert.-butyl | H | O |
| ethoxy | iso-propyl | tert.-butyl | H | O |
| trifluoromethoxy | iso-propyl | tert.-butyl | H | O |
| H | methyl | cyclo-propyl | H | O |
| F | methyl | cyclo-propyl | H | O |
| Cl | methyl | cyclo-propyl | H | O |
| methyl | methyl | cyclo-propyl | H | O |
| ethyl | methyl | cyclo-propyl | H | O |
| n-propyl | methyl | cyclo-propyl | H | O |
| iso-propyl | iso-butyl | cyclo-propyl | H | O |
| n-butyl | iso-butyl | cyclo-propyl | H | O |
| iso-butyl | iso-butyl | cyclo-propyl | H | O |
| sec.-butyl | iso-butyl | cyclo-propyl | H | O |
| tert.-butyl | iso-butyl | cyclo-propyl | H | O |
| cyclo-propyl | iso-butyl | cyclo-propyl | H | O |
| cyclo-butyl | iso-butyl | cyclo-propyl | H | O |
| cyclo-pentyl | iso-butyl | cyclo-propyl | H | O |
| cyclo-hexyl | methyl | cyclo-propyl | H | O |
| cyclo-heptyl | methyl | cyclo-propyl | H | O |
| cyclo-octyl | methyl | cyclo-propyl | H | O |
| 1-methylcyclopropyl | methyl | cyclo-propyl | H | O |
| trifluoromethyl | methyl | cyclo-propyl | H | O |
| chlorodifluoromethyl | methyl | cyclo-propyl | H | O |
| pentafluoroethyl | methyl | cyclo-propyl | H | O |

TABLE 1-continued

| R¹ | R³ | R⁴ | R⁵ | Y |
|---|---|---|---|---|
| methyoxymethyl | iso-propyl | cyclo-proply | H | O |
| 1-methylmethoxymethyl | iso-propyl | cyclo-proply | H | O |
| 1-methylmethoxyethyl | iso-propyl | cyclo-proply | H | O |
| ethoxymethyl | iso-propyl | cyclo-proply | H | O |
| vinyl | iso-propyl | cyclo-proply | H | O |
| allyl | iso-propyl | cyclo-proply | H | O |
| methallyl | iso-propyl | cyclo-proply | H | O |
| crotyl | methyl | cyclo-propyl | H | O |
| ethynyl | methyl | cyclo-propyl | H | O |
| propargyl | methyl | cyclo-propyl | H | O |
| phenylethynyl | methyl | cyclo-propyl | H | O |
| methoxy | methyl | cyclo-propyl | H | O |
| ethoxy | methyl | cyclo-propyl | H | O |
| trifluoromethoxy | methyl | cyclo-propyl | H | O |
| chloro | H | tert.-butyl | 4-hydroxy-2-butynyl | O |
| chloro | H | tert.-butyl | N=C(C$_2$H$_5$)$_2$ | O |
| chloro | H | tert.-butyl | N=C(cyclo-C$_3$H$_5$)$_2$ | O |
| chloro | H | tert.-butyl | 2-butanimino | O |
| chloro | H | tert.-butyl | cyclohexanimino | O |
| chloro | H | tert.-butyl | cyclooctanimino | O |
| methyl | H | tert.-butyl | N=CH—C$_6$H$_5$ | O |
| methyl | H | tert.-butyl | 2-furyl-methanimino | O |
| methyl | H | tert.-butyl | CH$_2$CH$_2$N(CH$_3$)$_2$ | O |
| methyl | H | tert.-butyl | CH$_2$CH$_2$N$^+$(CH$_3$)$_2$I$^-$ | O |
| methyl | H | tert.-butyl | CH$_2$CF$_3$ | O |
| methyl | H | tert.-butyl | CH$_2$CH$_2$Cl | O |
| methyl | H | tert.-butyl | CH$_2$CH$_2$CN | O |
| methyl | H | tert.-butyl | methyl | O |
| methyl | H | tert.-butyl | ethyl | O |
| methyl | H | tert.-butyl | n-propyl | O |
| methyl | H | tert.-butyl | iso-propyl | O |
| methyl | H | tert.-butyl | tert.-butyl | O |
| methyl | H | tert.-butyl | n-butyl | O |
| methyl | H | tert.-butyl | CH$_2$—CCl$_3$ | O |
| methyl | H | tert.-butyl | CH$_2$—CH(OCH$_3$)$_2$ | O |
| methyl | H | tert.-butyl | CH$_2$—C(OCH$_3$)$_3$ | O |
| methyl | H | tert.-butyl | CH$_2$—CH(OH)—CH$_2$—OH | O |
| methyl | H | tert.-butyl | CH$_2$—CH$_2$—CH$_2$—CH$_2$—OH | O |
| methyl | H | tert.-butyl | CH$_2$—CH$_2$—O—CH$_3$ | O |
| methyl | H | tert.-butyl | CH$_2$—CH$_2$—S—CH$_3$ | O |
| methyl | H | tert.-butyl | CH$_2$—CH$_2$—NHCH$_3$ | O |
| methyl | H | tert.-butyl | CH$_2$—CH$_2$—NH(cyclopropyl) | O |
| methyl | H | tert.-butyl | CH$_2$—CH$_2$—N(cyclopropyl)$_2$ | O |
| methyl | H | tert.-butyl | CH$_2$—CH$_2$—Si(CH$_3$)$_3$ | O |
| methyl | H | tert.-butyl | CH$_2$—CH$_2$—SOCH$_3$ | O |
| methyl | H | tert.-butyl | CH$_2$—CH$_2$—SO$_2$CH$_3$ | O |
| methyl | H | tert.-butyl | CH$_2$—CO$_2$H | O |
| methyl | H | tert.-butyl | CH$_2$—CO$_2$CH$_3$ | O |
| methyl | H | tert.-butyl | CH$_2$—CH$_2$—O—CH$_2$—CH$_2$—CO$_2$CH$_3$ | O |
| methyl | H | tert.-butyl | CH$_2$—CH$_2$—CO$_2$—CH$_2$—CH$_2$—O—CH$_2$—CH$_2$—CO$_2$CH$_3$ | O |
| methyl | H | tert.-butyl | CH$_2$—CON(CH$_3$)$_2$ | O |
| methyl | H | tert.-butyl | CH$_2$—PO(OC$_2$H$_5$)$_2$ | O |

TABLE 1-continued

| R¹ | R³ | R⁴ | R⁵ | Y |
|---|---|---|---|---|
| methyl | H | tert.-butyl | CH₂—CH₂—O—N=C(CH₃)₂ | O |
| methyl | H | tert.-butyl | CH₂—CH₂—O—N= | O |
| methyl | H | tert.-butyl | N-phthalimidomethyl | O |
| methyl | H | tert.-butyl | N-succinimidomethyl | O |
| methyl | H | tert.-butyl | benzyloxymethyl | O |
| methyl | H | tert.-butyl | (4-Br-benzoyl)-methyl | O |
| methyl | H | tert.-butyl | (4-methoxybenzoyl)methyl | O |
| methyl | H | tert.-butyl | 2-tetrahydrofuranyl-methyl | O |
| methyl | H | tert.-butyl | 2-tetrahydrothienyl-methyl | O |
| methyl | H | tert.-butyl | 4-tetrahydropyranyl-methyl | O |
| methyl | H | tert.-butyl | 2-furanyl-methyl | O |
| methyl | H | tert.-butyl | 2-thienyl-methyl | O |
| methyl | H | tert.-butyl | —CH₂—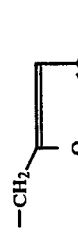 | O |
| methyl | H | tert.-butyl | —CH₂— | O |
| methyl | H | tert.-butyl | —CH₂—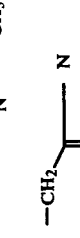 | O |
| methyl | H | tert.-butyl | —CH₂— | O |
| methyl | H | tert.-butyl | —CH₂—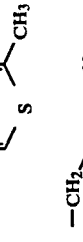 | O |
| methyl | H | tert.-butyl | N-methylpyrrolidin-3-ylmethyl | O |

TABLE 1-continued

| R¹ | R³ | R⁴ | R⁵ | Y |
|---|---|---|---|---|
| methyl | H | tert.-butyl | N-methylpyrrol-3-ylmethyl | O |
| methyl | | tert.-butyl | —CH₂—(1-methylpyrazol-3-yl) | O |
| methyl | H | tert.-butyl | —CH₂—(1-methyl-1,2,3-triazol-4-yl) | O |
| methyl | H | tert.-butyl | 2-pyridyl-methyl | O |
| methyl | H | tert.-butyl | 3-pyridyl-methyl | O |
| methyl | H | tert.-butyl | 4-pyridyl-methyl | O |
| methyl | H | tert.-butyl | —CH₂—(isoxazol-3-yl) | O |
| methyl | H | tert.-butyl | —CH₂—(thiadiazol-3-yl) | O |
| methyl | H | tert.-butyl | —CH₂—(pyrimidin-4-yl) | O |
| methyl | H | tert.-butyl | benzyl | O |
| methyl | H | tert.-butyl | 2,4-dichlorobenzyl | O |
| methyl | H | tert.-butyl | 2-phenylethyl | O |
| methyl | H | tert.-butyl | cyclopentyl | O |
| methyl | H | tert.-butyl | cyclohexyl | O |
| methyl | H | tert.-butyl | 2-propenyl | O |
| methyl | H | tert.-butyl | CH₂—CH=CH—C₆H₅ | O |
| methyl | H | tert.-butyl | 2-cyclohexenyl | O |
| methyl | H | tert.-butyl | 2-propynyl | O |
| methyl | H | tert.-butyl | CH₂—C≡C—CH₂—OH | O |
| methyl | H | tert.-butyl | 4-F-phenyl | O |

TABLE 1-continued

| R¹ | R³ | R⁴ | R⁵ | Y |
|---|---|---|---|---|
| methyl | H | tert.-butyl | 4-NO₂-phenyl | O |
| methyl | H | tert.-butyl | 4-CN-phenyl | O |
| methyl | H | tert.-butyl | 4-CH₃-phenyl | O |
| methyl | H | tert.-butyl | 4-CF₃-phenyl | O |
| methyl | H | tert.-butyl | 3,5-(CF₃,CF₃)-phenyl | O |
| methyl | H | tert.-butyl | 2-NO₂-4-F-phenyl | O |
| methyl | H | tert.-butyl | 4-OCH₃-phenyl | O |
| methyl | H | tert.-butyl | 4-OCF₃-phenyl | O |
| methyl | H | tert.-butyl | 4-CO₂CH₃-phenyl | O |
| methyl | H | tert.-butyl | 2,6(Br,Br)-4-NO₂-phenyl | O |
| methyl | H | tert.-butyl | 2-tetrahydrofuranyl | O |
| methyl | H | tert.-butyl | 2-tetrahydropyranyl | O |
| methyl | H | tert.-butyl | 1-pyrazolyl | O |
| methyl | H | tert.-butyl | 1-(1,2,3)-triazolyl | O |
| methyl | H | tert.-butyl | 1-benzotriazolyl | O |
| methyl | H | tert.-butyl | phthalimido | O |
| methyl | H | tert.-butyl | tetrahydrophthalimido | O |
| methyl | H | tert.-butyl | succinimido | O |
| methyl | H | tert.-butyl | maleinimido | O |
| methyl | H | tert.-butyl | Na+ | O |
| methyl | H | tert.-butyl | K+ | O |
| methyl | H | tert.-butyl | NH₄+ | O |
| methyl | H | tert.-butyl | ⊕NH₃-(iso-propyl) | O |
| methyl | H | tert.-butyl | ⊕NH₂-(iso-propyl)₂ | O |
| methyl | H | tert.-butyl | 2-propanimino | O |
| methyl | H | tert.-butyl | 2-butanimino | O |
| methyl | H | tert.-butyl | —N=C(C₂H₅)₂ | O |
| methyl | H | tert.-butyl | —N=CH—CH₂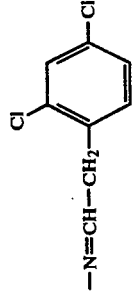 | O |
| methyl | H | tert.-butyl | —N=CH—CH₂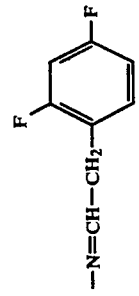 | O |
| methyl | H | tert.-butyl | —N=C(cyclopropyl)₂ | O |
| methyl | H | tert.-butyl | cyclopentanimino | O |
| methyl | H | tert.-butyl | cyclohexanimino | O |
| methyl | H | tert.-butyl | CH₂—CH=N—OCH₃ | O |

TABLE 1-continued

| R¹ | R³ | R⁴ | R⁵ | Y |
|---|---|---|---|---|
| methyl | H | tert.-butyl | CH₂—CH=N—OC₂H₅ | O |
| methyl | H | tert.-butyl | CH₂—CH=N—O—CH₂—C=CH₂ | O |
| methyl | H | tert.-butyl | CH₂—CH=N—O—CH₂—C≡CH | O |
| methyl | H | tert.-butyl | CH₂—CH=N—O—CH₂—CH₂—CH=CH-(4-F-phenyl) | O |
| iso-propyl | H | tert.-butyl | CH₂—CH=N—N—CH₃ | O |
| iso-propyl | H | tert.-butyl | CH₂—CH=N—N—C₆H₅ | O |
| iso-propyl | H | tert.-butyl | CH₂CCl₃ | O |
| iso-propyl | H | tert.-butyl | CH₂CH₂Si(CH₃)₃ | O |
| iso-propyl | H | tert.-butyl | CH₂CH₂O—N=C(CH₃) | O |
| iso-propyl | H | tert.-butyl | CH₂PO(OC₂H₅)₂ | O |
| iso-propyl | H | tert.-butyl | CH(CH₃)CH(OCH₃)₂ | O |
| iso-propyl | H | tert.-butyl | CH₂—CON(C₂H₅)₂ | O |
| cyclo-propyl | H | tert.-butyl | benzyl | O |
| cyclo-propyl | H | tert.-butyl | 2,4-(Cl,Cl)-benzyl | O |
| cyclo-propyl | H | tert.-butyl | 3-pyridyl-methyl | O |
| cyclo-propyl | H | tert.-butyl | 2-thienyl-methyl | O |
| cyclo-propyl | H | tert.-butyl | 2-tetrahydrofuranyl-methyl | O |
| cyclo-propyl | H | tert.-butyl | 2-furanyl-methyl | O |
| cyclo-propyl | H | tert.-butyl | 2-pyridyl-methyl | O |
| allyl | H | tert.-butyl | phenyl | O |
| allyl | H | tert.-butyl | 4-F-phenyl | O |
| allyl | H | tert.-butyl | 4-trifluoromethylphenyl | O |
| allyl | H | tert.-butyl | 2-NO₂,4-F-phenyl | O |
| allyl | H | tert.-butyl | 3,5-(CF₃,CF₃)-phenyl | O |
| allyl | H | tert.-butyl | 4-OCH₃-phenyl | O |
| allyl | H | tert.-butyl | 4-OCF₃-phenyl | O |
| allyl | H | tert.-butyl | 4-NHCOCH₃-phenyl | O |
| ethynyl | H | tert.-butyl | 2-tetrahydropyranyl | O |
| ethynyl | H | tert.-butyl | 2-tetrahydrofuranyl | O |
| ethynyl | H | tert.-butyl | 1-benzotriazolyl | O |
| ethynyl | H | tert.-butyl | methyl | O |
| ethynyl | H | tert.-butyl | ethyl | O |
| ethynyl | H | tert.-butyl | n-propyl | O |
| methoxy | H | tert.-butyl | iso-propyl | O |
| methoxy | H | tert.-butyl | n-butyl | O |
| methoxy | H | tert.-butyl | iso-butyl | O |
| methoxy | H | tert.-butyl | sec.-butyl | O |
| methoxy | H | tert.-butyl | tert.-butyl | O |
| methoxy | H | tert.-butyl | cyclo-hexyl | O |
| methoxy | H | tert.-butyl | cyclopropylmethyl | O |
| 4-Cl-phenoxy | H | tert.-butyl | ethoxymethyl | O |
| 4-Cl-phenoxy | H | tert.-butyl | 2-methoxy-ethoxy-methyl | O |
| 4-Cl-phenoxy | H | tert.-butyl | benzyloxymethyl | O |
| 4-Cl-phenoxy | H | tert.-butyl | (4-bromobenzoyl)-methyl | O |
| 4-Cl-phenoxy | H | tert.-butyl | (4-methoxybenzoyl)-methyl | O |
| 4-Cl-phenoxy | H | tert.-butyl | phthalimidomethyl | O |

TABLE 1-continued

| R¹ | R³ | R⁴ | R⁵ | Y |
|---|---|---|---|---|
| 4-Cl-phenoxy | H | tert.-butyl | methylthiomethyl | O |
| 4-Cl-phenoxy | H | tert.-butyl | 2-thiomethyl-ethyl | O |
| phenylthio | H | tert.-butyl | CH(C₆H₅)COOCH₃ | O |
| phenylthio | H | tert.-butyl | phenylethyl | O |
| phenylthio | H | tert.-butyl | 4-F-phenylethyl | O |
| phenylthio | H | tert.-butyl | phthalimido | O |
| phenylthio | H | tert.-butyl | tetrahydrophthalimido | O |
| phenylthio | H | tert.-butyl | maleiimido | O |
| phenylthio | H | tert.-butyl | succinimido | O |
| 2,4-(Cl,Cl)-phenyl | H | tert.-butyl | piperidino | O |
| 2,4-(Cl,Cl)-phenyl | H | tert.-butyl | Li⁺ | O |
| 2,4-(Cl,Cl)-phenyl | H | tert.-butyl | Na⁺ | O |
| 2,4-(Cl,Cl)-phenyl | H | tert.-butyl | K⁺ | O |
| 2,4-(Cl,Cl)-phenyl | H | tert.-butyl | NH₄⁺ | O |
| 2,4-(Cl,Cl)-phenyl | H | tert.-butyl | diisopropylammonium | O |
| 2,4-(Cl,Cl)-phenyl | H | tert.-butyl | 2-hydroxyethyl-ammonium | O |
| 2-thienyl | H | tert.-butyl | allyl | O |
| 2-thienyl | H | tert.-butyl | methallyl | O |
| 2-thienyl | H | tert.-butyl | 2-chloroallyl | O |
| 2-thienyl | H | tert.-butyl | propargyl | O |
| 2-thienyl | H | tert.-butyl | 3-iodopropargyl | O |
| chloro | H | cyclo-propyl | 4-hydroxy-2-butynyl | O |
| chloro | H | cyclo-propyl | N=C(C₂H₅)₂ | O |
| chloro | H | cyclo-propyl | N=C(cyclo-C₃H₅)₂ | O |
| chloro | H | cyclo-propyl | 2-butanimino | O |
| chloro | H | cyclo-propyl | cyclohexanimino | O |
| chloro | H | cyclo-propyl | cyclooctanimino | O |
| methyl | H | cyclo-propyl | N=CH—C₆H₅ | O |
| methyl | H | cyclo-propyl | 2-furyl-methanimino | O |
| methyl | H | cyclo-propyl | CH₂CH₂N(CH₃)₂ | O |
| methyl | H | cyclo-propyl | CH₂CH₂N⁺(CH₃)₃I⁻ | O |
| methyl | H | cyclo-propyl | CH₂CF₃ | O |
| methyl | H | cyclo-propyl | CH₂CH₂Cl | O |
| methyl | H | cyclo-propyl | CH₂CH₂CN | O |
| iso-propyl | H | cyclo-propyl | CH₂CCl₃ | O |
| iso-propyl | H | cyclo-propyl | CH₂CH₂Si(CH₃)₃ | O |
| iso-propyl | H | cyclo-propyl | CH₂CH₂O—N=C(CH₃)₂ | O |
| iso-propyl | H | cyclo-propyl | CH₂PO(OC₂H₅)₂ | O |
| iso-propyl | H | cyclo-propyl | CH(CH₃)CH(OCH₃)₂ | O |
| iso-propyl | H | cyclo-propyl | CH₂—CON(C₂H₅)₂ | O |
| cyclo-propyl | H | cyclo-propyl | benzyl | O |
| cyclo-propyl | H | cyclo-propyl | 2,4-(Cl,Cl)-benzyl | O |
| cyclo-propyl | H | cyclo-propyl | 3-pyridyl-methyl | O |
| cyclo-propyl | H | cyclo-propyl | 2-thienyl-methyl | O |
| cyclo-propyl | H | cyclo-propyl | 2-tetrahydrofuranyl-methyl | O |
| cyclo-propyl | H | cyclo-propyl | 2-furanyl-methyl | O |
| cyclo-propyl | H | cyclo-propyl | 2-pyridyl-methyl | O |
| allyl | H | cyclo-propyl | phenyl | O |
| allyl | H | cyclo-propyl | 4-F-phenyl | O |
| allyl | H | cyclo-propyl | 4-trifluoromethylphenyl | O |
| allyl | H | cyclo-propyl | 2-NO₂-4-F-phenyl | O |
| allyl | H | cyclo-propyl | 3,5-(CF₃,CF₃)-phenyl | O |

TABLE 1-continued

| R¹ | R³ | R⁴ | R⁵ | Y |
|---|---|---|---|---|
| allyl | H | cyclo-propyl | 4-OCH₃-phenyl | O |
| allyl | H | cyclo-propyl | 4-OCF₃-phenyl | O |
| allyl | H | cyclo-propyl | 4-NHCOCH₃-phenyl | O |
| ethynyl | H | cyclo-propyl | 2-tetrahydropyranyl | O |
| ethynyl | H | cyclo-propyl | 2-tetrahydrofuranyl | O |
| ethynyl | H | cyclo-propyl | 1-benzotriazolyl | O |
| ethynyl | H | cyclo-propyl | methyl | O |
| ethynyl | H | cyclo-propyl | ethyl | O |
| ethynyl | H | cyclo-propyl | n-propyl | O |
| methoxy | H | cyclo-propyl | iso-propyl | O |
| methoxy | H | cyclo-propyl | n-butyl | O |
| methoxy | H | cyclo-propyl | iso-butyl | O |
| methoxy | H | cyclo-propyl | sec.-butyl | O |
| methoxy | H | cyclo-propyl | tert.-butyl | O |
| methoxy | H | cyclo-propyl | cyclo-hexyl | O |
| methoxy | H | cyclo-propyl | cyclopropylmethyl | O |
| methoxy | H | cyclo-propyl | ethoxymethyl | O |
| 4-Cl-phenoxy | H | cyclo-propyl | 2-methoxy-ethoxy-methyl | O |
| 4-Cl-phenoxy | H | cyclo-propyl | benzyloxymethyl | O |
| 4-Cl-phenoxy | H | cyclo-propyl | (4-bromobenzoyl)-methyl | O |
| 4-Cl-phenoxy | H | cyclo-propyl | (4-methoxybenzoyl)-methyl | O |
| 4-Cl-phenoxy | H | cyclo-propyl | phthalimidomethyl | O |
| 4-Cl-phenoxy | H | cyclo-propyl | methylthiomethyl | O |
| 4-Cl-phenoxy | H | cyclo-propyl | 2-thiomethyl-ethyl | O |
| 4-Cl-phenoxy | H | cyclo-propyl | CH(C₆H₅)COOCH₃ | O |
| phenylthio | H | cyclo-propyl | phenylethyl | O |
| phenylthio | H | cyclo-propyl | 4-F-phenylethyl | O |
| phenylthio | H | cyclo-propyl | phthalimido | O |
| phenylthio | H | cyclo-propyl | tetrahydrophthalimido | O |
| phenylthio | H | cyclo-propyl | maleinimido | O |
| phenylthio | H | cyclo-propyl | succinimido | O |
| 2,4-(Cl,Cl)-phenyl | H | cyclo-propyl | piperidino | O |
| 2,4-(Cl,Cl)-phenyl | H | cyclo-propyl | Li⁺ | O |
| 2,4-(Cl,Cl)-phenyl | H | cyclo-propyl | Na⁺ | O |
| 2,4-(Cl,Cl)-phenyl | H | cyclo-propyl | K⁺ | O |
| 2,4-(Cl,Cl)-phenyl | H | cyclo-propyl | NH₄⁺ | O |
| 2,4-(Cl,Cl)-phenyl | H | cyclo-propyl | diisopropylammonium | O |
| 2,4-(Cl,Cl)-phenyl | H | cyclo-propyl | 2-hydroxyethyl-ammonium | O |
| 2-thienyl | H | cyclo-propyl | allyl | O |
| 2-thienyl | H | cyclo-propyl | methallyl | O |
| 2-thienyl | H | cyclo-propyl | 2-chloroallyl | O |
| 2-thienyl | H | cyclo-propyl | propargyl | O |
| 2-thienyl | H | cyclo-propyl | 3-iodopropargyl | O |
| H | H | tert.-butyl | —N=C(CH₃)₂ | O |
| F | H | tert.-butyl | —N=C(CH₃)₂ | O |
| Cl | H | tert.-butyl | —N=C(CH₃)₂ | O |
| methyl | H | tert.-butyl | —N=C(CH₃)₂ | O |
| ethyl | H | tert.-butyl | —N=C(CH₃)₂ | O |
| n-propyl | H | tert.-butyl | —N=C(CH₃)₂ | O |
| iso-propyl | H | tert.-butyl | —N=C(CH₃)₂ | O |
| n-butyl | H | tert.-butyl | —N=C(CH₃)₂ | O |
| iso-butyl | H | tert.-butyl | —N=C(CH₃)₂ | O |

TABLE 1-continued

| R¹ | R³ | R⁴ | R⁵ | Y |
|---|---|---|---|---|
| sec.-butyl | H | tert.-butyl | —N=C(CH₃)₂ | O |
| tert.-butyl | H | tert.-butyl | —N=C(CH₃)₂ | O |
| cyclo-propyl | H | tert.-butyl | —N=C(CH₃)₂ | O |
| cyclo-butyl | H | tert.-butyl | —N=C(CH₃)₂ | O |
| cyclo-pentyl | H | tert.-butyl | —N=C(CH₃)₂ | O |
| cyclo-hexyl | H | tert.-butyl | —N=C(CH₃)₂ | O |
| cyclo-heptyl | H | tert.-butyl | —N=C(CH₃)₂ | O |
| cyclo-octyl | H | tert.-butyl | —N=C(CH₃)₂ | O |
| 1-methylcyclopropyl | H | tert.-butyl | —N=C(CH₃)₂ | O |
| chloromethyl | H | tert.-butyl | —N=C(CH₃)₂ | O |
| 1-chloroethyl | H | tert.-butyl | —N=C(CH₃)₂ | O |
| trifluoromethyl | H | tert.-butyl | —N=C(CH₃)₂ | O |
| chlorodifluoromethyl | H | tert.-butyl | —N=C(CH₃)₂ | O |
| pentafluoromethyl | H | tert.-butyl | —N=C(CH₃)₂ | O |
| iso-propoxy | H | tert.-butyl | —N=C(CH₃)₂ | O |
| methoxymethyl | H | tert.-butyl | —N=C(CH₃)₂ | O |
| 1-methylmethoxymethyl | H | tert.-butyl | —N=C(CH₃)₂ | O |
| 1-methylmethoxyethyl | H | tert.-butyl | —N=C(CH₃)₂ | O |
| ethoxymethyl | H | tert.-butyl | —N=C(CH₃)₂ | O |
| vinyl | H | tert.-butyl | —N=C(CH₃)₂ | O |
| allyl | H | tert.-butyl | —N=C(CH₃)₂ | O |
| methallyl | H | tert.-butyl | —N=C(CH₃)₂ | O |
| crotyl | H | tert.-butyl | —N=C(CH₃)₂ | O |
| ethynyl | H | tert.-butyl | —N=C(CH₃)₂ | O |
| propargyl | H | tert.-butyl | —N=C(CH₃)₂ | O |
| phenylethynyl | H | tert.-butyl | —N=C(CH₃)₂ | O |
| methoxy | H | tert.-butyl | —N=C(CH₃)₂ | O |
| ethoxy | H | tert.-butyl | —N=C(CH₃)₂ | O |
| trifluoromethoxy | H | tert.-butyl | —N=C(CH₃)₂ | O |
| methylthio | H | tert.-butyl | —N=C(CH₃)₂ | O |
| trifluoromethylthio | H | tert.-butyl | —N=C(CH₃)₂ | O |
| phenoxy | H | tert.-butyl | —N=C(CH₃)₂ | O |
| 4-Cl-phenoxy | H | tert.-butyl | —N=C(CH₃)₂ | O |
| 2,4-(Cl,Cl)-phenoxy | H | tert.-butyl | —N=C(CH₃)₂ | O |
| 4-CF₃-phenoxy | H | tert.-butyl | —N=C(CH₃)₂ | O |
| phenyl | H | tert.-butyl | —N=C(CH₃)₂ | O |
| 2-F-phenylthio | H | tert.-butyl | —N=C(CH₃)₂ | O |
| 3-F-phenyl | H | tert.-butyl | —N=C(CH₃)₂ | O |
| 2,4-(F,F)-phenyl | H | tert.-butyl | —N=C(CH₃)₂ | O |
| 2-Cl-phenyl | H | tert.-butyl | —N=C(CH₃)₂ | O |
| 3-Cl-phenyl | H | tert.-butyl | —N=C(CH₃)₂ | O |
| 2,4-(Cl,Cl)-phenyl | H | tert.-butyl | —N=C(CH₃)₂ | O |
| 2-CH₃-phenyl | H | tert.-butyl | —N=C(CH₃)₂ | O |
| 3-CH₃-phenyl | H | tert.-butyl | —N=C(CH₃)₂ | O |
| 4-CH₃-phenyl | H | tert.-butyl | —N=C(CH₃)₂ | O |
| 2,4-(CH₃,CH₃)-phenyl | H | tert.-butyl | —N=C(CH₃)₂ | O |
| 2,4,6-(CH₃,CH₃,CH₃)-phenyl | H | tert.-butyl | —N=C(CH₃)₂ | O |
| 2-CF₃-phenyl | H | tert.-butyl | —N=C(CH₃)₂ | O |
| 2-OCH₃-phenyl | H | tert.-butyl | —N=C(CH₃)₂ | O |
| 2,4-(OCH₃,OCH₃)-phenyl | H | tert.-butyl | —N=C(CH₃)₂ | O |
| 4-OCF₃-phenyl | H | tert.-butyl | —N=C(CH₃)₂ | O |
| 4-SCH₃-phenyl | H | tert.-butyl | —N=C(CH₃)₂ | O |

TABLE 1-continued

| R¹ | R³ | R⁴ | R⁵ | Y |
|---|---|---|---|---|
| 3-SCF₃-phenyl | H | tert.-butyl | —N=C(CH₃)₂ | O |
| 2,4-(NO₂,NO₂)-phenyl | H | tert.-butyl | —N=C(CH₃)₂ | O |
| 4-NO₂-phenyl | H | tert.-butyl | —N=C(CH₃)₂ | O |
| 2-thienyl | H | tert.-butyl | —N=C(CH₃)₂ | O |
| 3-thienyl | H | tert.-butyl | —N=C(CH₃)₂ | O |
| 2-furanyl | H | tert.-butyl | —N=C(CH₃)₂ | O |
| 3-furanyl | H | tert.-butyl | —N=C(CH₃)₂ | O |
| 2-tetrahydrofuranyl | H | tert.-butyl | —N=C(CH₃)₂ | O |
| 3-tetrahydrofuranyl | H | tert.-butyl | —N=C(CH₃)₂ | O |
| 2-pyridyl | H | tert.-butyl | —N=C(CH₃)₂ | O |
| 3-pyridyl | H | tert.-butyl | —N=C(CH₃)₂ | O |
| 4-pyridyl | H | tert.-butyl | —N=C(CH₃)₂ | O |
| 2-tetrahydropyranyl | H | tert.-butyl | —N=C(CH₃)₂ | O |
| 3-tetrahydropyranyl | H | tert.-butyl | —N=C(CH₃)₂ | O |
| 4-tetrahydropyranyl | H | tert.-butyl | —N=C(CH₃)₂ | O |
| H | H | cyclo-propyl | —N=C(CH₃)₂ | O |
| F | H | cyclo-propyl | —N=C(CH₃)₂ | O |
| Cl | H | cyclo-propyl | —N=C(CH₃)₂ | O |
| methyl | H | cyclo-propyl | —N=C(CH₃)₂ | O |
| ethyl | H | cyclo-propyl | —N=C(CH₃)₂ | O |
| n-propyl | H | cyclo-propyl | —N=C(CH₃)₂ | O |
| iso-propyl | H | cyclo-propyl | —N=C(CH₃)₂ | O |
| n-butyl | H | cyclo-propyl | —N=C(CH₃)₂ | O |
| iso-butyl | H | cyclo-propyl | —N=C(CH₃)₂ | O |
| sec.-butyl | H | cyclo-propyl | —N=C(CH₃)₂ | O |
| tert.-butyl | H | cyclo-propyl | —N=C(CH₃)₂ | O |
| cyclo-propyl | H | cyclo-propyl | —N=C(CH₃)₂ | O |
| cyclo-butyl | H | cyclo-propyl | —N=C(CH₃)₂ | O |
| cyclo-pentyl | H | cyclo-propyl | —N=C(CH₃)₂ | O |
| cyclo-hexyl | H | cyclo-propyl | —N=C(CH₃)₂ | O |
| cyclo-heptyl | H | cyclo-propyl | —N=C(CH₃)₂ | O |
| cyclo-octyl | H | cyclo-propyl | —N=C(CH₃)₂ | O |
| 1-methylcyclopropyl | H | cyclo-propyl | —N=C(CH₃)₂ | O |
| chloromethyl | H | cyclo-propyl | —N=C(CH₃)₂ | O |
| 1-chloroethyl | H | cyclo-propyl | —N=C(CH₃)₂ | O |
| trifluoromethyl | H | cyclo-propyl | —N=C(CH₃)₂ | O |
| chlorodifluoromethyl | H | cyclo-propyl | —N=C(CH₃)₂ | O |
| pentafluoromethyl | H | cyclo-propyl | —N=C(CH₃)₂ | O |
| iso-propoxy | H | cyclo-propyl | —N=C(CH₃)₂ | O |
| methoxymethyl | H | cyclo-propyl | —N=C(CH₃)₂ | O |
| 1-methylmethoxymethyl | H | cyclo-propyl | —N=C(CH₃)₂ | O |
| 1-methylmethoxyethyl | H | cyclo-propyl | —N=C(CH₃)₂ | O |
| ethoxymethyl | H | cyclo-propyl | —N=C(CH₃)₂ | O |
| vinyl | H | cyclo-propyl | —N=C(CH₃)₂ | O |
| allyl | H | cyclo-propyl | —N=C(CH₃)₂ | O |
| methallyl | H | cyclo-propyl | —N=C(CH₃)₂ | O |
| crotyl | H | cyclo-propyl | —N=C(CH₃)₂ | O |
| ethynyl | H | cyclo-propyl | —N=C(CH₃)₂ | O |
| propargyl | H | cyclo-propyl | —N=C(CH₃)₂ | O |
| phenylethynyl | H | cyclo-propyl | —N=C(CH₃)₂ | O |
| methoxy | H | cyclo-propyl | —N=C(CH₃)₂ | O |
| ethoxy | H | cyclo-propyl | —N=C(CH₃)₂ | O |

TABLE 1-continued

| R¹ | R³ | R⁴ | R⁵ | Y |
|---|---|---|---|---|
| trifuloromethoxy | H | cyclo-propyl | —N═C(CH₃)₂ | O |
| methylthio | H | cyclo-propyl | —N═C(CH₃)₂ | O |
| trifluoromethylthio | H | cyclo-propyl | —N═C(CH₃)₂ | O |
| phenoxy | H | cyclo-propyl | —N═C(CH₃)₂ | O |
| 4-Cl-phenoxy | H | cyclo-propyl | —N═C(CH₃)₂ | O |
| 2,4-(Cl,Cl)-phenoxy | H | cyclo-propyl | —N═C(CH₃)₂ | O |
| 4-CF₃-phenoxy | H | cyclo-propyl | —N═C(CH₃)₂ | O |
| phenyl | H | cyclo-propyl | —N═C(CH₃)₂ | O |
| 2-F-phenyl | H | cyclo-propyl | —N═C(CH₃)₂ | O |
| 3-F-phenyl | H | cyclo-propyl | —N═C(CH₃)₂ | O |
| 2,4-(F,F)-phenyl | H | cyclo-propyl | —N═C(CH₃)₂ | O |
| 2-Cl-phenyl | H | cyclo-propyl | —N═C(CH₃)₂ | O |
| 3-Cl-phenyl | H | cyclo-propyl | —N═C(CH₃)₂ | O |
| 4-Cl-phenyl | H | cyclo-propyl | —N═C(CH₃)₂ | O |
| 2,4-(Cl,Cl)-phenyl | H | cyclo-propyl | —N═C(CH₃)₂ | O |
| 2-CH₃-phenyl | H | cyclo-propyl | —N═C(CH₃)₂ | O |
| 3-CH₃-phenyl | H | cyclo-propyl | —N═C(CH₃)₂ | O |
| 4-CH₃-phenyl | H | cyclo-propyl | —N═C(CH₃)₂ | O |
| 2,4-(CH₃,CH₃)-phenyl | H | cyclo-propyl | —N═C(CH₃)₂ | O |
| 2,4,6-(CH₃,CH₃,CH₃)-phenyl | H | cyclo-propyl | —N═C(CH₃)₂ | O |
| 2-CF₃-phenyl | H | cyclo-propyl | —N═C(CH₃)₂ | O |
| 2-OCH₃-phenyl | H | cyclo-propyl | —N═C(CH₃)₂ | O |
| 2,4-(OCH₃,OCH₃)-phenyl | H | cyclo-propyl | —N═C(CH₃)₂ | O |
| 4-OCF₃-phenyl | H | cyclo-propyl | —N═C(CH₃)₂ | O |
| 4-SCH₃-phenyl | H | cyclo-propyl | —N═C(CH₃)₂ | O |
| 3-SCF₃-phenyl | H | cyclo-propyl | —N═C(CH₃)₂ | O |
| 2,4-(NO₂,NO₂)-phenyl | H | cyclo-propyl | —N═C(CH₃)₂ | O |
| 4-NO₂-phenyl | H | cyclo-propyl | —N═C(CH₃)₂ | O |
| 2-thienyl | H | cyclo-propyl | —N═C(CH₃)₂ | O |
| 3-thienyl | H | cyclo-propyl | —N═C(CH₃)₂ | O |
| 2-furanyl | H | cyclo-propyl | —N═C(CH₃)₂ | O |
| 3-furanyl | H | cyclo-propyl | —N═C(CH₃)₂ | O |
| 2-tetrahydrofuranyl | H | cyclo-propyl | —N═C(CH₃)₂ | O |
| 3-tetrahydrofuranyl | H | cyclo-propyl | —N═C(CH₃)₂ | O |
| 2-pyridyl | H | cyclo-propyl | —N═C(CH₃)₂ | O |
| 3-pyridyl | H | cyclo-propyl | —N═C(CH₃)₂ | O |
| 4-pyridyl | H | cyclo-propyl | —N═C(CH₃)₂ | O |
| 2-tetrahydropyranyl | H | cyclo-propyl | —N═C(CH₃)₂ | O |
| 3-tetrahydropyranyl | H | cyclo-propyl | —N═C(CH₃)₂ | O |
| 4-tetrahydropyranyl | H | cyclo-propyl | —N═C(CH₃)₂ | O |
| chloro | H | methyl | H | O |
| chloro | H | ethyl | H | O |
| chloro | H | n-propyl | H | O |
| chloro | H | iso-propyl | H | O |
| chloro | H | n-butyl | H | O |
| chloro | H | iso-butyl | H | O |
| chloro | H | sec.-butyl | H | O |
| methyl | H | n-pentyl | H | O |
| methyl | H | 2-pentyl | H | O |
| methyl | H | 3-pentyl | H | O |
| methyl | H | n-hexyl | H | O |
| methyl | H | 2-hexyl | H | O |
| iso-propyl | H | 3-hexyl | H | O |

TABLE 1-continued

| R¹ | R³ | R⁴ | R⁵ | Y |
|---|---|---|---|---|
| iso-propyl | H | 2-methyl-2-pentyl | H | O |
| iso-propyl | H | cyclo-propylmethyl | H | O |
| iso-propyl | H | cyclo-butyl | H | O |
| iso-propyl | H | cyclo-pentyl | H | O |
| iso-propyl | H | cyclo-hexyl | H | O |
| cyclo-propyl | H | 1-methylcyclohexyl | H | O |
| cyclo-propyl | H | 3-trifluoromethylcyclohexyl | H | O |
| cyclo-propyl | H | allyl | H | O |
| cyclo-propyl | H | 1-buten-3-yl | H | O |
| cyclo-propyl | H | crotyl | H | O |
| cyclo-propyl | H | propargyl | H | O |
| allyl | H | 1-butyn-3-yl | H | O |
| allyl | H | 3-methyl-1-butyn-3-yl | H | O |
| allyl | H | 2-pentyn-4-yl | H | O |
| allyl | H | benzyl | H | O |
| allyl | H | 2-phenylethyl | H | O |
| allyl | H | 2-methylthioethyl | H | O |
| ethynyl | H | 2-chloroethyl | H | O |
| ethynyl | H | 2-methoxyethyl | H | O |
| ethynyl | H | 2-(N,N-dimethylamino)ethyl | H | O |
| ethynyl | H | phenyl | H | O |
| ethynyl | H | 2-CH₃-phenyl | H | O |
| ethynyl | H | 4-CH₃-phenyl | H | O |
| methoxy | H | 2,4-(CH₃,CH₃)-phenyl | H | O |
| methoxy | H | 2,3,5-(CH₃,CH₃,CH₃)-phenyl | H | O |
| methoxy | H | 3-CF₃-phenyl | H | O |
| methoxy | H | 3-F-phenyl | H | O |
| methoxy | H | 2-Cl-phenyl | H | O |
| methoxy | H | 4-Cl-phenyl | H | O |
| 4-Cl-phenoxy | H | 2,4-(F,F)-phenyl | H | O |
| 4-Cl-phenoxy | H | 2,3,5-(Cl,Cl,Cl)-phenyl | H | O |
| 4-Cl-phenoxy | H | 2-CN-phenyl | H | O |
| 4-Cl-phenoxy | H | 2-OCH₃-phenyl | H | O |
| 4-Cl-phenoxy | H | 2,3-(OCH₃,OCH₃)-phenyl | H | O |
| 4-Cl-phenoxy | H | 3,4,5-(OCH₃,OCH₃,OCH₃)-phenyl | H | O |
| phenylthio | H | 3-OCF₃-phenyl | H | O |
| phenylthio | H | 4-OCF₂CHF₂-phenyl | H | O |
| phenylthio | H | 2-SCH₃-phenyl | H | O |
| phenylthio | H | 2,4-(SCH₃,SCH₃)-phenyl | H | O |
| phenylthio | H | 2-SCF₃-phenyl | H | O |
| 2,4-(Cl,Cl)-phenyl | H | 4-NO₂-phenyl | H | O |
| 2,4-(Cl,Cl)-phenyl | H | 2,4-(NO₂,NO₂)-phenyl | H | O |
| 2,4-(Cl,Cl)-phenyl | H | 2-CHO-phenyl | H | O |
| 2,4-(Cl,Cl)-phenyl | H | 3-COCH₃-phenyl | H | O |
| 2,4-(Cl,Cl)-phenyl | H | 3-COCF₃-phenyl | H | O |
| 2,4-(Cl,Cl)-phenyl | H | 1-naphthyl | H | O |
| 2-thienyl | H | 2-naphthyl | H | O |
| 2-thienyl | H | piperidino | H | O |
| 2-thienyl | H | 3-tetrahydrofuranyl | H | O |
| 2-thienyl | H | 4-tetrahydropyranyl | H | O |
| 2-thienyl | H | 2-thiazolyl | H | O |
| 2-thienyl | H | 5-CH₃-2-thiazolyl | H | O |

TABLE 1-continued

| R¹ | R³ | R⁴ | R⁵ | Y |
|---|---|---|---|---|
| 2-thienyl | H | 4-CH₃-5-COOH-2-thiazolyl | H | O |
| 3-pyridyl | H | methyl | H | O |
| 3-pyridyl | H | ethyl | H | O |
| 3-pyridyl | H | n-propyl | H | O |
| 3-pyridyl | H | iso-propyl | H | O |
| 3-pyridyl | H | n-butyl | H | O |
| 3-pyridyl | H | iso-butylyl | H | O |
| iso-propyl | methyl | sec.-butyl | H | O |
| iso-propyl | methyl | n-pentyl | H | O |
| iso-propyl | methyl | 2-pentyl | H | O |
| iso-propyl | methyl | 3-pentyl | H | O |
| iso-propyl | methyl | n-hexyl | H | O |
| iso-propyl | methyl | 2-hexyl | H | O |
| iso-propyl | methyl | 3-hexyl | H | O |
| chloro | H | methyl | H | O |
| chloro | H | ethyl | H | O |
| chloro | H | n-propyl | H | O |
| chloro | H | iso-propyl | H | O |
| chloro | H | n-butyl | H | O |
| chloro | H | iso-butyl | H | O |
| chloro | H | sec.-butyl | H | O |
| methyl | H | n-pentyl | H | O |
| methyl | H | 2-pentyl | H | O |
| methyl | H | 3-pentyl | H | O |
| methyl | H | n-hexyl | H | O |
| methyl | H | 2-hexyl | H | O |
| methyl | H | 3-hexyl | H | O |
| iso-propyl | H | 2-methyl-2-pentyl | H | O |
| iso-propyl | H | cyclo-propylmethyl | H | O |
| iso-propyl | H | cyclo-butyl | H | O |
| iso-propyl | H | cyclo-pentyl | H | O |
| iso-propyl | H | cyclo-hexyl | H | O |
| cyclo-propyl | H | 1-methylcyclohexyl | H | O |
| cyclo-propyl | H | 3-trifluoromethylcyclohexyl | H | O |
| cyclo-propyl | H | allyl | H | O |
| cyclo-propyl | H | 1-buten-3-yl | H | O |
| cyclo-propyl | H | crotyl | H | O |
| cyclo-propyl | H | propargyl | H | O |
| allyl | H | 1-butyn-3-yl | H | O |
| allyl | H | 3-methyl-1-butyn-3-yl | H | O |
| allyl | H | 2-pentyn-4-yl | H | O |
| allyl | H | benzyl | H | O |
| allyl | H | 2-phenylethyl | H | O |
| allyl | H | 2-methylthioethyl | H | O |
| allyl | H | 2-chloroethyl | H | O |
| ethynyl | H | 2-methoxyethyl | —N=C(CH₃)₂ | O |
| ethynyl | H | 2-(N,N-dimethylamino)ethyl | —N=C(CH₃)₂ | O |
| ethynyl | H | phenyl | —N=C(CH₃)₂ | O |
| ethynyl | H | 2-CH₃-phenyl | —N=C(CH₃)₂ | O |
| ethynyl | H | 4-CH₃-phenyl | —N=C(CH₃)₂ | O |
| methoxy | H | 2,4-(CH₃,CH₃)-phenyl | —N=C(CH₃)₂ | O |
| methoxy | H | 2,3,5-(CH₃,CH₃,CH₃)-phenyl | —N=C(CH₃)₂ | O |

TABLE 1-continued

| R¹ | R³ | R⁴ | R⁵ | Y |
|---|---|---|---|---|
| methoxy | H | 3-CF₃-phenyl | —N=C(CH₃)₂ | O |
| methoxy | H | 3-F-phenyl | —N=C(CH₃)₂ | O |
| methoxy | H | 2-Cl-phenyl | —N=C(CH₃)₂ | O |
| methoxy | H | 4-Cl-phenyl | —N=C(CH₃)₂ | O |
| 4-Cl-phenoxy | H | 2,4-(F,F)-phenyl | —N=C(CH₃)₂ | O |
| 4-Cl-phenoxy | H | 2,3,5-(Cl,Cl,Cl)-phenyl | —N=C(CH₃)₂ | O |
| 4-Cl-phenoxy | H | 2-CN-phenyl | —N=C(CH₃)₂ | O |
| 4-Cl-phenoxy | H | 2-OCH₃-phenyl | —N=C(CH₃)₂ | O |
| 4-Cl-phenoxy | H | 2,3-(OCH₃,OCH₃)-phenyl | —N=C(CH₃)₂ | O |
| 4-Cl-phenoxy | H | 3,4,5-(OCH₃,OCH₃,OCH₃)-phenyl | —N=C(CH₃)₂ | O |
| phenylthio | H | 3-OCF₃-phenyl | —N=C(CH₃)₂ | O |
| phenylthio | H | 4-OCF₂CHF₂-phenyl | —N=C(CH₃)₂ | O |
| phenylthio | H | 2-SCH₃-phenyl | —N=C(CH₃)₂ | O |
| phenylthio | H | 2,4-(SCH₃,SCH₃)-phenyl | —N=C(CH₃)₂ | O |
| phenylthio | H | 2-SCF₃-phenyl | —N=C(CH₃)₂ | O |
| phenylthio | H | 4-NO₂-phenyl | —N=C(CH₃)₂ | O |
| 2,4-(Cl,Cl)-phenyl | H | 2,4-(NO₂,NO₂)-phenyl | —N=C(CH₃)₂ | O |
| 2,4-(Cl,Cl)-phenyl | H | 2-CHO-phenyl | —N=C(CH₃)₂ | O |
| 2,4-(Cl,Cl)-phenyl | H | 3-COCH₃-phenyl | —N=C(CH₃)₂ | O |
| 2,4-(Cl,Cl)-phenyl | H | 3-COCF₃-phenyl | —N=C(CH₃)₂ | O |
| 2,4-(Cl,Cl)-phenyl | H | 1-naphthyl | —N=C(CH₃)₂ | O |
| 2,4-(Cl,Cl)-phenyl | H | 2-naphthyl | —N=C(CH₃)₂ | O |
| 2-thienyl | H | piperidino | —N=C(CH₃)₂ | O |
| 2-thienyl | H | 3-tetrahydrofuranyl | —N=C(CH₃)₂ | O |
| 2-thienyl | H | 4-tetrahydropyranyl | —N=C(CH₃)₂ | O |
| 2-thienyl | H | 2-thiazolyl | —N=C(CH₃)₂ | O |
| 2-thienyl | H | 5-CH₃-2-thiazolyl | —N=C(CH₃)₂ | O |
| 2-thienyl | H | 4-CH₃-5-COOH-2-thiazolyl | —N=C(CH₃)₂ | O |
| 3-pyridyl | H | methyl | —N=C(CH₃)₂ | O |
| 3-pyridyl | H | ethyl | —N=C(CH₃)₂ | O |
| 3-pyridyl | H | n-propyl | —N=C(CH₃)₂ | O |
| 3-pyridyl | H | iso-propyl | —N=C(CH₃)₂ | O |
| 3-pyridyl | H | n-butyl | —N=C(CH₃)₂ | O |
| 3-pyridyl | H | iso-butyl | —N=C(CH₃)₂ | O |
| iso-propyl | methyl | sec.-butyl | —N=C(CH₃)₂ | O |
| iso-propyl | methyl | n-pentyl | —N=C(CH₃)₂ | O |
| iso-propyl | methyl | 2-pentyl | —N=C(CH₃)₂ | O |
| iso-propyl | methyl | 3-pentyl | —N=C(CH₃)₂ | O |
| iso-propyl | methyl | n-hexyl | —N=C(CH₃)₂ | O |
| iso-propyl | methyl | 2-hexyl | —N=C(CH₃)₂ | O |
| iso-propyl | methyl | 3-hexyl | —N=C(CH₃)₂ | O |
| methyl | H | tert.-butyl | 2,4-(Cl,Cl)-phenyl | O |
| methyl | H | tert.-butyl | 2-pyridyl | S |
| methyl | H | tert.-butyl | ethyl | S |
| methyl | H | tert.-butyl | iso-propyl | S |
| methyl | H | tert.-butyl | butyl | S |
| methyl | H | tert.-butyl | tert.-butyl | S |
| methyl | H | tert.-butyl | phenyl | S |
| methyl | H | tert.-butyl | 4-F-phenyl | S |
| iso-propyl | H | tert.-butyl | 3-CF₃-phenyl | S |
| iso-propyl | H | tert.-butyl | 2,4-(Cl,Cl)-phenyl | S |
| iso-propyl | H | tert.-butyl | 2-pyridyl | S |

TABLE 1-continued

| R¹ | R³ | R⁴ | R⁵ | Y |
|---|---|---|---|---|
| iso-propyl | H | tert.-butyl | methyl | S |
| iso-propyl | H | tert.-butyl | ethyl | S |
| iso-propyl | H | tert.-butyl | iso-propyl | S |
| cyclo-propyl | H | tert.-butyl | butyl | S |
| cyclo-propyl | H | tert.-butyl | tert.-butyl | S |
| cyclo-propyl | H | tert.-butyl | phenyl | S |
| cyclo-propyl | H | tert.-butyl | 4-F-phenyl | S |
| cyclo-propyl | H | tert.-butyl | 3-CF₃-phenyl | S |
| cyclo-propyl | H | tert.-butyl | 2,4-(Cl,Cl)-phenyl | S |
| cyclo-propyl | H | tert.-butyl | 2-pyridyl | S |
| allyl | H | tert.-butyl | methyl | S |
| allyl | H | tert.-butyl | ethyl | S |
| allyl | H | tert.-butyl | iso-propyl | S |
| allyl | H | tert.-butyl | butyl | S |
| allyl | H | tert.-butyl | tert.-butyl | S |
| allyl | H | tert.-butyl | phenyl | S |
| methoxy | H | tert.-butyl | methyl | S |
| methoxy | H | tert.-butyl | ethyl | S |
| methoxy | H | tert.-butyl | iso-propyl | S |
| methoxy | H | tert.-butyl | butyl | S |
| methoxy | H | tert.-butyl | tert.-butyl | S |
| methoxy | H | tert.-butyl | phenyl | S |
| methoxy | H | tert.-butyl | 4-F-phenyl | S |
| methoxy | H | tert.-butyl | 3-CF₃-phenyl | S |
| 4-Cl-phenoxy | H | tert.-butyl | 2,4-(Cl,Cl)-phenyl | S |
| 4-Cl-phenoxy | H | tert.-butyl | 2-pyridyl | S |
| 4-Cl-phenoxy | H | tert.-butyl | methyl | S |
| 4-Cl-phenoxy | H | tert.-butyl | ethyl | S |
| 4-Cl-phenoxy | H | tert.-butyl | iso-propyl | S |
| 4-Cl-phenoxy | H | tert.-butyl | butyl | S |
| 4-Cl-phenoxy | H | tert.-butyl | tert.-butyl | S |
| 4-Cl-phenoxy | H | tert.-butyl | phenyl | S |
| 2,4-(Cl,Cl)-phenyl | H | tert.-butyl | 4-F-phenyl | S |
| 2,4-(Cl,Cl)-phenyl | H | tert.-butyl | 3-CF₃-phenyl | S |
| 2,4-(Cl,Cl)-phenyl | H | tert.-butyl | 2,4-(Cl,Cl)-phenyl | S |
| 2,4-(Cl,Cl)-phenyl | H | tert.-butyl | 2-pyridyl | S |
| 2,4-(Cl,Cl)-phenyl | H | tert.-butyl | methyl | S |
| 2,4-(Cl,Cl)-phenyl | H | tert.-butyl | ethyl | S |
| 2-thienyl | H | tert.-butyl | iso-propyl | S |
| 2-thienyl | H | tert.-butyl | butyl | S |
| 2-thienyl | H | tert.-butyl | tert.-butyl | S |
| 3-pyridyl | H | tert.-butyl | phenyl | S |
| 3-pyridyl | H | tert.-butyl | 4-F-phenyl | S |
| methyl | H | cyclo-propyl | 3-CF₃-phenyl | S |
| methyl | H | cyclo-propyl | 2,4-(Cl,Cl)-phenyl | S |
| methyl | H | cyclo-propyl | 2-pyridyl | S |
| methyl | H | cyclo-propyl | ethyl | S |
| methyl | H | cyclo-propyl | iso-propyl | S |
| methyl | H | cyclo-propyl | butyl | S |
| methyl | H | cyclo-propyl | tert.-butyl | S |
| iso-propyl | H | cyclo-propyl | phenyl | S |
| iso-propyl | H | cyclo-propyl | 4-F-phenyl | S |
| iso-propyl | H | cyclo-propyl | 3-CF₃-phenyl | S |

TABLE 1-continued

| R¹ | R³ | R⁴ | R⁵ | Y |
|---|---|---|---|---|
| iso-propyl | H | cyclo-propyl | 2,4-(Cl,Cl)-phenyl | s |
| iso-propyl | H | cyclo-propyl | 2-pyridyl | s |
| iso-propyl | H | cyclo-propyl | methyl | s |
| iso-propyl | H | cyclo-propyl | ethyl | s |
| iso-propyl | H | cyclo-propyl | iso-propyl | s |
| iso-propyl | H | cyclo-propyl | butyl | s |
| cyclo-propyl | H | cyclo-propyl | tert.-butyl | s |
| cyclo-propyl | H | cyclo-propyl | phenyl | s |
| cyclo-propyl | H | cyclo-propyl | 4-F-phenyl | s |
| cyclo-propyl | H | cyclo-propyl | 3-CF₃-phenyl | s |
| cyclo-propyl | H | cyclo-propyl | 2,4-(Cl,Cl)-phenyl | s |
| cyclo-propyl | H | cyclo-propyl | 2-pyridyl | s |
| allyl | H | cyclo-propyl | methyl | s |
| allyl | H | cyclo-propyl | ethyl | s |
| allyl | H | cyclo-propyl | iso-propyl | s |
| allyl | H | cyclo-propyl | butyl | s |
| allyl | H | cyclo-propyl | tert.-butyl | s |
| allyl | H | cyclo-propyl | phenyl | s |
| methoxy | H | cyclo-propyl | methyl | s |
| methoxy | H | cyclo-propyl | ethyl | s |
| methoxy | H | cyclo-propyl | iso-propyl | s |
| methoxy | H | cyclo-propyl | butyl | s |
| methoxy | H | cyclo-propyl | tert.-butyl | s |
| methoxy | H | cyclo-propyl | phenyl | s |
| methoxy | H | cyclo-propyl | 4-F-phenyl | s |
| methoxy | H | cyclo-propyl | 3-CF₃-phenyl | s |
| 4-Cl-phenoxy | H | cyclo-propyl | 2,4-(Cl,Cl)-phenyl | s |
| 4-Cl-phenoxy | H | cyclo-propyl | 2-pyridyl | s |
| 4-Cl-phenoxy | H | cyclo-propyl | methyl | s |
| 4-Cl-phenoxy | H | cyclo-propyl | ethyl | s |
| 4-Cl-phenoxy | H | cyclo-propyl | iso-propyl | s |
| 4-Cl-phenoxy | H | cyclo-propyl | butyl | s |
| 4-Cl-phenoxy | H | cyclo-propyl | tert.-butyl | s |
| 2,4-(Cl,Cl)-phenyl | H | cyclo-propyl | phenyl | s |
| 2,4-(Cl,Cl)-phenyl | H | cyclo-propyl | 4-F-phenyl | s |
| 2,4-(Cl,Cl)-phenyl | H | cyclo-propyl | 3-CF₃-phenyl | s |
| 2,4-(Cl,Cl)-phenyl | H | cyclo-propyl | 2,4-(Cl,Cl)-phenyl | s |
| 2,4-(Cl,Cl)-phenyl | H | cyclo-propyl | 2-pyridyl | s |
| 2,4-(Cl,Cl)-phenyl | H | cyclo-propyl | ethyl | s |
| 2,4-(Cl,Cl)-phenyl | H | cyclo-propyl | iso-propyl | s |
| 2-thienyl | H | cyclo-propyl | butyl | s |
| 2-thienyl | H | cyclo-propyl | tert.-butyl | s |
| 2-thienyl | H | cyclo-propyl | phenyl | s |
| 3-pyridyl | H | cyclo-propyl | 4-F-phenyl | s |
| 3-pyridyl | H | cyclo-propyl | 3-CF₃-phenyl | s |

TABLE 2

$R^2 = COOH$
$R^3 = H$ (Structure: pyrazole/isoxazole ring with $R^{1'}$, $COOR^5$, $CO-N(H)(R^4)$, X)

| R¹' | R⁴ | R⁵ | x |
|---|---|---|---|
| cyclopropyl-CH(CH₃)— | tert.-butyl | H | O |
| cyclopropyl-CH(C₂H₅)— | tert.-butyl | H | O |
| CH₂=CH— | tert.-butyl | H | O |
| E—CH₃—CH=CH— | tert.-butyl | H | O |
| Z—CH₃—CH=CH | tert.-butyl | H | O |
| CH₂=CH—CH₂— | tert.-butyl | H | O |
| CH₂=C(CH₃)— | tert.-butyl | H | O |
| C₂H₅—CH=CH— | tert.-butyl | H | O |
| CH₃—CH=C(CH₃)— | tert.-butyl | H | O |
| CH₂=C(C₂H₅)— | tert.-butyl | H | O |
| CH₃—CH=C(C₂H₅)— | tert.-butyl | H | O |
| (CH₃)₂C=CH— | tert.-butyl | H | O |
| CH₂=C(CH₃)—CH(CH₃)— | tert.-butyl | H | O |
| (CH₃)₂C=CH—CH₂— | tert.-butyl | H | O |
| CH₃—CCl=CH— | tert.-butyl | H | O |
| Cl₂C=CH— | tert.-butyl | H | O |
| cyclopent-1-ene | tert.-butyl | H | O |
| cyclohex-1-ene | tert.-butyl | H | O |
| 1-CH₃-cyclohex-2-ene | tert.-butyl | H | O |
| E-phenyl-CH=CH— | tert.-butyl | H | O |
| E-4-(CH₃O)—C₆H₅—CH=CH— | tert.-butyl | H | O |
| HC≡C— | tert.-butyl | H | O |
| CH₃—C≡C— | tert.-butyl | H | O |
| HC≡C—CH₂ | tert.-butyl | H | O |
| phenyl—C≡C— | tert.-butyl | H | O |
| CH₃—CH(O)CH— (epoxide) | tert.-butyl | H | O |
| cyclopropyl-CH(CH₃)— | cyclopropyl | H | O |
| cyclopropyl-CH(C₂H₅)— | cyclopropyl | H | O |
| CH₂=CH— | cyclopropyl | H | O |
| E—CH₃—CH=CH— | cyclopropyl | H | O |
| Z—CH₃—CH=CH | cyclopropyl | H | O |
| CH₂=CH—CH₂— | cyclopropyl | H | O |
| CH₂=C(CH₃)— | cyclopropyl | H | O |
| C₂H₅—CH=CH— | cyclopropyl | H | O |
| CH₃—CH=C(CH₃)— | cyclopropyl | H | O |
| CH₂=C(C₂H₅)— | cyclopropyl | H | O |
| CH₃—CH=C(C₂H₅)— | cyclopropyl | H | O |
| (CH₃)₂C=CH— | cyclopropyl | H | O |
| CH₂=C(CH₃)—CH(CH₃)— | cyclopropyl | H | O |
| (CH₃)₂C=CH—CH₂— | cyclopropyl | H | O |
| CH₃—CCl=CH— | cyclopropyl | H | O |
| Cl₂C=CH— | cyclopropyl | H | O |
| cyclopent-1-ene | cyclopropyl | H | O |
| cyclohex-1-ene | cyclopropyl | H | O |
| 1-CH₃-cyclohex-2-ene | cyclopropyl | H | O |
| E-phenyl-CH=CH— | cyclopropyl | H | O |
| E-4-(CH₃O)—C₆H₅—CH=CH— | cyclopropyl | H | O |
| HC≡C— | cyclopropyl | H | O |
| CH₃—C≡C— | cyclopropyl | H | O |
| HC≡C—CH₂ | cyclopropyl | H | O |
| phenyl—C≡C— | cyclopropyl | H | O |
| CH₃—CH(O)CH— (epoxide) | cyclopropyl | H | O |
| cyclopropyl-CH(CH₃)— | C(CH₃)₂C≡CH | H | O |
| cyclopropyl-CH(C₂H₅)— | C(CH₃)₂C≡CH | H | O |
| CH₂=CH— | C(CH₃)₂C≡CH | H | O |
| E—CH₃—CH=CH— | C(CH₃)₂C≡CH | H | O |
| Z—CH₃—CH=CH | C(CH₃)₂C≡CH | H | O |
| CH₂=CH—CH₂— | C(CH₃)₂C≡CH | H | O |
| CH₂=C(CH₃)— | C(CH₃)₂C≡CH | H | O |
| C₂H₅—CH=CH— | C(CH₃)₂C≡CH | H | O |
| CH₃—CH=C(CH₃)— | C(CH₃)₂C≡CH | H | O |
| CH₂=C(C₂H₅)— | C(CH₃)₂C≡CH | H | O |
| CH₃—CH=C(C₂H₅)— | C(CH₃)₂C≡CH | H | O |
| (CH₃)₂C=CH— | C(CH₃)₂C≡CH | H | O |
| CH₂=C(CH₃)—CH(CH₃)— | C(CH₃)₂C≡CH | H | O |

TABLE 2-continued

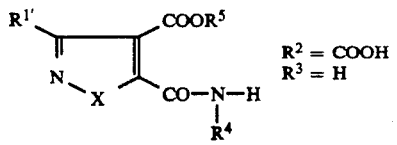

$R^2 = COOH$
$R^3 = H$

| $R^{1'}$ | $R^4$ | $R^5$ | x |
|---|---|---|---|
| $(CH_3)_2C=CH-CH_2-$ | $C(CH_3)_2C\equiv CH$ | H | O |
| $CH_3-CCl=CH-$ | $C(CH_3)_2C\equiv CH$ | H | O |
| $Cl_2C=CH-$ | $C(CH_3)_2C\equiv CH$ | H | O |
| cyclopent-1-ene | $C(CH_3)_2C\equiv CH$ | H | O |
| cyclohex-1-ene | $C(CH_3)_2C\equiv CH$ | H | O |
| 1-$CH_3$-cyclohex-2-ene | $C(CH_3)_2C\equiv CH$ | H | O |
| E-phenyl-$CH=CH-$ | $C(CH_3)_2C\equiv CH$ | H | O |
| E-4-$(CH_3O)-C_6H_5-CH=CH-$ | $C(CH_3)_2C\equiv CH$ | H | O |
| $HC\equiv C-$ | $C(CH_3)_2C\equiv CH$ | H | O |
| $CH_3-C\equiv C-$ | $C(CH_3)_2C\equiv CH$ | H | O |
| $HC\equiv C-CH_2$ | $C(CH_3)_2C\equiv CH$ | H | O |
| phenyl-$C\equiv C-$ | $C(CH_3)_2C\equiv CH$ | H | O |
| $CH_3-CH\underset{\diagdown O \diagup}{-}CH-$ | $C(CH_3)_2C\equiv CH$ | H | O |
| cyclopropyl-$CH(CH_3)-$ | $C(CH_3)_2C\equiv N$ | H | O |
| cyclopropyl-$CH(C_2H_5)-$ | $C(CH_3)_2C\equiv N$ | H | O |
| $CH_2=CH-$ | $C(CH_3)_2C\equiv N$ | H | O |
| E-$CH_3-CH=CH-$ | $C(CH_3)_2C\equiv N$ | H | O |
| Z-$CH_3-CH=CH$ | $C(CH_3)_2C\equiv N$ | H | O |
| $CH_2=CH-CH_2-$ | $C(CH_3)_2C\equiv N$ | H | O |
| $CH_2=C(CH_3)-$ | $C(CH_3)_2C\equiv N$ | H | O |
| $C_2H_5-CH=CH-$ | $C(CH_3)_2C\equiv N$ | H | O |
| $CH_3-CH=C(CH_3)-$ | $C(CH_3)_2C\equiv N$ | H | O |
| $CH_2=C(C_2H_5)-$ | $C(CH_3)_2C\equiv N$ | H | O |
| $CH_3-CH=C(C_2H_5)-$ | $C(CH_3)_2C\equiv N$ | H | O |
| $(CH_3)_2C=CH-$ | $C(CH_3)_2C\equiv N$ | H | O |
| $CH_2=C(CH_3)-CH(CH_3)-$ | $C(CH_3)_2C\equiv N$ | H | O |
| $(CH_3)_2C=CH-CH_2-$ | $C(CH_3)_2C\equiv N$ | H | O |
| $CH_3-CCl=CH-$ | $C(CH_3)_2C\equiv N$ | H | O |
| $Cl_2C=CH-$ | $C(CH_3)_2C\equiv N$ | H | O |
| cyclopent-1-ene | $C(CH_3)_2C\equiv N$ | H | O |
| cyclohex-1-ene | $C(CH_3)_2C\equiv N$ | H | O |
| 1-$CH_3$-cyclohex-2-ene | $C(CH_3)_2C\equiv N$ | H | O |
| E-phenyl-$CH=CH-$ | $C(CH_3)_2C\equiv N$ | H | O |
| E-4-$(CH_3O)-C_6H_5-CH=CH-$ | $C(CH_3)_2C\equiv N$ | H | O |
| $HC\equiv C-$ | $C(CH_3)_2C\equiv N$ | H | O |
| $CH_3-C\equiv C-$ | $C(CH_3)_2C\equiv N$ | H | O |
| $HC\equiv C-CH_2$ | $C(CH_3)_2C\equiv N$ | H | O |
| phenyl-$C\equiv C-$ | $C(CH_3)_2C\equiv N$ | H | O |
| $CH_3-CH\underset{\diagdown O \diagup}{-}CH-$ | $C(CH_3)_2C\equiv N$ | H | O |
| $CH_2=CH-$ | tert.-butyl | H | S |
| E-$CH_3-CH=CH-$ | tert.-butyl | H | S |
| E-$C_6H_5-CH=CH-$ | tert.-butyl | H | S |
| $CH_2=C(CH_3)-$ | tert.-butyl | H | S |
| $CH_2=CH-$ | cyclopropyl | H | S |
| E-$CH_3-CH=CH-$ | cyclopropyl | H | S |
| E-$C_6H_5-CH=CH$ | cyclopropyl | H | S |
| $CH_2=C(CH_3)-$ | cyclopropyl | H | S |
| cyclopropyl-$CH(CH_3)-$ | tert.-butyl | $-N=C(CH_3)_2$ | O |
| cyclopropyl-$CH(C_2H_5)-$ | tert.-butyl | $-N=C(CH_3)_2$ | O |
| $CH_2=CH-$ | tert.-butyl | $-N=C(CH_3)_2$ | O |
| E-$CH_3-CH=CH-$ | tert.-butyl | $-N=C(CH_3)_2$ | O |
| Z-$CH_3-CH=CH$ | tert.-butyl | $-N=C(CH_3)_2$ | O |
| $CH_2=CH-CH_2-$ | tert.-butyl | $-N=C(CH_3)_2$ | O |
| $CH_2=C(CH_3)-$ | tert.-butyl | $-N=C(CH_3)_2$ | O |
| $C_2H_5-CH=CH-$ | tert.-butyl | $-N=C(CH_3)_2$ | O |
| $CH_3-CH=C(CH_3)-$ | tert.-butyl | $-N=C(CH_3)_2$ | O |
| $CH_2=C(C_2H_5)-$ | tert.-butyl | $-N=C(CH_3)_2$ | O |
| $CH_3-CH=C(C_2H_5)-$ | tert.-butyl | $-N=C(CH_3)_2$ | O |
| $(CH_3)_2C=CH-$ | tert.-butyl | $-N=C(CH_3)_2$ | O |
| $CH_2=C(CH_3)-CH(CH_3)-$ | tert.-butyl | $-N=C(CH_3)_2$ | O |
| $(CH_3)_2C=CH-CH_2-$ | tert.-butyl | $-N=C(CH_3)_2$ | O |
| $CH_3-CCl=CH-$ | tert.-butyl | $-N=C(CH_3)_2$ | O |
| $Cl_2C=CH-$ | tert.-butyl | $-N=C(CH_3)_2$ | O |
| cyclopent-1-ene | tert.-butyl | $-N=C(CH_3)_2$ | O |
| cyclohex-1-ene | tert.-butyl | $-N=C(CH_3)_2$ | O |

TABLE 2-continued $$\begin{array}{c} R^{1'} \diagdown \phantom{xx} \diagup COOR^5 \\ \phantom{xx} \| \\ N \diagdown_X \diagdown CO-N-H \\ \phantom{xxxxxxxxx} | \\ \phantom{xxxxxxxxxx} R^4 \end{array} \quad \begin{array}{l} R^2 = COOH \\ R^3 = H \end{array}$$

| $R^{1'}$ | $R^4$ | $R^5$ | x |
|---|---|---|---|
| 1-CH$_3$-cyclohex-2-ene | tert.-butyl | —N=C(CH$_3$)$_2$ | O |
| E-phenyl-CH=CH— | tert.-butyl | —N=C(CH$_3$)$_2$ | O |
| E-4-(CH$_3$O)—C$_6$H$_5$—CH=CH— | tert.-butyl | —N=C(CH$_3$)$_2$ | O |
| HC≡C— | tert.-butyl | —N=C(CH$_3$)$_2$ | O |
| CH$_3$—C≡C— | tert.-butyl | —N=C(CH$_3$)$_2$ | O |
| HC≡C—CH$_2$ | tert.-butyl | —N=C(CH$_3$)$_2$ | O |
| phenyl-C≡C— | tert.-butyl | —N=C(CH$_3$)$_2$ | O |
| CH$_3$—CH(—O—)CH— | tert.-butyl | —N=C(CH$_3$)$_2$ | O |
| cyclopropyl-CH(CH$_3$)— | cyclopropyl | —N=C(CH$_3$)$_2$ | O |
| cyclopropyl-CH(C$_2$H$_5$)— | cyclopropyl | —N=C(CH$_3$)$_2$ | O |
| CH$_2$=CH— | cyclopropyl | —N=C(CH$_3$)$_2$ | O |
| E—CH$_3$—CH=CH— | cyclopropyl | —N=C(CH$_3$)$_2$ | O |
| Z—CH$_3$—CH=CH | cyclopropyl | —N=C(CH$_3$)$_2$ | O |
| CH$_2$=CH—CH$_2$— | cyclopropyl | —N=C(CH$_3$)$_2$ | O |
| CH$_2$=C(CH$_3$)— | cyclopropyl | —N=C(CH$_3$)$_2$ | O |
| C$_2$H$_5$—CH=CH— | cyclopropyl | —N=C(CH$_3$)$_2$ | O |
| CH$_3$—CH=C(CH$_3$)— | cyclopropyl | —N=C(CH$_3$)$_2$ | O |
| CH$_2$=C(C$_2$H$_5$)— | cyclopropyl | —N=C(CH$_3$)$_2$ | O |
| CH$_3$—CH=C(C$_2$H$_5$)— | cyclopropyl | —N=C(CH$_3$)$_2$ | O |
| (CH$_3$)$_2$C=CH— | cyclopropyl | —N=C(CH$_3$)$_2$ | O |
| CH$_2$=C(CH$_3$)—CH(CH$_3$)— | cyclopropyl | —N=C(CH$_3$)$_2$ | O |
| (CH$_3$)$_2$C=CH—CH$_2$— | cyclopropyl | —N=C(CH$_3$)$_2$ | O |
| CH$_3$—CCl=CH— | cyclopropyl | —N=C(CH$_3$)$_2$ | O |
| Cl$_2$C=CH— | cyclopropyl | —N=C(CH$_3$)$_2$ | O |
| cyclopent-1-ene | cyclopropyl | —N=C(CH$_3$)$_2$ | O |
| cyclohex-1-ene | cyclopropyl | —N=C(CH$_3$)$_2$ | O |
| 1-CH$_3$-cyclohex-2-ene | cyclopropyl | —N=C(CH$_3$)$_2$ | O |
| E-phenyl-CH=CH— | cyclopropyl | —N=C(CH$_3$)$_2$ | O |
| E-4-(CH$_3$O)—C$_6$H$_5$—CH=CH— | cyclopropyl | —N=C(CH$_3$)$_2$ | O |
| HC≡C— | cyclopropyl | —N=C(CH$_3$)$_2$ | O |
| CH$_3$—C≡C— | cyclopropyl | —N=C(CH$_3$)$_2$ | O |
| HC≡C—CH$_2$ | cyclopropyl | —N=C(CH$_3$)$_2$ | O |
| phenyl-C≡C— | cyclopropyl | —N=C(CH$_3$)$_2$ | O |
| CH$_3$—CH(—O—)CH— | cyclopropyl | —N=C(CH$_3$)$_2$ | O |
| CH$_2$=CH— | tert.-butyl | —N=C(CH$_3$)$_2$ | S |
| E—CH$_3$—CH=CH— | tert.-butyl | —N=C(CH$_3$)$_2$ | S |
| E—C$_6$H$_5$—CH=CH— | tert.-butyl | —N=C(CH$_3$)$_2$ | S |
| CH$_2$=C(CH$_3$)— | tert.-butyl | —N=C(CH$_3$)$_2$ | S |
| CH$_2$=CH— | cyclopropyl | —N=C(CH$_3$)$_2$ | S |
| E—CH$_3$—CH=CH— | cyclopropyl | —N=C(CH$_3$)$_2$ | S |
| E—C$_6$H$_5$—CH=CH— | cyclopropyl | —N=C(CH$_3$)$_2$ | S |
| CH$_2$=C(CH$_3$)— | cyclopropyl | —N=C(CH$_3$)$_2$ | S |

3-Cyclopropylaminocarbonyl-5-isopropyl-isoxazole-4-carboxylic acid is particularly preferred.

The carboxamides Ia, Ib, Ic and Id, or herbicidal agents containing them, may be applied for instance in the form of directly sprayable solutions, powders, suspension (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as toluene, xylene, paraffin, tetrahydronaphthalene, alkylated naphthalenes and their derivatives, methanol, ethanol, propanol, butanol, cyclohexanol, cyclohexanone, chlorobenzene, isophorone, etc., and strongly polar solvents such as N,N-dimethylformamide, dimethyl sulfoxide, N-methylpyrrolidone, water, etc. are suitable.

Aqueous formulations may be prepared from emulsion concentrates, pastes, oil dispersions, wettable powders or water-dispersible granules by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of aromatic sulfonic acids, e.g., ligninsulfonic acid, phenolsulonic acid, naphthalene sulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadeconals, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica, gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

The formulations contain from 0.1 to 95, and preferably 0.5 to 90, % by weight of active ingredient. The active ingredients are used in a purity of 90 to 100, and preferably from 95 to 100, % (according to the NMR spectrum).

Examples of formulations are as follows:

I. 90 parts by weight of compound no. 3.002 is mixed with 10 parts by weight of N-methyl-alpha-pyrrolidone. A mixture is obtained which is suitable for application in the form of very fine drops.

II. 20 parts by weight of compound no. 3.006 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 3.016 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into 100,000 parts by weight of water, an aqueous dispersion is obtained containing 0.02% by weight of the active ingredient.

IV. 20 parts by weight of compound no. 3.020 is dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide and 1 mole of caste oil. By pouring the solution into 100,000 parts by weight of water, an aqueous dispersions is obtained containing 0.02% by weight of the active ingredient.

V. 20 parts by weight of compound no. 3.029 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 3.047 is intimately mixed with 97 parts by weight of particulate kaolin. A dust is obtained containing 3% by weight of the active ingredient.

VII. 30 parts by weight of compound no. 3.048 is intimately mixed with a mixture consisting of 92 parts by weight of powdered silica gel and 8 parts by weight of paraffin of which has been sprayed onto the surface of this silica gel. A formulation of the active ingredient is obtained having good adherence.

VIII. 40 parts by weight of compound no. 6.04 is dispersed in 10 parts by weight of the sodium salt of a phenosulfonic acid-urea-formaldehyde condensate, 2 parts by weight of silica gel and 48 parts by weight of water. The mixture may be further diluted.

IX. 20 parts by weight of compound no. 6.06 is intimately mixed with 2 parts of the calcium salt of dodecylbenzenesulfonic acid, 8 parts of a fatty alcohol polyglycol ether, 2 parts of the sodium salt of phenolsulfonic acid-urea-formaldehyde condensate and 68 parts of a paraffinic mineral oil. A stable oily dispersion is obtained.

X. 10 parts by weight of compound no. 6.08, 4 parts by weight of the sodium salt of diisobutylnaphthalene-α-sulfonic acid, 20 parts by weight of the sodium salt of a lignin-sulfonic acid from a sulfite waste liquor, 38 parts by weight of silica gel and 38 parts by weight of kaolin are triturated in a hammer mill. By finely distributing the mixture in 10,000 parts by weight of water a spray liquor is obtained containing 0.1 wt % of the active ingredient.

The active ingredients or the herbicidal agents containing them may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates depend on the objective to be achieved, the time of the year, the plants to be combated and their growth stages, and range from 0.001 to 5, and preferably from 0.011 to 1, kg/ha.

In view of the numerous application methods possible, the compounds according to the invention, or agents containing them, may be used in a large number of crops for removing unwanted plants. The crops which follow are given by way of example:

| Botanical name | Common name |
|---|---|
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rapeseed |
| Brassica napus var. napobrassica | swedes |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass |
| Daucus carota | carrots |
| Elais guineensis | oil palms |
| Fragaria vesca | strawberries |
| Glycine max | soybeans |
| Gossypium hirsutum (Gossypium arboreum, Gossypium herbaceum, Gossypium vitifolium) | cotton |
| Helianthus annuus | sunflowers |
| Helianthus tuberosus | Jerusalem artichoke |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicotiana tabacum (N. rustica) | tobacco |
| Olea europaea | olive trees |
| Oryza sativa | rice |
| Panicum miliaceum | millet |
| Phaseolus lunatus | limabeans |
| Phaseolus mungo | mungbeans |
| Phaseolus vulgaris | snapbeans, green beans, dry beans |
| Pennisetum glaucum | pearl millet |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (S. vulgare) | sorghum |
| Sorghum dochna | sorgo |
| Spinacia oleracea | spinach |
| Theobroma cacao | cacao plants |
| Trifolium pratense | red clover |
| Triticum aestivum | wheat |

-continued

| Botanical name | Common name |
|---|---|
| Triticum durum | durum wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the carboxamides Ia, Ib, Ic and Id may be mixed with each other, or mixed and applied together with numerous representatives of other herbicidal or growth-regulating active ingredient groups. Examples of suitable components are diazines, 4-H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, quinolinecarboxylic acids, (hetero)-aryloxyphenoxypropionic acids and salts, esters, amides thereof, etc.

It may also be useful to apply compounds Ia, Ib, Ic and Id, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

EXAMPLES ILLUSTRATING THE SYNTHESIS OF COMPOUNDS Ia, Ib, Ic and Id

Example 1

3-tert-Butylaminocarbonyl-5-n-propylisoxazole-4-carboxylic acid (no. 3.013 in Table 3)

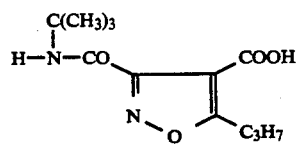

Under a nitrogen blanket and at $-70°$ C., 104.6 mmol of n-butyllithium (67.7 ml of a 1.5 molar solution in hexane) was dripped into a solution of 10.0 g (47.6 mmol) of 5-n-proylisoxazole-3-carboxylic acid-tert.-butylamide in 250 ml of anhydrous tetrahydrofuran, and the whole was stirred for 30 minutes at this temperature. The reaction mixture was then poured onto 500 g of solid $CO_2$ and left to stand overnight. The mixture was evaporated down, the residue was taken up in 300 ml of water and 20 ml of 2N NaOH followed by extraction with two times 100 ml of diethyl ether, the aqueous phase was acidified to pH 2 with 6N hydrochloric acid, followed by extraction four times, each time with 200 ml of ethyl acetate. The extracts were dried over magnesium sulfate and the solvent was removed under reduced pressure. Yield: 80%.

Preliminary stage 1α

5-n-Propylisoxazole-3-carboxylic acid-tert.-butylamide

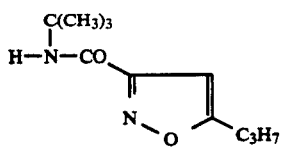

At 5° C., 9.3 g (126.8 mmol) of tert-butylamine in 20 ml of dichloromethane was dripped into 10.0 g (57.6 mmol) of 5-n-propyl-isoxazole-3-carboxylic chloride in 250 ml of anhydrous dichloromethane. The mixture was stirred for 12 hours at room temperature, 200 ml of water was added, the phases were separated, the organic phase was washed once with 150 ml of saturated sodium bicarbonate solution and once with 150 ml of saturated sodium chloride solution, followed by drying over magnesium sulfate and stripping off the solvent under reduced pressure. There was obtained 11.5 g (95%) of 5-n-propylisoxazole-3-carboxylic acid-tert-butylamide as a solid of melting point 34°–37° C.

The following isoxazole-3-carboxamides for example were synthesized analogously:

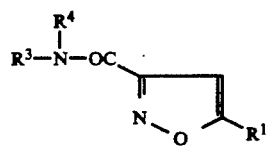

| $R^1$ | $R^3$ | $R^4$ | mp (°C.)/$^1$H-NMR (250 MHz; CDCl$_3$), δ in ppm |
|---|---|---|---|
| methyl | H | iso-propyl | 68–70 |
| methyl | H | tert.-butyl | 79–82 |
| methyl | H | cyclopropyl | 100–105 |
| methyl | H | phenyl | 132–135 |
| methyl | H | methyl | 122–126 |
| methyl | H | ethyl | 61–67 |
| n-propyl | H | tert.-butyl | 34–37 |
| iso-propyl | H | tert.-butyl | 78–79 |
| iso-propyl | H | cyclopropyl | 58–59 |
| n-butyl | H | tert.-butyl | 0.93(t; 3H), 1.40(m; 2H), 1.46(s; 9H), 1.70(m; 2H), 2.77(t; 3H), 6.40(s, 1H), 6.68(bs; 1H, NH) |
| n-butyl | H | cyclopropyl | 58–61 |
| sec.-butyl | H | tert.-butyl | 84–87 |
| sec.-butyl | H | cyclopropyl | 54–60 |
| tert.-butyl | H | tert.-butyl | 132–134 |
| tert.-butyl | H | cyclopropyl | 75–80 |
| phenyl | H | tert.-butyl | 131–133 |
| phenyl | H | cyclopropyl | 146–147 |
| 2,4-(Cl,Cl)-phenyl | H | tert.-butyl | 1.49(s; 9H), 6.70(bs, 1H, NH), 7.30(s; 1H), 7.25–7.90(m; 3H) |
| methoxyeth-1-yl | H | tert.-butyl | 1.48(s; 9H), 1.56(d; 3H), 3.34(s; 3H), 4.52(q; 1H), 6.63(s; 1H), 6.64(bs; 1H, NH) |
| methoxyeth-1-yl | H | cyclopropyl | 0.60–0.93(m; 4H), 1.54(d; 3H), 2.91(m; 1H), 3.38(s; 3H), 4.54(q; 1H), 6.68(s; 1H), 7.04(bs, 1H, NH) |
| methoxyeth-1-yl | H | sec.-butyl | 37–40 |
| methoxyeth-1-yl | H | cyclopropyl-methyl | 0.24–0.60(m; 4H), 1.09(m; 1H), 1.56(d; 3H), 3.34(m; 2H), 3.38(s; 3H), 4.58(q; 1H), 6.70(s; 1H), 7.30(bs; 1H, NH) |
| methoxymethyl | H | tert.-butyl | 1.46(s; 9H), 3.44(s; 3H), 4.60(s; 2H), 6.68(s; 1H), 6.68(bs; 1H, NH) |
| methoxymethyl | H | sec.-butyl | 0.96(t; 3H), 1.26(d; 3H), 1.58(m; 2H), 3.43(s; 3H), 4.10(m; 1H), 4.56(s; 2H), 6.70(bs; 1H, NH). 6.74(s; 1H) |
| 2-methyltetrahydro-pyran-2-yl | H | cyclopropyl | 60–62 |
| 2-methyltetrahydro-pyran-2-yl | H | 3-CF$_3$-phenyl | 1.54(s; 3H), 1.40–2.46(m; 6H), 3.56(m; 2H), 6.74(s; 1H), 6.75–8.00(m; 4H), 8.68(bs; 1H, NH) |
| 2-methyl-norbornan-2-yl* | H | cyclopropyl | 0.60–0.94(m; 4H), 1.18–2.42(m; 13H), 2.90(m; 1H), 6.42(s; 1H), 6.97(bs; 1H, NH) |
| 4-F-phenyl | H | tert.-butyl | 115–118 |
| 2,4,6-trimethylphenyl | H | tert.-butyl | 83–90 |
| cyclopropyl | H | neo-pentyl | 85–90 |
| cyclopropyl | H | 1,1-dimethyl-2-propenyl | 48–54 |
| cyclopropyl | H | benzyl | 89–93 |
| cyclopropyl | H | 2-methoxyethyl | 0.92–1.14(m; 4H), 2.09(m; 1H), 3.37(s; 1H), 3.58(m; 4H), 6.33(s; 1H), 7.11(bs; 1H, NH) |
| cyclopropyl | H | 2-propenyl | 42–46 |
| cyclopropyl | H | cyclopentyl | 86–92 |
| cyclohexyl | H | tert.-butyl | 98–100 |
| cyclohexyl | H | cyclopropyl | 134–136 |
| cyclohexyl | H | 1-cyclopropyl-ethyl | 117–122 |
| cyclopropyl | H | tert.-butyl | 80–84 |
| cyclopropyl | H | cyclopropyl | 92–98 |
| cyclopropyl | H | 1-cyclopropyl-ethyl | 60–64 |
| 1-methylcyclohexyl | H | tert.-butyl | 84–87 |
| 1-methylcyclohexyl | H | cyclopropyl | 0.60–0.91(m; 4H), 1.27(s; 3H), 1.29–2.10(m; 10H), 2.86(m; 1H), |

-continued

The following isoxazole-3-carboxamides for example were synthesized analogously:

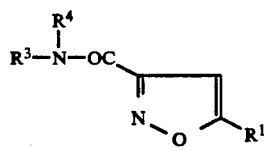

| R¹ | R³ | R⁴ | mp (°C.)/$^1$H-NMR (250 MHz; CDCl$_3$), δ in ppm |
|---|---|---|---|
| cyclopropyl | H | sec.-butyl | 6.47(s; 1H), 6.92(bs; 1H, NH) 70–77 |
| cyclopropyl | H | cyclopropyl methyl | 62–66 |
| methyl | H | 1-cyclopropyl-ethyl | 75 |
| cyclopropyl | H | cyclohexyl | 133–136 |
| 2-methyltetrahydro-pyran-2-yl | H | tert.-butyl | 72–76 |
| methyl | H | cyclobutyl | 100–103 |
| methyl | H | 1,1-dimethyl-propyl | 0.91(t; 3H), 1.41(s; 6H), 1.83(q; 2H), 2.48(s; 3H), 6.40 (s; 1H), 6.56(bs; 1H, NH) |
| methyl | H | neo-pentyl | 108–111 |
| 2-furanyl | H | tert.-butyl | 65–70 |
| 2-furanyl | H | cyclopropyl | 152–153 |
| methyl | H | sec.-butyl | 79–84 |
| methyl | H | 2-methoxy-ethyl | 2.48(s; 3H), 3.37(s; 3H), 3.57(m; 4H), 6.44(s; 1H), 7.17(bs; 1H, NH). 5.14(m; 2H), 6.09(m; 1H), 6.40(s; 1H), 6.77(bs; 1H, NH) |
| methyl | H | 1,1-dimethyl-2-propenyl | 1.54(s; 6H), 2.47(s; 3H) |
| methyl | H | cyclopentyl | 93–97 |

*1:1 exo:endo isomer mixture

EXAMPLE 2

3-tert.-Butylaminocarbonyl-5-n-propyl-isoxazole-4-carboxylic acid acetone oxime ester (No. 3.014 in Table 3)

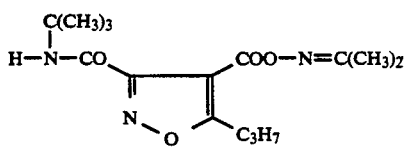

At room temperature, 4.9 g (48.1 mmol) of 4-methylmorpholine and 1.6 g (13.0 mmol) of 4-dimethylaminopyridine were dripped into a solution of 3.3 g (13.0 mmol) of 3-tert-butylaminocarbonyl-5-n-propyl-isoxazole-4-carboxylic acid (prepared as in Example 1) and 1.2 g (16.9 mmol) of acetonoxime in 100 ml of dichloromethane, and the mixture was stirred for 5 minutes. Subsequently, 11.3 g of a 50% strength solution of propanephosphonic anhydride in dichloromethane (=17.8 mmol) was added and the mixture was refluxed for 12 hours. After concentration, the residue was taken up in 100 ml of ethyl acetate, followed by extraction twice with saturated sodium bicarbonate solution, and once with 5% strength citric acid solution, once with saturated sodium carbonate solution and once with saturated sodium chloride solution. The organic phase was dried over magnesium sulfate and the solvent was stripped off under reduced pressure. Yield: 95%.

EXAMPLE 3

3-tert.-Butylaminocarbonyl-5-phenyl-isothiazole-4-carboxylic acid (No. 3.045 in Table 3)

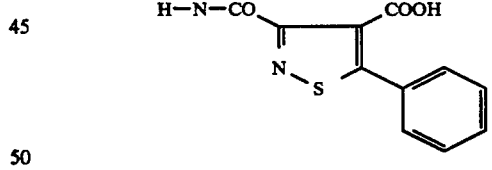

With ice cooling, 0.64 g (8.8 mmol) of tert-butylamine was dripped into 2.0 g (8.7 mmol) of 5-phenyl-isothiazole-3,4-dicarboxylic anhydride in 10 ml of dichloromethane, and the whole was stirred for 3 hours at room temperature. The solution was when evaporated down, 25 ml of water was added, and the solution was acidified to a pH of 2 with 6N HCl and extracted three times, each time with 30 ml of ethyl acetate. The organic phase was washed with 20 ml of saturated sodium chloride solution, dried over magnesium sulfate and evaporated down. The residue was chromatographed on silica gel (developer: ethanol/toluene 2:3). Yield: 49%.

EXAMPLE 4

5-Piperidinocarbonyl-3-methyl-isoxazole-4-carboxylic acid-tert.-butylamide (No. 5.001 in Table 5)

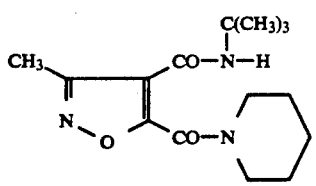

At −5° C. 1.8 g (25.1 mmol) of tert-butylamine, 7.2 g (71.6 mmol) of methylmorpholine, 0.8 g (6.4 mmol) of dimethylaminopyridine and 16.8 g of a 50% strength solution of propanephosphonic anhydride in dichloromethane (=26.4 mmol) were added one after the other to 4.6 g (19.3 mmol) of 5-piperidinocarbonyl-3-methyl-isoxazole-4-carboxylic acid in 100 ml of dichloromethane, and the mixture was stirred for 12 hours at room temperature. The solvent was stripped off under reduced pressure, and the residue was taken up in 200 ml of ethyl acetate, followed by extraction twice with saturated sodium bicarbonate solution, and once with 5% strength citric acid solution, once with saturated sodium carbonate solution, and once with saturated sodium chloride solution. The organic phase was dried over magnesium sulfate and the solvent stripped off under reduced pressure. Yield: 90%.

Preliminary stage 4α

Methyl 5-piperidinocarbonyl-3-methyl-isoxazole-4-carboxylate

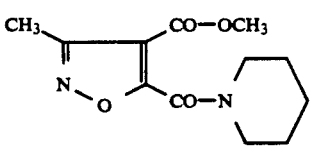

At −5° C., 3.0 g (35.1 mmol) of piperidine, 10.1 g (100.0 mmol) of methylmorpholine, 1.1 g (9 mmol) of dimethylaminopyridine and 22.9 g of a 50% strength solution of propanephosphonic anhydride in dichloromethane (36.0 mmol) were added one after the other to 5.0 g (27.0 mmol) of 4-methoxycarbonyl-3-methyl-isoxazole-5-carboxylic acid in 100 ml of dichloromethane, and the mixture was stirred for 12 hours at room temperature. The solvent was stripped off under reduced pressure, and the residue was taken up in 200 ml of ethyl acetate and extracted twice with saturated sodium bicarbonate solution and once with 5% strength citric acid solution and once with saturated sodium chloride solution. The organic phase was dried over magnesium sulfate and the solvent was stripped off under reduced pressure. Yield: 90%, $^1$H-NMR (250 MHz; CDCl$_3$): δ=1.65 ppm (m; 6H), 2.49 ppm (s; 3H), 3.18 ppm (m; 2H), 3.73 ppm (m; 2H), 3.87 ppm (s; 3H).

Preliminary stage 4β

5-Piperidinocarbonyl-3-methyl-isoxazole-4-carboxylic acid

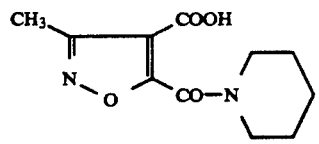

Under a nitrogen blanket and at −15° to −10° C., 1.0 g (25.0 mmol) of sodium hydroxide in 20 ml of water was dripped over a period of 4 hours into a solution of 5.7 g (22.6 mmol) of methyl 5-piperidinocarbonyl-3-methylisoxazole-4-carboxylate in 20 ml of methanol, and the mixture was stirred for 12 hours at room temperature. The solution was evaporated down, the residue was taken up in 100 ml of water, the pH was adjusted to 8-9, and the mixture was extracted once with 100 ml of diethyl ether. The mixture was acidified to a pH of 2 with 6N HCl, and extracted four times, each time with 100 ml of dichloromethane. The combined organic phases dried over magnesium sulfate and the solvent was stripped off under reduced pressure. Yield: 91%; mp.: 128°-130° C.

Example 5

4-tert.-Butylaminocarbonyl-3-methyl-isoxazole-5-carboxylic acid (No. 4.001 in Table 4)

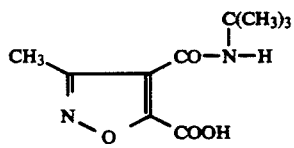

7.6 g (67.8 mmol) of potassium tert-butylate was added in portions to 3.3 g (11.3 mmol) of 5-piperidinocarbonyl-3-methyl-isoxazole-4-carboxylic acid-tert-butylamide (prepared as in Example 4) in 150 ml of diethyl ether and 0.4 g (22.2 mmol) of water, and the mixture was stirred for 6 hours at room temperature. After the addition of 50 ml of water and phase separation, the aqueous phase was acidified to a pH of 2 with HCl and extracted four times, each time with 100 ml of ethyl acetate. The combined organic phases were processed in conventional manner to give the product. The crude product was recrystallized from cyclohexane/ethyl acetate (5:1) Yield: 42%; colorless crystals.

Example 6

4-Cyclopropylamino-3-methyl-isothiazole-5-carboxylic acid (No. 4.006 in Table 4)

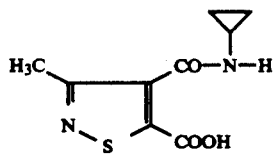

At −70° C. and under a nitrogen blanket, 60.0 mmol of n-butyllithium (40.0 ml of a 1-5 molar solution in hexane) was dripped into a solution of 5.2 g (28.6 mmol) of 3-methyl-isothiazole-4-carboxylic acid cyclopropylamide in 250 ml of tetrahydrofuran, and the mixture was stirred for 30 minutes at this temperature. The reaction mixture was poured onto 500 g of solid CO₂ and allowed to stand overnight. The mixture was evaporated down, the residue was taken up in 300 ml of water and 15 ml of 2N NaOH, extracted twice, each time with 100 ml of diethylether, and the aqueous phase was acidified to a pH of 2 with 6N hydrochloric acid and extracted four times, each time with 200 ml of ethyl acetate. Drying over magnesium sulfate and stripping off of the solvent under reduced pressure gave a yield of 74%.

Preliminary stage 6a

3-Methyl-isothiazole-4-carboxylic cyclopropylamide

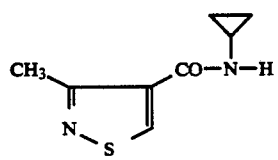

At −5° C., 3.7 g (65.0 mmol) of cyclopropylamine, 18.7 g (185.0 mmol) of methylmorpholine, 2.0 g (16.7 mmol) of dimethylaminopyridine and 43.5 g of a 50% strength solution of propanephosphonic anhydride in dichloromethane (=68.4 mol) were dripped one after the other into 7.2 g (50.0 mmol) of 3-methyl-isothiazole-4-carboxylic acid in 200 ml of dichloromethane, and the mixture was stirred for 12 hours at room temperature. The solvent was stripped off under reduced pressure, and the residue was taken up in 250 ml of ethyl acetate and extracted twice with saturated sodium bicarbonate solution and once with 5% strength citric acid solution, once with saturated sodium carbonate solution and once with saturated sodium chloride solution. The organic phase was dried over magnesium sulfate and the solvent was stripped off under reduced pressure. Yield: 84%; m.p.: 106°–108° C.

For instance the following isothiazole-4-carboxamides were synthesized analogously:

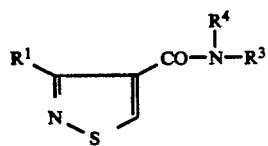

| R¹ | R³ | R⁴ | mp (°C.) |
|---|---|---|---|
| methyl | H | cyclopropyl | 106–108 |
| methyl | H | tert.-butyl | 96–97 |
| methyl | H | iso-propyl | 100–102 |
| iso-propyl | H | 3-CF₃-phenyl | 114–115 |
| iso-propyl | H | tert.-butyl | 158–159 |
| phenyl | H | cyclopropyl | 172–173 |
| phenyl | H | 4-Cl-phenyl | 202–203 |

EXAMPLE 7

4-Ethoxycarbonyl-5-methylisoxazole-3-carboxylic acid-tert.-butylamide (No. 3.036 in Table 3)

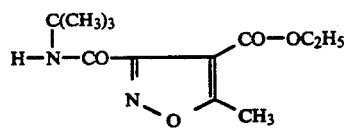

At room temperature, 12.7 g (106.8 mmol) of thionyl chloride was dripped into 10.6 g (53.3 mmol) of 4-ethoxycarbonyl-5-methylisoxazole-3-carboxylic acid in 150 ml of toluene and 2 ml of dimethylformamide, and the mixture was stirred for 1 hour at 80° C. The solvents were stripped off under reduced pressure, the residue was dissolved in 200 ml of anhydrous dichloromethane, and 10.0 g (137.0 mmol) of tert-butylamine in 20 ml of anhydrous dichloromethane. The mixture was stirred for 12 hours at room temperature, 200 ml of water was added, the organic phase was washed once with 150 ml of saturated sodium bicarbonate solution and once with 150 ml of saturated sodium chloride solution and dried over magnesium sulfate, and the solvent was stripped off under reduced pressure. Yield: 73%.

Preliminary stage 7a

Methyl 4-ethoxycarbonyl-5-methyl-isoxazole-3-carboxylate

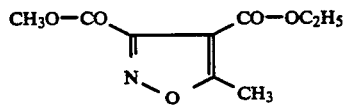

At room temperature, 39.0 g (0.3 mol) of ethyl acetoacetate in 100 ml of toluene was dripped into 9.9 g (0.33 mol) of NaH (80% strength suspension in white oil), and the mixture was stirred for 3 hours. Subsequently, 41.3 g (0.3 mol) of methyl-α-chloro-α-oximinoacetate in 100 ml of toluene was added and the mixture was stirred for 12 hours at room temperature. The reaction mixture was then transferred to a Soxhlet apparatus (extraction tube filled with 4 Å molecular sieve), 1 g of methanesulfonic acid was added and the mixture was refluxed for 1.5 hours. After the mixture had cooled, the organic phase was washed once with 200 ml of disodium bicarbonate solution and once with 200 ml of saturated sodium chloride solution and dried over magnesium sulfate, and the solvent was stripped off under reduced pressure.

Yield: 63%; yellow oil; ¹H-NMR (250 MHz; CDCl₃): δ=1.34 ppm (t; 3H), 2.73 ppm (s; 3H), 4.00 ppm (s; 3H), 4.32 ppm (q; 2H).

For example the following isoxazoledicarboxylic diesters were synthesized analogously:

| | | ¹H-NMR (250 MHz; CDCl₃) |
|---|---|---|
| R¹ | R⁵ | δ in ppm |
| CH₃ | CH₃ | 2.72(s; 3H), 3.87(s; 3H), 4.00(s; 3H) |
| CH₃ | C(CH₃)₃ | 1.52(s; 9H), 2.70(s; 3H), 4.00(s; 3H) |

-continued

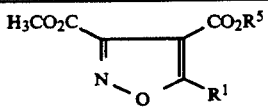

| R¹ | R⁵ | ¹H-NMR (250 MHz; CDCl₃) δ in ppm |
|---|---|---|
| CH₃ | C₂H₅ | 1.34(t; 3H), 2.73(s; 3H), 4.00(s; 3H), 4.32 (q; 2H) |
| CF₃ | C₂H₅ | 1.39(t; 3H), 4.06(s; 3H), 4.42(q; 2H) |
| (CH₃)₂CH | C₂H₅ | 1.34(t; 3H), 1.37(d; 6H), 3.73(sp; 1H), 4.00 (s; 3H), 4.29(q; 2H) |

Preliminary stage 7β

4-Ethoxycarbonyl-5-methylisoxazole-3-carboxylic acid

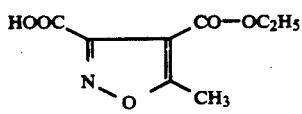

At −15° to −10° C. and under a nitrogen blanket, 4.7 g (0.117 mol) of sodium hydroxide in 80 ml of water was dripped into 25.0 g (0.117 mol) of methyl 4-ethoxycarbonyl-5-methylisoxazole-3-carboxylate in 200 ml of anhydrous tetrahydrofuran, and the mixture was stirred for 12 hours. The solvents were stripped off in a rotary evaporator (bath temperature: 30°-35° C.), the residue was taken up in 250 ml of water, the pH was adjusted to 8-9 with hydrochloric acid, and the mixture was extracted twice, each time with 150 ml of diethylether. The aqueous phase was acidified to a pH of 2 with 6N HCl and extracted four times, each time with 250 ml of ethyl acetate. The combined organic phases were dried over magnesium sulfate and the solvent was stripped off under reduced pressure. Yield: 70%; ¹H-NMR (250 MHz; CDCl₃); δ=1.42 ppm (t; 3H), 2.80 ppm (s; 3H), 4.59 ppm (q; 2H).

For example the following isoxazole-3-carboxylic acids were synthesized analogously:

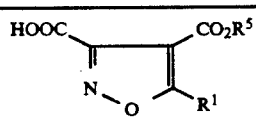

| R¹ | R⁵ | ¹H-NMR (250 MHz; CDCl₃) δ in ppm |
|---|---|---|
| CH₃ | C₂H₅ | 1.42(t; 3H), 2.80(s; 3H), 4.59(q; 2H) |
| CH₃ | C(CH₃)₃ | 1.54(s; 9H), 2.34(s; 3H), 13.80(bs; 1H) |
| CF₃ | C₂H₅ | 1.29(t; 3H), 4.15(q; 2H) |

EXAMPLE 8

3-tert.-Butylaminocarbonyl-5-methyl-isoxazole-4-carboxylic acid (No. 3.002 in Table 3)

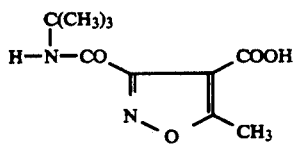

At from 5° to 10° C. and under a nitrogen blanket, 1.0 g (25.0 mmol) of sodium hydroxide in 50 ml of water was dripped into a solution of 5.4 g (21.3 mmol) of 4-ethoxycarbonyl-5-methyl-isoxazole-3-carboxylic acid-tert-butylamide in 100 ml of ethanol, and the mixture was stirred for 12 hours at room temperature. The solution was evaporated down, the residue was taken up in 150 ml of water, the pH was adjusted to 8-9, and the mixture was extracted twice, each time with 100 ml of diethylether. The aqueous phase was then acidified to a pH of 2 with 6N HCl, followed by extraction four times, each time with 200 ml of ethyl acetate. The combined organic phases were dried over magnesium sulfate and the solvent was stripped off under reduced pressure. Yield: 95%; yellow solid.

Example 9

Methyl 5-cyclopropylaminocarbonyl-3-isopropenylisoxazole-4-carboxylate (No. 6.02 in Table 6)

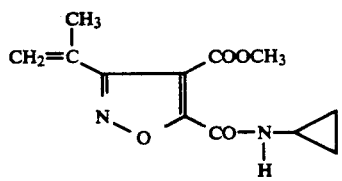

At 5° C., 3.1 g (0.0555 mol) of cyclopropylamine, 16.0 g (0.158 mol) of 4-methylmorpholine, 1.73 g (0.014 mol) of 4-dimethylaminopyridine and 37.0 g (0.058 mol) of a 50% strength solution of propanephosphonic anhydride in dichloromethane was dripped one after the other into a solution of 9.0 g (0.043 mol) of 3-isopropenyl-4-methoxycarbonylisoxazole-5-carboxylic acid in 200 ml of dichloromethane. After the mixture had been stirred for 12 hours at room temperature, the solvent was removed, the residue was taken up in 250 ml of ethyl acetate and the solution is extracted twice with saturated sodium bicarbonate solution and once with 5% strength citric acid solution, once with saturated sodium carbonate solution and once with saturated sodium chloride solution. After drying over magnesium sulfate, the solvent was distilled off under reduced pressure. Yield: 54%.

Preliminary stage 9a

Dimethyl E-3-styryl-isoxazole-4,5-dicarboxylate

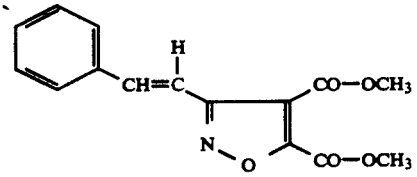

A mixture, cooled to 0° C., of 14.7 g (0.1 mol) of E-cinnamic aldehyde oxime, 1.8 g (0.01 mol) of disodium biphosphate dihydrate, 1.6 g (0.01 mol) of sodium dihydrogenphosphate dihydrate, 50 ml of dichloromethane and 50 ml of water was adjusted to a pH of 6.3 with hydrochloric acid/sodium hydroxide solution. After the addition of 14.2 g (0.1 mol) of dimethyl acetylenedicarboxylate, 61.2 g (0.11 mol) of a 13.4% strength aqueous sodium hypochlorite solution was dripped in over a period of one hour at 0°-10° C. and the pH was also kept constant by adding hydrochloric acid or sodium hydroxide solution. The mixture was then stirred for one hour at room temperature, the phases were separated and the aqueous phase was extracted twice, each time with 100 ml of dichloromethane. The combined organic phases were dried over sodium sulfate, the solvent was removed under reduced pressure and the more readily volatile components were distilled off at 120° C. (0.1 mm Hg). Yield: 56%; $^1$H-NMR (in CDCl$_3$): $\delta$=3.9 ppm (s; 3H), 4.0 ppm (s; 3H), 7.2 ppm (d; 1H), 7.3-7.7 ppm (m; 6H).

Analogously to Preliminary stage 9α dimethyl 3-isopropenylisoxazole-4,5-dicarboxylate was synthesized. Yield: 26%; $^1$H-NMR (in CDCl$_3$): $\delta$=2.2 ppm (s; 3H), 3.9 ppm (s; 3H), 4.0 ppm (s; 3H), 5.45 ppm (m; 2H).

Preliminary stage 9β

3-Isopropenyl-4-methoxycarbonylisoxazole-5-carboxylic acid

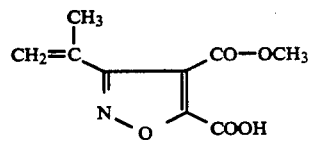

At 0° C., a solution of 3.6 g (0.09 mol) of sodium hydroxide in 75 ml of water was dripped into 20.0 g (0.09 mol) of dimethyl 3-isopropenylisoxazole-4,5-dicarboxylate (from stage A.1) in 150 ml of methanol, and the mixture was stirred for 14 hours at room temperature. 250 ml of water was added, the pH was adjusted to 8, extraction was effected with 200 ml of dichloroethane, and the aqueous phase was adjusted to a pH of 1-2 with 6N hydrochloric acid and extracted three times, each time with 250 ml of dichloromethane. The combined organic extracts were dried over magnesium sulfate and the solvent was distilled off under reduced pressure. Yield: 97%; $^1$H-NMR (in CDCl$_3$): $\delta$=2.12 ppm (s; 3H), 4.07 ppm (s; 3H), 5.41 ppm (m; 2H); 8.00 ppm (bs; 1H).

Example 10

5-Cyclopropylaminocarbonyl-3-isopropenylisoxazole-4-carboxylic acid (No. 6.05 in Table 6)

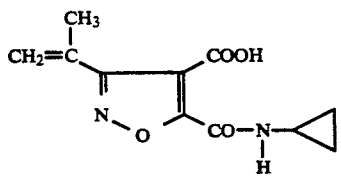

At 5° to 10° C., 0.68 g (0.017 mol) of sodium hydroxide was added to a solution of 4.0 g (0.016 mol) of methyl 5-cyclopropylaminocarbonyl-3-isopropenyl-4-carboxylate (prepared in accordance with Example 9) in 50 ml of methanol. After the mixture had been stirred for 12 hours at room temperature, the solvent was removed, the residue was taken up in 150 ml of water, and the mixture was adjusted to a pH of 8-9 and extracted twice, each time with 100 ml of diethyl ether. The aqueous phase was then acidified to a pH of 2 with 6N HCl and extracted four times, each time with 200 ml of ethyl acetate, the combined organic phases were dried over magnesium sulfate and the solvent was distilled off under reduced pressure. Yield: 74%.

Example 11

5-tert.-Butylaminocarbonyl-3-isopropenylisoxazole-4-carboxylic acid acetoxime ester (No. 6.08 in Table 6)

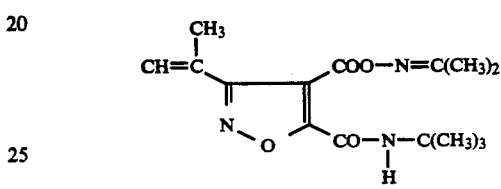

At room temperature, 5.9 g (0.059 mol) of 4-methylmorpholine and 1.94 g (0.016 mol) of 4-dimethylaminopyridine were dripped into a solution of 4.0 g (0.016 mol) of 5-tert.-butylaminocarbonyl-3-isopropenylisoxazole-4-carboxylic acid (no. 6.06 in Table 6) and 1.5 g (0.021 mol) of acetoxime in 200 ml of dichloromethane. After the mixture had been stirred for five minutes, 13.7 g (0.0215 mol) of a 50% strength solution of propanephosphonic anhydride in dichloromethane was added. After the mixture had been refluxed for 8 hours, the solvent was removed and the residue was dissolved in 100 ml of ethyl acetate and worked up as in Example 9. Yield: 55%.

The physical data of the end products (Examples 1 to 10) are given in Tables 3 to 7 below, which contain further compounds Ia, Ib, Ic and Id which were obtained (or are obtainable) in the same manner.

TABLE 3

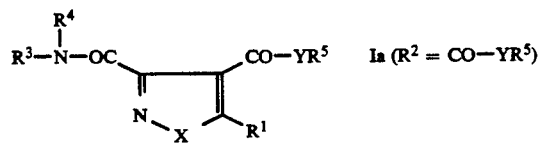

Ia ($R^2$ = CO—$YR^5$)

| No. | $R^1$ | $R^3$ | $R^4$ | $R^5$ | X | Y | mp. [°C.]/$^1$H-NMR (250 MHz, CDCl$_3$), $\delta$ in ppm |
|---|---|---|---|---|---|---|---|
| 3.001 | methyl | H | iso-propyl | H | O | O | 134–137 |
| 3.002 | methyl | H | tert.-butyl | H | O | O | 90–93 |
| 3.003 | methyl | H | cyclo-propyl | H | O | O | 120–125 |

TABLE 3-continued

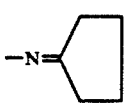

Ia ($R^2 = CO-YR^5$)

| No. | $R^1$ | $R^3$ | $R^4$ | $R^5$ | X | Y | mp. [°C.]/$^1$H-NMR (250 MHz, CDCl$_3$), δ in ppm |
|---|---|---|---|---|---|---|---|
| 3.004 | methyl | H | phenyl | H | O | O | 178-181 |
| 3.005 | methyl | H | tert.-butyl | $-N=C(CH_3)_2$ | O | O | 110-113 |
| 3.006 | methyl | H | tert.-butyl | succinimido | O | O | 172-178 |
| 3.007 | methyl | H | cyclo-propyl | $-N=C(CH_3)_2$ | O | O | 160-163 |
| 3.008 | methyl | H | methyl | H | O | O | 180-184 |
| 3.009 | methyl | H | ethyl | H | O | O | 130-134 |
| 3.010 | methyl | H | tert.-butyl | 2,4-Cl, Cl-phenyl | O | O | 134-137 |
| 3.011 | methyl | H | tert.-butyl | 2,3-OCH$_3$, OCH$_3$-phenyl | O | O | 170-173 |
| 3.012 | methyl | H | tert.-butyl | 4-OCH$_3$-phenyl | O | O | 141-143 |
| 3.013 | n-propyl | H | tert.-butyl | H | O | O | 1.00(t; 3H), 1.52(s; 9H), 1.80(m; 2H), 3.25(t; 2H), 7.17(bs; 1H, NH) |
| 3.014 | n-propyl | H | tert.-butyl | $-N=C(CH_3)_2$ | O | O | 95-96 |
| 3.015 | n-propyl | H | tert.-butyl | propargyl | O | O | 60-66 |
| 3.016 | iso-propyl | H | cyclo-propyl | H | O | O | 70-71 |
| 3.017 | iso-propyl | H | cyclo-propyl | $-N=C(CH_3)_2$ | O | O | 105-107 |
| 3.018 | iso-propyl | H | tert.-butyl | $-N=C(CH_3)_2$ | O | O | 139-143 |
| 3.019 | iso-propyl | H | tert.-butyl | H | O | O | 32-35 |
| 3.020 | n-butyl | H | cyclo-propyl | H | O | O | 0.94(t; 3H), 1.41(m; 2H), 1.49(s; 9H), 1.74(m; 2H), 3.27(t; 2H), 7.25(bs; 1H, NH) |
| 3.021 | n-butyl | H | cyclo-propyl | H | O | O | 74-77 |
| 3.022 | n-butyl | H | cyclo-propyl | $-N=C(CH_3)_2$ | O | O | 62-67 |
| 3.023 | tert.-butyl | H | tert.-butyl | H | O | O | 95-99 |
| 3.024 | tert.-butyl | H | tert.-butyl | $-N=C(CH_3)_2$ | O | O | 101-104 |
| 3.025 | tert.-butyl | H | cyclo-propyl | H | O | O | 70-72 |
| 3.026 | tert.-butyl | H | cyclo-propyl | $-N=C(CH_3)_2$ | O | O | 122-125 |
| 3.027 | sec.-butyl | H | tert.-butyl | H | O | O | 40 |
| 3.028 | sec.-butyl | H | cyclo-propyl | H | O | O | 0.80(m; 2H), 0.92(m; 2H), 0.90(t; 3H), 1.30(d; 3H), 1.77(m; 2H), 3.00(m; 1H), 4.00(m; 1H), 7.83(bs; 1H, NH) |
| 3.029 | sec.-butyl | H | tert.-butyl | $-N=C(CH_3)_2$ | O | O | 97-101 |
| 3.030 | sec.-butyl | H | cyclo-propyl | $-N=C(CH_3)_2$ | O | O | 0.66(m; 2H), 0.89(m; 2H), 0.90(t; 3H), 1.36(d; 3H), 1.72(m; 2H), 2.08 und 2.09 (2s; 6H), 2.92(m; 1H), 3.58(m; 1H), 7.25(bs; 1H, NH) |
| 3.031 | phenyl | H | tert.-butyl | H | O | O | 133-135 |
| 3.032 | phenyl | H | cyclo-propyl | H | O | O | 144-146 |
| 3.033 | phenyl | H | cyclo-propyl | $-N=C(CH_3)_2$ | O | O | 153-155 |
| 3.033 | phenyl | H | tert.-butyl | $-N=C(CH_3)_2$ | O | O | 131 |
| 3.035 | 2,4-Cl,Cl-phenyl | H | tert.-butyl | H | O | O | 1.54(s; 9H), 7.25(bs; 1H, NH), 7.20-7.90(m; 3H) |
| 3.036 | methyl | H | tert.-butyl | ethyl | O | O | 1.40(t; 3H), 1.48(s; 9H), 2.70(s; 3H), 4.37(q; 2H), 7.89(bs; 1H, NH) |
| 3.037 | iso-propyl | H | tert.-butyl | $-N=C(C_2H_5)(CH_3)$ | O | O | 107-112 |
| 3.038 | iso-propyl | H | tert.-butyl | 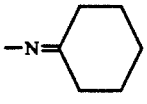 | O | O | 137-141 |
| 3.039 | iso-propyl | H | tert.-butyl |  | O | O | 114-117 |
| 3.040 | iso-propyl | H | tert.-butyl | $CH_2CH=CH-C_6H_5$ | O | O | 1.38(d; 6H), 1.44(s; 9H), 3.72(sp; 1H), 4.94(m; 2H), 6.20-6.90(m; 2H), 7.22-7.40 (m; 5H) |
| 3.041 | iso-propyl | H | tert.-butyl | $CH_2CCl_3$ | O | O | 68-71 |
| 3.042 | iso-propyl | H | tert.-butyl | $CH_2-CH_2-CN$ | O | O | 93-95 |
| 3.043 | iso-propyl | H | tert.-butyl | $CH_2CF_3$ | O | O | 73-76 |
| 3.044 | iso-propyl | H | tert.-butyl | 3-iodo-propargyl | O | O | 1.38(d; 6H), 1.44(s; 9H), |

TABLE 3-continued

Ia ($R^2$ = CO—$YR^5$)

| No. | $R^1$ | $R^3$ | $R^4$ | $R^5$ | X | Y | mp. [°C.]/$^1$H-NMR (250 MHz, CDCl$_3$), δ in ppm |
|---|---|---|---|---|---|---|---|
| | | | | | | | 3.70(sp; 1H), 4.40(m; 2H), 6.70(bs; 1H NH) |
| 3.045 | phenyl | H | tert.-butyl | H | S | O | >190 (decomp.) |
| 3.046 | iso-propyl | H | tert.-butyl | methyl | O | O | 123–124 |
| 3.047 | 1-methoxy-eth-1-yl | H | tert.-butyl | H | O | O | 1.55(d; 3H), 1.55(s; 9H); 3.35 (s; 3H); 5.46(q; 1H); 7.30(bs; 1H, NH) |
| 3.048 | 1-methoxy-eth-1-yl | H | cyclopropyl | H | O | O | 97–98 |
| 3.049 | 1-methoxy-eth-1-yl | H | sec.-butyl | H | O | O | 83–87 |
| 3.050 | 1-methoxy-eth-1-yl | H | cyclopropyl-methyl | H | O | O | 0.38(m; 2H); 0.63(m; 2H); 1.10 (m; 1H); 1.57(d; 3H); 3.38(s; 3H); 3.40(m; 2H); 5.46(q; 1H); 7.64(bs, 1H, NH) |
| 3.051 | 1-methoxy eth-1-yl | H | cyclopropyl-methyl | —N=C(CH$_3$)$_2$ | O | O | 96–99 |
| 3.052 | 1-methoxy eth-1-yl | H | tert.-butyl | —N=C(CH$_3$)$_2$ | O | O | 99–101 |
| 3.053 | 1-methoxy eth-1-yl | H | tert.-butyl | propargyl | O | O | 1.46(s; 9H); 1.58(d; 3H); 2.53 (t; 1H); 3.36(s; 3H); 4.91(d; 2H); 5.08(q; 1H); 6.67(bs, 1H, NH) |
| 3.054 | 1-methoxy eth-1-yl | H | cyclopropyl | —N=C(CH$_3$)$_2$ | O | O | 89–92 |
| 3.055 | 1-methoxy eth-1-yl | H | cyclopropyl | propargyl | O | O | 94–98 |
| 3.056 | 1-methoxy eth-1-yl | H | sec.-butyl | —N=C(CH$_3$)$_2$ | O | O | 76–79 |
| 3.057 | methoxymethyl | H | tert.-butyl | H | O | O | 1.52(s; 9H); 3.50(s; 3H); 5.05 (s; 2H); 7.26(bs; 1H, NH) |
| 3.058 | methoxymethyl | H | sec.-butyl | H | O | O | 50–56 |
| 3.059 | methoxymethyl | H | cyclopropyl | H | O | O | 56–62 |
| 3.060 | ethyl | H | cyclopropyl | Me | O | O | 0.58–0.96(m; 4H); 1.32(t; 3H); 2.90(m; 1H); 3.09(q; 2H); 3.91 (s; 3H); 7.91(bs, 1H, NH) |
| 3.061 | ethyl | H | cyclopropyl | H | O | O | 0.80–1.10(m; 4H); 1.30(t; 3H); 3.00(m; 1H); 3.26(q; 2H); 8.06 (bs, 1H, NH) |
| 3.062 | cyclohexyl | H | tert.-butyl | H | O | O | 126–129 |
| 3.063 | cyclohexyl | H | cyclopropyl | H | O | O | 140–144 |
| 3.064 | cyclohexyl | H | 1-cyclo-propyl-ethyl | H | O | O | 125–130 |
| 3.065 | cyclopropyl | H | tert.-butyl | H | O | O | 88–91 |
| 3.066 | cyclopropyl | H | cyclopropyl | H | O | O | 98–103 |
| 3.067 | cyclopropyl | H | 1-cyclo-propyl-ethyl | H | O | O | 55–60 |
| 3.068 | 1-methylcyclo-hexyl | H | tert.-butyl | H | O | O | 108–112 |
| 3.069 | 1-methylcyclo-hexyl | H | cyclopropyl | H | O | O | 102–107 |
| 3.070 | cyclopropyl | H | tert.-butyl | —N=C(CH$_3$)$_2$ | O | O | 150–152 |
| 3.071 | iso-propyl | H | tert.-butyl | ethyl | O | O | 69–72 |
| 3.072 | ethyl | H | cyclopropyl | —N=C(CH$_3$)$_2$ | O | O | 87–88 |
| 3.073 | cyclopropyl | H | cyclopropyl-methyl | H | O | O | 102–110 |
| 3.074 | cyclopropyl | H | sec.-butyl | H | O | O | 92–98 |
| 3.075 | cyclopropyl | H | cyclopropyl | H | O | O | 78–84 |
| 3.076 | cyclopropyl | H | cyclohexyl | H | O | O | 80–87 |
| 3.077 | 2-methyltetra-hydropyran-2-yl | H | tert.-butyl | H | O | O | 93–96 |
| 3.078 | 2-methyltetra-hydropyran-2-yl | H | cyclopropyl | H | O | O | 104–112 |
| 3.079 | 2-methyl-norbornan-2-yl | H | cyclopropyl | H | O | O | 133–136 |
| 3.080 | 4-F-phenyl | H | tert.-butyl | H | O | O | 93–96 |
| 3.081 | cyclopropyl | H | 1,1-dimethyl-2-propenyl | H | O | O | 1.24(m; 2H); 1.56(s; 6H); 3.20 (m; 1H); 5.20(m; 2H); 6.09(m; 1H); 7.26(bs; 1H NH) |
| 3.082 | cyclopropyl | H | benzyl | H | O | O | 145–159 |
| 3.083 | cyclopropyl | H | 2-methoxy-eth-1-yl | H | O | O | 91–96 |
| 3.084 | cyclopropyl | H | 2-propenyl | H | O | O | 109–114 |

TABLE 3-continued

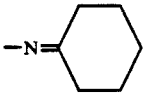

Ia ($R^2$ = CO—$YR^5$)

| No. | $R^1$ | $R^3$ | $R^4$ | $R^5$ | X | Y | mp. [°C.]/$^1$H-NMR (250 MHz, CDCl$_3$), δ in ppm |
|---|---|---|---|---|---|---|---|
| 3.085 | methyl | H | tert.-butyl | 2,4-(Br,Br) 4-CN-phenyl | O | O | 192–203 |
| 3.086* | methyl | H | tert.-butyl | —CH$_2$=CH=N—OC$_2$H$_5$ | O | O | main isomer: 1.24(t; 3H); 1.46(s; 3H); 2.68 (s; 3H); 4.16(m; 2H). 4.84(d; 2H); 7.08(bs; 1H, NH) 7.49(t; 1H) |
| 3.087 | methyl | H | tert.-butyl | Na$^⊕$ | O | O | 298–300 |
| 3.088 | methyl | H | tert.-butyl | K$^⊕$ | O | O | 256–257 |
| 3.089 | methyl | H | cyclobutyl | H | O | O | 119–124 |
| 3.090 | methyl | H | 1,1-dimethyl-propyl | H | O | O | 61–66 |
| 3.091 | methyl | H | tert.-butyl | NH$_4^⊕$ | O | O | 226–230 |
| 3.092 | methyl | H | tert.-butyl | —CH$_2$=CH=N—OCH$_3$ | O | O | 83–90 |
| 3.093 | methyl | H | tert.-butyl | 4-CN-phenyl | O | O | 119–125 |
| 3.094 | methyl | H | tert.-butyl | propargyl | O | O | 93–96 |
| 3.095 | methyl | H | 2,2-dimethyl-propyl | H | O | O | 125–129 |
| 3.096 | methyl | H | tert.-butyl | —N=⟨cyclohexyl⟩ | O | O | 124–127 |
| 3.097 | methyl | H | tert.-butyl | H$_3$N$^⊕$—CH(CH$_3$)$_2$ | O | O | 175–180 |
| 3.098 | 2-furanyl | H | tert.-butyl | H | O | O | 114–117 |
| 3.099 | 2-furanyl | H | cyclopropyl | H | O | O | 124–127 |
| 3.100 | methyl | H | tert.-butyl | —CH$_2$=CH=CH—C$_6$H$_5$ | O | O | |
| 3.101 | methyl | H | sec.-butyl | H | O | O | 78–83 |
| 3.102 | methyl | H | 2-methoxy-eth-1-yl | H | O | O | 74–77 |
| 3.103 | iso-propyl | H | cyclopropyl | Na$^⊕$ | O | O | 241 |
| 3.104 | iso-propyl | H | cyclopropyl | K$^⊕$ | O | O | 208–209 |
| 3.105 | methyl | H | 1,1-dimethyl-2-propenyl | H | O | O | 58–82 |
| 3.106 | iso-propyl | H | cyclopropyl | H$_3$N$^⊕$—CH(CH$_3$)$_2$ | O | O | 170–176 |
| 3.107 | iso-propyl | H | cyclopropyl | NH$_4^⊕$ | O | O | 221–223 |
| 3.108 | methyl | H | tert.-butyl | 2-Cl-phenyl | O | O | 168–170 |
| 3.109 | methyl | H | tert.-butyl | 3-Cl-phenyl | O | O | 125–128 |
| 3.110 | methyl | H | cyclopentyl | H | O | O | 99–104 |
| 3.111 | methyl | H | tert.-butyl | 4-Cl-phenyl | O | O | 112–117 |
| 3.112 | methyl | H | tert.-butyl | 4-F-phenyl | O | O | 173–176 |
| 3.113 | methyl | H | tert.-butyl | 4-CH$_3$-phenyl | O | O | 132–134 |
| 3.114 | methyl | H | tert.-butyl | 2-F-phenyl | O | O | 148–150 |
| 3.115 | methyl | H | tert.-butyl | phenyl | O | O | 152–157 |
| 3.116 | methyl | H | tert.-butyl | methyl | O | O | 129–132 |
| 3.117 | methyl | H | tert.-butyl | iso-propyl | O | O | 108–112 |
| 3.118 | methyl | H | tert.-butyl | tert.-butyl | O | S | 1.46(s; 9H); 1.60(s; 9H), 2.71 (s; 3H); 6.75(bs; 1H, NH) |
| 3.119 | methyl | H | tert.-butyl | cyclohexyl | O | O | 86–90 |
| 3.120 | 2,4,6-tri-methylphenyl | H | tert.-butyl | H | O | O | 1.53(s; 9H), 2.08(s; 3H), 2.10(s; 6H), 6.94(s; 2H), 7.30(bs; 1H, NH) |
| 3.121 | ethyl | methyl | ethyl | methyl | O | O | 1.17 and 1.27(2t; 3H+3H); 1.35(t; 3H); 2.89 and 3.12 (2s; 3H+3H); 3.18(q; 2H); 3.25 and 3.63(2q; 2H+2H); 3.84(s; 3H)*) |
| 3.122 | ethyl | methyl | ethyl | H | O | O | 1.27 and 1.30(2t; 3H+3H); 1.34(t; 3H), 3.18 and 3.28(2s; 3H+3H); 3.24(q; 2H), 3.67 and 3.68(2q; 2H+2H)*) |
| 3.123 | methyl | H | cyclopropyl | methyl | O | O | 0.60–0.92(m; 4H); 2.70(s; 3H); 2.93(m; 1H); 3.92(s; 3H); 8.27 (bs; 1H. NH) |
| 3.124 | iso-propyl | H | cyclopropyl | methyl | O | O | 0.60–0.93(m; 4H); 1.36(d; 6H); 2.92(m; 1H): 3.70(sp; 1H); 3.89 (s; 3H); 7.84(bs; 1H, NH) |
| 3.125 | ethyl | H | tert.-butyl | methyl | O | O | 1.32(t; 3H); 1.48(s; 9H); 3.09 (q; 2H); 3,88(s; 3H); 7.23(bs; 1H, NH) |
| 3.126 | ethyl | H | tert.-butyl | H | O | O | 1.36(t; 3H); 1.52(s; 9H); 3.28 |

*isomer mixture

TABLE 3-continued

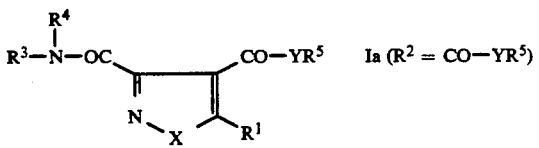

| No. | R¹ | R³ | R⁴ | R⁵ | X | Y | mp. [°C.]/¹H-NMR (250 MHz, CDCl₃), δ in ppm |
|---|---|---|---|---|---|---|---|
| | | | | | | | (q; 2H); 7.22(bs; 1H, NH) |

*)mixture of 2 rotamers

TABLE 4

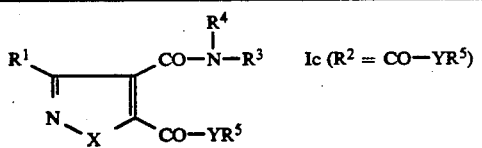

| No. | R¹ | R³ | R⁴ | R⁵ | X | Y | mp. [°C.]/¹H-NMR (250 MHz, CDCl₃), δ in ppm |
|---|---|---|---|---|---|---|---|
| 4.001 | methyl | H | tert.-butyl | H | O | O | 142–147 |
| 4.002 | ethyl | H | tert.-butyl | H | O | O | 124–127 |
| 4.003 | iso-propyl | H | tert.-butyl | H | O | O | 142–145 |
| 4.004 | iso-propyl | H | cyclopropyl | H | O | O | 136–138 |
| 4.005 | methyl | H | tert.-butyl | H | S | O | 134 |
| 4.006 | methyl | H | cyclopropyl | H | S | O | 131 |
| 4.007 | methyl | H | iso-propyl | H | S | O | 111 |
| 4.008 | methyl | H | tert.-butyl | —N=C(CH₃)₂ | S | O | 116–117 |
| 4.009 | iso-propyl | H | 3-CF₃-phenyl | H | S | O | 144 |
| 4.010 | iso-propyl | H | tert.-butyl | H | S | O | 164 |
| 4.011 | iso-propyl | H | tert.-butyl | —N=C(CH₃)₂ | S | O | 166–167 |
| 4.012 | phenyl | H | 4-Cl-phenyl | H | S | O | 169 |
| 4.013 | phenyl | H | cyclopropyl | H | S | O | 167 |
| 4.014 | phenyl | H | cyclopropyl | —N=C(CH₃)₂ | S | O | 148–149 |
| 4.015 | iso-propyl | H | tert.-butyl | methyl | S | O | 133–134 |
| 4.016 | methyl | H | 2,4,6-trimethylphenyl | —N=C(CH₃)₂ | O | O | 135 |
| 4.017 | iso-propyl | H | tert.-butyl | methyl | O | O | 121–123 |

TABLE 5

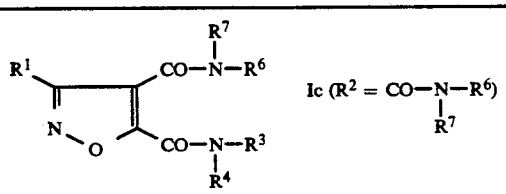

| No. | R¹ | R³ R⁴ | R⁶ R⁷ | mp. [°C.]/¹H-NMR (250 MHz, CDCl₃), δ in ppm |
|---|---|---|---|---|
| 5.01 | methyl | —(CH₂)₅— | H tert.-butyl | 74–75 |
| 5.02 | 4-F-phenyl | —(CH₂)₅— | H tert.-butyl | 1.40(s; 9H), 1.73(m; 6H), 3.40(m; 2H), 3.73(m; 2H), 7.14(m; 2H), 7.59(bs; 1H, NH), 7.73(m; 2H) |
| 5.03 | iso-propyl | H tert.-butyl | H tert.-butyl | 111–114 |
| 5.04 | methyl | H tert.-butyl | H H | 155–158 |
| 5.05 | ethyl | —(CH₂)₅— | H tert.-butyl | 1.34(t; 3H), 1.41(s; 9H), 1.50–1.80(m; 6H), 3.00(q; 2H), 3.34–3.43(m; 2H), 3.68—3.76 (m; 2H), 8.10(bs; 1H, NH) |
| 5.06 | iso-propyl | —(CH₂)₅— | H tert.-butyl | 76–77 |
| 5.07 | iso-propyl | —(CH₂)₅— | H cyclopropyl | 50–52 |
| 5.08 | cyclopropyl | —(CH₂)₅— | H tert.-butyl | 65 |
| 5.09 | methyl | H cyclopropyl | H cyclopropyl | 110–114 |

TABLE 6

$$\text{Id } (R^2 = CO-YR^5)$$

structure: R^{1'} with COYR^5, N-O ring, CO-N(R^3)(R^4)

| No. | $R^1$ | $R^3$ | $R^4$ | $R^5$ | Y | mp. [°C.]/$^1$H-NMR (250 MHz, CDCl$_3$), δ [ppm] |
|---|---|---|---|---|---|---|
| 6.01 | $CH_2=C(CH_3)-$ | H | iso-propyl | methyl | O | 1.29(d; 6H), 2.12(bs; 3H), 3.94(s; 3H) 4.26(sp; 1H) 5.42(m; 2H), 8.05(bs; 1H, NH) |
| 6.02 | $CH_2=C(CH_3)-$ | H | cyclopropyl | methyl | O | 0.63–0.92(m; 4H), 2.10(bs; 3H), 2.93(m; 1H), 3.93(s; 3H) 5.40(m; 2H), 8.40(bs; 1H, NH) |
| 6.03 | $CH_2=C(CH_3)-$ | H | tert.-butyl | methyl | O | 1.48(s; 9H), 2.1(bs; 3H), 3.93(s; 3H) 5.40 (m; 2H), 8.07(bs; 1H, NH) |
| 6.04 | $CH_2=C(CH_3)-$ | H | iso-propyl | H | O | 84–87 |
| 6.05 | $CH_2=C(CH_3)-$ | H | cyclopropyl | H | O | 96–100 |
| 6.06 | $CH_2=C(CH_3)-$ | H | tert.-butyl | H | O | 1.55(s; 9H), 2.15(bs; 3H), 5.40(m; 2H) 7.15(bs; 1H, NH) |
| 6.07 | $CH_2=C(CH_3)-$ | H | $-C(CH_3)_2C\equiv CH$ | H | O | 1.82(s; 6H), 2.17(bs; 3H), 2.53(s; 1H), 5.40(m; 2H), 7.43(bs; 1H, NH) |
| 6.08 | $CH_2=C(CH_3)-$ | H | tert.-butyl | $-N=C(CH_3)_2$ | O | 1.44(s; 9H), 2.07 und 2.10(2s; 6H) 2.17 (s; 3H), 5.42(m; 2H), 8.17(bs; 1H, NH) |
| 6.09 | $E-C_6H_5-CH=CH-$ | H | tert.-butyl | methyl | O | 1.48(s; 9H), 4.00(s; 3H), 7.12–7.61 (m; 7H), 9.13(bs; 1H, NH) |
| 6.10 | $E-C_6H_5-CH=CH$ | H | tert.-butyl | H | O | 75–80 |
| 6.11 | $CH_2=C(CH_3)-$ | H | $-C(CH_3)_2C\equiv CH$ | methyl | O | 1.78(s; 6H), 2.10 (s; 3H), 2.41(s; 1H) 3.93(s; 3H), 5.41(m; 2H), 8.63(bs; 1H, NH) |
| 6.12 | $CH_2=C(C_2H_5)-$ | H | tert.-butyl | H | O | 80–81 |
| 6.13 | $CH_2=C(C_2H_5)-$ | H | $-C(CH_3)_2C\equiv CH$ | H | O | 1.08(t; 3H), 1.80(s; 6H), 2.48(m; 2H), 2.50 (s; 1H), 5.30 and 5.44(2s; 2H), 7.50(bs; 1H, NH) |
| 6.14 | $CH_2=C(C_2H_5)-$ | H | cyclopropyl | H | O | 73–74 |
| 6.15 | $CH_2=C(C_2H_5)-$ | H | cyclopropyl | $-N=C(CH_3)_2$ | O | 48–52 |
| 6.16 | $CH_2=C(i-C_3H_7)-$ | H | tert.-butyl | H | O | 114–117 |
| 6.17 | $E-CH_3-CH=CH-$ | H | tert.-butyl | H | O | 64–69 |
| 6.18 | $CH_2=C(i-C_3H_7)-$ | H | tert.-butyl | $-N=C(CH_3)_2$ | O | 1.10(d; 6H), 1.48(s; 9H), 2.02 and 2.12(2s; 6H), 2.70(m; 1H), 5.34 and 5.41(2s; 2H), 8.36 (bs; 1H, NH) |
| 6.19 | $E-CH_3-CH=CH-$ | H | tert.-butyl | $-N=C(CH_3)_2$ | O | 78–82 |
| 6.20 | $CH_2=C(i-C_3H_7)-$ | H | tert.-butyl | methyl | O | 1.12(d; 6H), 1.48(s; 9H), 2.66(m; 1H), 3.90 (s; 3H), 5.24 and 5.39(2s; 2H), 8.50(bs; 1H, NH) |
| 6.21 | $CH_2=C(i-C_3H_7)-$ | H | cyclopropyl | methyl | O | 0.60–0.94(m; 4H), 1.11(d; 6H), 2.64(m; 1H), 3.00(m; 1H), 3.88(s; 3H), 5.24 and 5.39(2s; 2H), 8.87(bs; 1H, NH) |
| 6.22 | $E-CH_3-CH=CH-$ | H | tert.-butyl | methyl | O | 1.48(s; 9H), 1.95(dd; 3H), 3.94(s; 3H), 6.43–6.79(m; 2H), 9.07(bs; 1H, NH) |

TABLE 7

$$\text{Ib } (R^2 = CO-YR^5)$$

| No. | $R^1$ | $R^3$ | $R^4$ | $R^5$ | Y | Y | mp. [°C.]/$^1$H-NMR (250 MHz, CDCl$_3$), δ in ppm |
|---|---|---|---|---|---|---|---|
| 7.01 | methyl | H | tert.-butyl | methyl | O | O | 97–99 |
| 7.02 | methyl | H | tert.-butyl | H | O | O | 152–154 |
| 7.03 | iso-propyl | H | tert.-butyl | $-N=C(CH_3)_2$ | O | O | 58–61 |

USE EXAMPLES

The herbicidal action of the carboxamides of the formulae Ia', Ib', Ic' and Id is demonstrated in greenhouse experiments:

The vessels employed were plastic flowerpots having a volume of 300 cm$^3$ and filled with a sandy loam containing about 3.0% humus. The seeds of the test plants were sown separately, according to species.

For the preemergence treatment, the active ingredients, suspended or emulsified in water, were applied to the surface of the soil immediately after the seeds had been sown. The vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were grown, depending on growth form, to a height of 3 to 15 cm before being treated with compounds, suspended or emulsified in water. The application rate for postemergence treatment was 1.0 kg/ha.

The pots were set up in the greenhouse, heat-loving species at 20° to 35° C., and species from moderate climates at 10° to 25° C. The experiments were run for from 2 to 4 weeks. During this period the plants were tended and their reactions to the various treatments assessed. The assessment scale was 0 to 100, 100 denoting nonemergence or complete destruction of at least the visible plant parts, and 0 denoting no damage or normal growth.

The plants used in the experiments were Cassia tora, Chenopodium album, Chrysanthemum coronarium, Ipomoea spp., Polygonum persicaria, Stellaria media and Triticum aestivum.

Compounds 3.002, 3.005, 3.006, 3.008, 3.016, 3.017, 3.018, 3.019, 3.020, 3.023, 3.028, 3.029, 3.037. 3.052, 3.053, 6.04, 6.05, 6.06 and 6.08, applied postemergence at a rate of 1 kg/ha, provided excellent control of unwanted broadleaved plants. The carboxamides 3.006, 3.016 to 3.020, 3.028, 3.029, 3.037, 3.052, 3.053, 6.04, 6.05, 6.06 and 6.08 were also well tolerated by graminaceous crops such as wheat, Indian corn and rice.

We claim:

1. A carboxamide of the formula Ia, Ic or Id

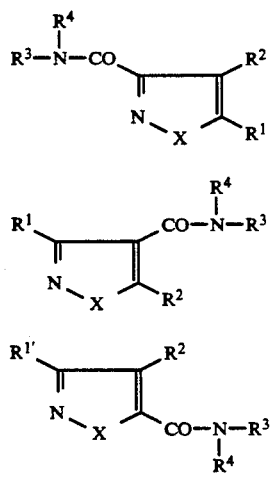

where

X is oxygen;

$R^1$ is hydrogen, halogen, $C_1$–$C_6$-alkyl which may carry from one to five halogen atoms or a cyano radical or one to two $C_1$–$C_4$-alkoxy groups;

$C_1$–$C_4$-alkoxy or $C_1$–$C_4$-alkylthio;

benzyl which may be monosubstituted, disubstituted or trisubstituted by $C_1$–$C_4$-alkyl, partially or fully halogenated $C_1$–$C_4$-alkyl, $C_1$–$C_4$-alkoxy, halogen, cyano or nitro;

phenyl which may also carry from one to three of the following radicals: cyano, nitro, halogen, $C_1$–$C_6$-alkyl, partially or fully halogenated $C_1$–$C_6$-alkyl, $C_1$–$C_6$-alkoxy, $C_1$–$C_6$-alkylthio;

phenoxy or phenylthio, each of which may be monosubstituted, disubstituted or trisubstituted by $C_1$–$C_4$-alkyl, partially or fully halogenated $C_1$–$C_4$-alkyl, $C_1$–$C_4$-alkoxy, $C_1$–$C_4$-alkylthio, halogen, cyano or nitro;

a 5- to 6-membered saturated or aromatic heterocyclic radical selected from the group consisting of 2-tetrahydrofuranyl, 3-tetrahydrofuranyl, 2-tetrahydrothienyl, 3-tetrahydrothienyl, 2-tetrahydropyranyl, 3-tetrahydropyranyl, 4-tetrahydropyranyl, 2-furanyl, 3-furanyl, 2-thienyl, or 3-thienyl, which may carry one or two of the following substituents: halogen, $C_1$–$C_3$-alkyl, $C_1$–$C_3$-alkoxy and $C_1$–$C_3$-alkoxycarbonyl;

$C_3$–$C_6$-cycloalkyl-substituted $C_1$–$C_6$-alkyl;

$C_2$–$C_6$-alkenyl whose double bond may be epoxidized, or $C_2$–$C_6$-alkynyl, it being possible for both groups to be monosubstituted, disubstituted or trisubstituted by halogen, $C_1$–$C_3$-alkoxy and/or monosubstituted by cyclopropyl or phenyl, it also being possible for the phenyl radical to carry up to three of the following substituents: halogen or $C_1$–$C_4$-alkyl;

$C_3$–$C_8$-cycloalkyl or $C_3$–$C_6$-cycloalkenyl, it being possible for both groups to be monosubstituted, disubstituted or trisubstituted by $C_1$–$C_4$-alkyl or halogen;

$R^1$ is $C_3$–$C_8$-cycloalkyl-substituted $C_1$–$C_6$-alkyl;

$C_2$–$C_6$-alkenyl whose double bond may be epoxidized, or $C_2$–$C_6$-alkynyl, it being possible for both groups to be monosubstituted, disubstituted or trisubstituted by halogen, $C_1$–$C_3$-alkoxy and/or monosubstituted by cyclopropyl or phenyl, it also being possible for the phenyl radical to carry up to three of the following substituents: halogen or $C_1$–$C_4$-alkyl;

$C_3$–$C_6$-cycloalkenyl, which may be monosubstituted, disubstituted or trisubstituted by halogen or $C_1$–$C_4$-alkyl;

$R^2$ is formyl, 4,5-dihydrooxazol-2-yl, $COYR^5$ or $CONR^6R^7$, where

Y is oxygen or sulfur;

$R^5$ is hydrogen;

$C_1$–$C_6$-alkyl which may carry from one to five halogen atoms and/or up to three hydroxyl and/or $C_1$–$C_4$-alkoxy groups and/or one of the following radicals;

cyano, $C_1$–$C_4$-alkoxy-$C_2$–$C_4$-alkoxy, $C_1$–$C_3$-alkylthio, $C_1$–$C_3$-alkylamino, di($C_1$–$C_3$)-alkylamino, $C_3$–$C_6$-cycloalkylamino or di($C_3$–$C_6$)-cycloalkylamino, trimethylsilyl, $C_1$–$C_3$-alkylsulfinyl or $C_1$–$C_3$-alkylsulfonyl, carboxyl, $C_1$–$C_3$-alkoxycarbonyl, $C_1$–$C_3$-alkoxycarbonyl-$C_1$–$C_3$-alkoxy or $C_1$–$C_3$-alkoxycarbonyl-$C_1$–$C_3$-alkoxy-$C_1$–$C_3$-alkoxycarbonyl, di($C_1$–$C_3$)-alkylaminocarbonyl, di($C_1$–$C_3$)-alkoxyphosphonyl, $C_1$–$C_6$-alkaneiminoxy or $C_5$–$C_6$-cyloalkaneiminoxy, N-phthalimido, N-succinimido, benzyloxy, benzoyl, it being possible for these cyclic radicals to additionally carry from one to three of the following groups: halogen, $C_1$–$C_3$alkyl or $C_1$–$C_3$-alkoxy, phenyl, which may also carry up to three of the following substituents: halogen, nitro, cyano, $C_1$–$C_3$-alkyl, partially or fully halogenated $C_1$–$C_3$-alkyl, $C_1$–$C_3$-alkoxy or partially or fully halogenated $C_1$–$C_3$-alkoxy;

—$CR^{10}$=N—$R^{11}$, where $R^{10}$ is hydrogen or $C_1$–$C_6$-alkyl and $R^{11}$ is $C_1$–$C_6$-alkoxy, $C_3$–$C_6$-alkenyloxy or $C_3$–$C_6$-alkynyloxy, each of which may carry up to 3 halogen atoms and/or a phenyl radical with, if desired, up to three of the following radicals: halogen, nitro cyano, $C_1$–$C_3$-alkyl or $C_1$–$C_3$-alkoxy; phenoxy, which may also carry up to three of the following substituents: halogen, nitro, cyano, $C_1$–$C_3$-alkyl or $C_1$–$C_3$-alkoxy; $C_1$–$C_6$-alkylamino, di($C_1$–$C_6$)alkylamino or phenylamino, it being possible for the aromatic ring to additionally carry up to three of the following radicals; halogen, nitro, cyano, $C_1$–$C_3$-alkyl or $C_1$–$C_3$-alkoxy;

$C_3$–$C_8$-cycloalkyl;

$C_3$–$C_6$-alkenyl, $C_5$–$C_6$-cycloalkyenyl, $C_3$–$C_6$-alkynyl, it being possible for these radicals to carry one of the following groups: hydroxyl, halogen, $C_1$–$C_4$-alkoxy or phenyl, it being possible for the aromatic radical to itself carry from one to three of the following groups: halogen, nitro, cyano, $C_1$–$C_4$-alkyl, phenyl, which may carry from one to three of the following groups: halogen, nitro, cyano, $C_1$–$C_4$-alkyl, partially or fully halogenated $C_1$–$C_4$-alkyl, $C_1$–$C_4$-alkoxy, partially or fully halogenated $C_1$–$C_4$-alkoxy or $C_1$–$C_4$-alkoxycarbonyl;

N-phthalimido, tetrahydrophthalimido, succinimido, maleiimido;

2,2-dimethyl-1,3-dioxolan-4-ylmethyl or 1,3-dioxolan-2-on-4-ylmethyl;

in the case where Y=O: one equivalent of a cation from the group comprising the alkali and alkaline earth metals, manganese, copper, iron, ammonium and ammonium which is substituted by up to 4 $C_1$–$C_3$-alkyl groups; or —N=$CR^8R^9$, where $R^8$ and $R^9$ are hydrogen; $C_1$–$C_4$-alkyl, which may be unsubstituted or partially or fully halogenated and may carry a $C_1$–$C_3$-alkoxy or phenyl radical, it being possible for the aromatic radical to itself also be monosubstituted, disubstituted or trisubstituted by halogen, nitro, cyano, $C_1$–$C_3$-alkyl, partially or fully halogenated $C_1$–$C_3$-alkyl, $C_1$–$C_3$-alkoxy or partially or fully halogenated $C_1$–$C_3$-alkoxy; $C_3$–$C_6$-cycloalkyl; $C_1$–$C_4$-alkoxy; furanyl or phenyl, which may additionally carry up to three of the following substituents: halogen, nitro, cyano, $C_1$–$C_3$-alkyl, partially or fully halogenated $C_1$–$C_3$-alkyl, $C_1$–$C_3$-alkoxy or partially or fully halogenated $C_1$–$C_3$-alkoxy; or $R^8$ and $R^9$ together are a methylene chain having from 4 to 7 members;

—W—Z, where W is $C_2$–$C_4$-alkylene, ethoxyethylene, but-2-enylene or but-2-ynylene, and Z is a molecular moiety which is bonded to W in the ω-position and is the same as that linked to W in the α-position of W;

$R^6$ is hydrogen, $C_1$–$C_6$-alkyl or $C_3$–$C_6$-cycloalkyl, and $R^7$ is hydrogen, $C_1$–$C_6$-alkyl, —C($OR^{12}$)=N—H or —C($OR^{12}$)=N—($C_1$–$C_4$)-alkyl, where $R^{12}$ is $C_1$–$C_4$-alkyl, or $R^6$ and $R^7$ together are methylene having 4 or 5 members;

$R^3$ is hydrogen;

$C_1$–$C_6$-alkyl, which may carry from one to three of the following substituents: hydroxyl, halogen, $C_1$–$C_4$-alkoxy, $C_1$–$C_4$-alkylthio or di($C_1$–$C_4$)-alkylamino;

$C_3$–$C_8$-cycloalkyl, which may be monosubstituted, disubstituted or trisubstituted by halogen, $C_1$–$C_4$-alkyl or partially or fully halogenated $C_1$–$C_4$-alkyl;

$R^4$ is hydrogen, hydroxyl, $C_1$–$C_4$-alkoxy;

$C_1$–$C_6$-alkyl, which may carry from one to three of the following radicals: halogen, cyano, $C_1$–$C_4$-alkoxy, partially or fully halogenated $C_1$–$C_4$-alkoxy, $C_1$–$C_4$-alkylthio, partially or fully halogenated $C_1$–$C_4$-alkylthio, di-$C_1$–$C_4$-alkylamino, $C_3$–$C_8$-cycloalkl or phenyl, it being poossible for the phenyl ring to itself carry from one to three of the following radicals; halogen, cyano, nitro, $C_1$–$C_4$-alkyl, partially or fully halogenated $C_1$–$C_4$-alkyl, $C_1$–$C_4$-alkoxy, partially or fully halogenated $C_1$–$C_4$-alkoxy, $C_1$–$C_4$-alkylthio or partially or fully halogenated $C_1$–$C_4$-alkylthio;

$C_3$–$C_6$-cycloalkyl, which may carry from one to three of the following radicals: halogen, nitro, cyano, $C_1$–$C_6$-alkyl, partially or fully halogenated $C_1$–$C_6$-alkyl, $C_1$–$C_4$-alkoxy or partially or fully halogenated $C_1$–$C_4$-alkoxy;

$C_3$–$C_6$-alkenyl or $C_3$–$C_6$-alkynyl, each of which may be monosubstituted, disubstituted or trisubstituted by halogen and/or monosubstituted by phenyl, it being possible for the phenyl radical to itself carry from one to three of the following groups: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, halogen, cyano or nitro;

di($C_1$–$C_4$)-alkylamino;

phenyl, which may carry from one to four of the following groups: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, halogen, nitro, cyano, formyl, $C_1$–$C_4$-alkanoyl, $C_1$–$C_4$-haloalkanoyl or $C_1$–$C_4$-alkoxycarbonyl;

naphthyl, which maybe monosubstituted, disubstituted or trisubstituted by $C_1$–$C_4$-alkyl or halogen; or $R^3$ and $R^4$ together are methylene having from 4 to 7 members which maybe interrupted by oxygen, sulfur or N-methyl, or are —($CH_2$)$_3$—CO—, $R^3$ and $R^4$ in the compounds Ia or Ic not simultaneously being hydrogen if $R^1$ is hydrogen, methyl or phenyl and $R^2$ is $CONH_2$, COOH or $COOCH_3$, or if $R^1$ is CH($OCH_2CH_3$)$_2$ and $R^2$ is $CONH_2$, and the agriculturally acceptable salts of the compounds Ia, Ic, or Id.

2. A carboxamide of the formulae Ia, Ic and Id as set forth in claim 1, wherein $R^3$ is hydrogen.

3. A carboxamide of the formulae Ia, and Ic as set forth in claim 1, where $R^1$ is hydrogen, $C_1$–$C_4$-alkyl or $C_3$–$C_6$-cycloalkyl;

$R^2$ is

COYR$^5$, where Y is oxygen and R$^5$ is hydrogen or —NCR$^8$R$^9$, where

R$^8$ and R$^9$ are identical or different and each denotes hydrogen, C$_1$-C$_4$-alkyl or C$_3$-C$_6$-cycloalkyl, or together denote a C$_4$-C$_7$-alkylene chain;
R$^3$ is hydrogen, and
R$^4$ is C$_1$-C$_4$-alkyl or C$_3$-C$_8$-cycloalkyl.

4. A carboxamide of the formula Ia as set forth in claim 1.

5. A herbicidal composition containing inert carriers and a herbicidally effective amount of at least one carboxamide of the formulae Ia, Ic or Id as set forth in claim 1.

6. A herbicidal composition containing inert carriers and a herbicidally effective amount of at least one carboxamide of the formula Ia as set forth in claim 1.

7. A method of controlling the growth of unwanted plants, wherein a herbicidally effective amount of a carboxamide of the formula Ia', or Ic', where Ia', and Ic' have the meanings of Ia, and Ic without the disclaimer, is allowed to act on plants or their habitat, or on seed.

8. A carboxamide of the formula Ia as set forth in claim 1, wherein R$^1$ is methyl, R$^3$ is hydrogen, R$^4$ is tert.-butyl, R$^5$ is hydrogen and Y is O.

9. A carboxamide of the formula Ia as set forth in claim 1, wherein R$^1$ is methyl, R$^3$ is hydrogen, R$^4$ is tert.-butyl, R$^5$ is —N=C(CH$_3$)$_2$.

10. A carboxamide of the formula Ia as set forth in claim 1, wherein R$^1$ is iso-proyl, R$^3$ is hydrogen, R$^4$ is cyclo-propyl, R$^5$ is hydrogen and Y is O.

11. A carboxamide of the formula Ia as set forth in claim 1, wherein R$^1$ is iso-propyl, R$^3$ is hydrogen, R$^4$ is cyclo-propyl, R$^5$ is —N=C(CH$_3$)$_2$ and Y is O.

12. A carboxamide of the formula Ia as set forth in claim 1, wherein R$^1$ is iso-propyl, R$^3$ is hydrogen, R$^4$ is tert.-butyl, R$^5$ is —N=C(CH$_3$)$_2$ and Y is O.

13. A carboxamide of the formula Ia as set forth in claim 1, wherein R$^1$ is iso-propyl, R$^3$ is hydrogen, R$^4$ is tert.-butyl, R$^5$ is hydrogen and Y is O.

14. A carboxamide of the formula Ia as set forth in claim 1, wherein R$^1$ is sec.-butyl, R$^3$ is hydrogen, R$^4$ is cyclo-propyl, R$^5$ is hydrogen and Y is O.

15. A carboxamide of the formula Ia as set forth in claim 1, wherein R$^1$ is sec.-butyl, R$^3$ is hydrogen, R$^4$ is tert.-butyl, R$^5$ is —N=C(CH$_3$)$_2$ and Y is O.

16. A carboxamide of the formula Ia as set forth in claim 1, wherein R$^1$ is 1-methoxy-eth-1-yl, R$^3$ is hydrogen, R$^4$ is cyclo-propyl-methyl, R$^5$ is hydrogen and Y is O.

17. A carboxamide of the formula Ia as set forth in claim 1, wherein R$^1$ is 1-methoxy-eth-1-yl, R$^3$ is hydrogen, R$^4$ is cyclo-propyl-methyl, R$^5$ is —N=C(CH$_3$)$_2$ and Y is O.

18. A method of controlling the growth of unwanted plants, wherein a herbicidally effective amount of the carboxyamide of claim 8 is allowed to act on the plants, their habitat or on their seed.

19. A method of controlling the growth of unwanted plants, wherein a herbicidally effective amount of the carboxyamide of claim 9 is allowed to act on the plants, their habitat or on their seed.

20. A method of controlling the growth of unwanted plants, wherein a herbicidally effective amount of the carboxyamide of claim 11 is allowed to act on the plants, their habitat or on their seed.

21. A method of controlling the growth of unwanted plants, wherein a herbicidally effective amount of the carboxyamide of claim 12 is allowed to act on the plants, their habitat or on their seed.

22. A method of controlling the growth of unwanted plants, wherein a herbicidally effective amount of the carboxyamide of claim 13 is allowed to act on the plants, their habitat or on their seed.

23. A method of controlling the growth of unwanted plants, wherein a herbicidally effective amount of the carboxyamide of claim 14 is allowed to act on the plants, their habitat or on their seed.

24. A method of controlling the growth of unwanted plants, wherein a herbicidally effective amount of the carboxyamide of claim 15 is allowed to act on the plants, their habitat or on their seed.

25. A method of controlling the growth of unwanted plants, wherein a herbicidally effective amount of the carboxyamide of claim 16 is allowed to act on the plants, their habitat or on their seed.

26. A method of controlling the growth of unwanted plants, wherein a herbicidally effective amount of the carboxyamide of claim 17 is allowed to act on the plants, their habitat or on their seed.

27. A carboxamide the formula Ib where

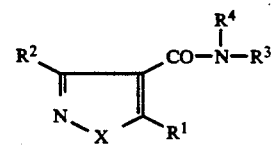

X is oxygen;
R$^1$ is
hydrogen, halogen, C$_1$-C$_8$-alkyl which may carry from one to five halogen atoms or a cyano radical or one to two C$_1$-C$_4$-alkoxy groups, C$_1$-C$_4$-alkoxy or C$_1$-C$_4$-alkylthio;
benzyl which may be monosubstituted, disubstituted or trisubstituted by C$_1$-C$_4$-alkyl, partially or fully halogenated C$_1$-C$_4$-alkyl, C$_1$-C$_4$-alkoxy, halogen, cyano or nitro;
phenyl which may also carry from one to three of the following radicals: cyano, nitro, halogen, C$_1$-C$_4$-alkyl, partially or fully halogenated C$_1$-C$_4$-alkyl, C$_1$-C$_4$-alkoxy, C$_1$-C$_4$-alkylthio; phenoxy or phenylthio, each of which may be monosubstituted, disubstituted or trisubstituted by C$_1$-C$_4$-alkyl, partially or fully halogenated C$_1$-C$_4$-alkyl, C$_1$-C$_4$-alkoxy, C$_1$-C$_4$-alkylthio, halogen, cyano or nitro; a 5- to 6-membered saturated or aromatic heterocyclic radical from the group consisting of 2-tetrahydrofuranyl, 3-tetrahydrofuranyl, 2-tetrahydrothienyl, 3-tetrahydrothienyl, 2-tetrahydropyranyl, 3-tetrahydropyranyl, 4-tetrahydropyranyl, 2-furanyl, 3-furanyl, 2-thienyl, or 3-thienyl, which may carry one or two of the following substituents: halogen, C$_1$-C$_3$-alkyl, C$_1$-C$_3$-alkoxy and C$_1$-C$_3$-alkoxycarbonyl;
C$_3$-C$_8$-cycloalkyl-substituted C$_1$-C$_6$-alkyl;
C$_2$-C$_6$-alkenyl whose double bond may be epoxidized, or C$_2$-C$_6$-alkynyl, it being possible for both groups to be monosubstituted, disubstituted or trisubstituted by halogen, C$_1$-C$_3$-alkoxy and/or monosubstituted by cyclopropyl or phenyl, it also being possible for the phenyl radical to carry up to three of the following substituents: halogen or C$_1$-C$_4$-alkyl;

$C_3$–$C_8$-cycloalkyl or $C_3$–$C_6$-cycloalkenyl, it being possible for both groups to be monosubstituted, disubstituted or trisubstituted by $C_1$–$C_4$-alkyl or halogen;

$R^2$ is formyl, 4,5-dihydrooxazol-2-yl, $COYR^5$ or $CONR^6R^7$, where

Y is oxygen or sulfur;

$R^5$ is hydrogen;

$C_1$–$C_6$-alkyl which may carry from one to five halogen atoms and/or up to three hydroxyl and/or $C_1$–$C_4$-alkoxy groups and/or one of the following radicals:

cyano, $C_1$–$C_4$-alkoxy-$C_2$–$C_4$-alkoxy, $C_1$–$C_3$-alkylthio, $C_1$–$C_3$-alkylamino, di($C_1$–$C_3$)-alkylamino, $C_3$–$C_6$-cycloalkylamino or di($C_3$–$C_6$)-cycloalkylamino, trimethylsilyl, $C_1$–$C_3$-alkylsulfinyl or $C_1$–$C_3$-alkylsulfonyl, carboxyl, $C_1$–$C_3$-alkoxycarbonyl, $C_1$–$C_3$-alkoxycarbonyl-$C_1$–$C_3$-alkoxy or $C_1$–$C_3$-alkoxycarbonyl-$C_1$–$C_3$-alkoxy-$C_1$–$C_3$-alkoxycarbonyl, di($C_1$–$C_3$)-alkylaminocarbonyl, di($C_1$–$C_3$)-alkoxyphosphonyl, $C_1$–$C_6$-alkaneiminoxy or $C_5$–$C_6$-cycloalkaneiminoxy, N-phthalimido, N-succinimido, benzyloxy, benzoyl, it being possible for these cyclic radicals to additionally carry from one to three of the following groups: halogen, $C_1$–$C_3$-alkyl or $C_1$–$C_3$-alkoxy, phenyl, which may also carry up to three of the following substituents: halogen, nitro, cyano, $C_1$–$C_3$-alkyl, partially or fully halogenated $C_1$–$C_3$-alkyl, $C_1$–$C_3$-alkoxy or partially or fully halogenated $C_1$–$C_3$-alkoxy;

—$CR^{10}$=N—$R^{11}$, where $R^{10}$ is hydrogen or $C_1$–$C_6$-alkyl and $R^{11}$ is $C_1$–$C_6$-alkoxy, $C_3$–$C_6$-alkenyloxy or $C_3$–$C_6$-alkynyloxy, each of which may carry up to 3 halogen atoms and/or a phenyl radical with up to three of the following radicals: halogen, nitro, cyano, $C_1$–$C_3$-alkyl or $C_1$–$C_3$-alkoxy; phenoxy, which may also carry up to three of the following substituents: halogen, nitro, cyano, $C_1$–$C_3$-alkyl or $C_1$–$C_3$-alkoxy; $C_1$–$C_6$-alkylamino, di($C_1$–$C_6$)alkylamino or phenylamino, it being possible for the aromatic ring to additionally carry up to three of the following radicals: halogen, nitro, cyano, $C_1$–$C_3$-alkyl or $C_1$–$C_3$-alkoxy;

$C_3$–$C_8$-cycloalkyl;

$C_3$–$C_6$-alkenyl, $C_5$–$C_6$-cycloalkenyl, $C_3$–$C_6$-alynyl, it being possible for these radicals to carry one of the following groups: hydroxyl, halogen, $C_1$–$C_4$-alkoxy or phenyl, it being possible for the aromatic radical to itself carry from one to three of the following groups: halogen, nitro, cyano, $C_1$–$C_4$-alkyl, phenyl, which may carry from one to three of the following groups: halogen, nitro cyano, $C_1$–$C_4$-alkyl, partially or fully halogenated $C_1$–$C_4$-alkyl, $C_1$–$C_4$-alkoxy, partially or fully halogenated $C_1$–$C_4$-alkoxy or $C_1$–$C_4$-alkoxycarbonyl;

N-phthalimido, tetrahydrophthalimido, succinimido, maleiimido;

2,2-dimethyl-1,3-dioxolan-4-ylmethyl or 1,3-dioxolan-2-on-4-ylmethyl;

in the case where Y=O: one equivalent of a cation from the group comprising the alkali and alkaline earth metals, manganese, copper, iron, ammonium and ammonium which substituted by up to 4 $C_1$–$C_3$-alkyl groups; or —N=$CR^8R^9$, where $R^8$ and $R^9$ are hydrogen; $C_1$–$C_4$-alkyl, which may be unsubstituted or partially or fully halogenated and may carry a $C_1$–$C_3$-alkoxy or phenyl radical, it being possible for the aromatic radical to itself also be monosubstituted, disubstituted or trisubstituted by halogen, nitro, cyano, $C_1$–$C_3$-alkyl, partially or fully halogenated $C_1$–$C_3$-alkyl, $C_1$–$C_3$-alkoxy or partially or fully halogenated $C_1$–$C_3$-alkoxy; $C_3$–$C_5$-cycloalkyl; $C_1$–$C_4$-alkoxy; furanyl or phenyl, which may additionally carry up to three of the following substituents: halogen, nitro, cyano, $C_1$–$C_3$-alkyl, partially or fully halogenated $C_1$–$C_3$-alkyl, $C_1$–$C_3$-alkoxy or partially or fully halogenated $C_1$–$C_3$-alkoxy; or $R^8$ and $R^9$ together are a methylene chain having from 4 to 7 members;

—W—Z, where W is $C_2$–$C_4$-alkylene, ethoxyethylene, but-2-ethylene or but-2-ynylene, and Z is a molecular moiety which is bonded to W in the $\omega$-position and is the same as the linked to W in the $\alpha$-position of W;

$R^6$ is hydrogen, $C_1$–$C_6$-alkyl or $C_3$–$C_8$-cycloalkyl, and $R^3$ is hydrogen, $C_1$–$C_6$-alkyl, —$C(OR^{12})$=N—H or —$C(OR^{12})$=N—($C_1$–$C_4$)-alkyl, where $R^{12}$ is $C_1$–$C_4$-alkyl, or $R^6$ and $R^7$ together are methylene having 4 to 5 members;

$R^3$ is hydrogen;

$C_1$–$C_6$-alkyl, which may carry from one to three of the following substituents: hydroxyl, halogen, $C_1$–$C_4$-alkoxy, $C_1$–$C_4$-alkythio or di($C_1$–$C_4$)-alkylamino;

$C_3$–$C_8$-cycloalkyl, which may be monosubstituted, disubstituted or trisubstituted by halogen, $C_1$–$C_4$-alkyl or partially or fully halogenated $C_1$–$C_4$-alkyl;

$R^4$ is hydrogen, hydroxyl, $C_1$–$C_4$-alkoxy;

$C_1$–$C_6$-alkyl, which may carry from one to three of the following radicals: halogen, cyano, $C_1$–$C_4$-alkoxy, partially or fully halogenated $C_1$–$C_4$-alkoxy, $C_1$–$C_4$-alkylthio, partially or fully halogenated $C_1$–$C_4$-alkylthio, di-$C_1$–$C_4$-alkylamino, $C_3$–$C_8$-cycloalkyl or phenyl, it being possible for the phenyl ring to itself carry from one to three of the following radicals: halogen, cyano, nitro, $C_1$–$C_4$-alkyl, partially or fully halogenated $C_1$–$C_4$-alkyl, $C_1$–$C_4$-alkoxy, partially or fully halogenated $C_1-C_4$-alkoxy, $C_1-C_4$-alkylthio or partially or fully halogenated $C_1-C_4$-alkylthio;

$C_3-C_8$-cycloalkyl, which may carry from one to three of the following radicals: halogen, nitro, cyano, $C_1-C_6$-alkyl, partially or fully halogenated $C_1-C_6$-alkyl, $C_1-C_4$-alkoxy or partially or fully halogenated $C_1-C_4$-alkoxy;

$C_3-C_6$-alkenyl or $C_3-C_6$-alkynyl, each of which may be monosubstituted, disubstituted or trisubstituted by halogen and/or monosubstituted by phenyl, it being possible for the phenyl radical to itself carry from one to three of the following groups: $C_1-C_4$-alkyl, $C_1-C_4$-haloalkyl, $C_1-C_4$-alkoxy, $C_1-C_4$-haloalkoxy, $C_1-C_4$-alkylthio, $C_1-C_4$-haloalkylthio, halogen, cyano or nitro;

di($C_1-C_4$)-alkylamino;

naphthyl, which may be monosubstituted, disubstituted or trisubstituted by $C_1-C_4$-alkyl or halogen; or $R^3$ and $R^4$ together are methylene having from 4 to 7 members which may be interrupted by oxygen, sulfur or N-methyl, or are $-(CH_2)_3-CO-$, $R^3$ and $R^4$ in the compound Ib not simultaneously being hydrogen if $R^1$ is hydrogen, methyl or phenyl and $R^2$ is $CONH_2$, COOH or $COOCH_3$, or if $R^1$ is $CH(OCH_2CH_3)_2$ and $R^2$ is $CONH_2$, and the agriculturally acceptable salts of the compound Ib.

* * * * *

UNITED STATES PATENT AND TRADEMARK OFFICE
CERTIFICATE OF CORRECTION

PATENT NO. : 5,201,932
DATED : April 13, 1993
INVENTOR(S) : MAYWALD et al.

It is certified that error appears in the above-identified patent and that said Letters Patent is hereby corrected as shown below:

IN THE CLAIMS

Claim 1, column 108, line 24, "poosible" should read --possible--.

Claim 27, column 112, line 33, "but-2-ethylene" should read --but-2-enylene--.

Claim 27, column 112, line 41, "$R^3$" should read --$R^7$--.

Signed and Sealed this

Eighteenth Day of January, 1994

Attest:

BRUCE LEHMAN

Attesting Officer       Commissioner of Patents and Trademarks